(12) United States Patent
Carroll et al.

(10) Patent No.: US 9,562,001 B2
(45) Date of Patent: Feb. 7, 2017

(54) MONOAMINE REUPTAKE INHIBITORS

(75) Inventors: Frank Ivy Carroll, Durham, NC (US); Bruce Edward Blough, Raleigh, NC (US); Philip Abraham, Cary, NC (US)

(73) Assignee: Research Triangle Institute, Research Triangle Park, NC (US)

(*) Notice: Subject to any disclaimer, the term of this patent is extended or adjusted under 35 U.S.C. 154(b) by 0 days.

(21) Appl. No.: 13/271,419

(22) Filed: Oct. 12, 2011

(65) Prior Publication Data
US 2012/0071560 A1 Mar. 22, 2012

Related U.S. Application Data

(63) Continuation of application No. PCT/US2010/031230, filed on Apr. 15, 2010.

(60) Provisional application No. 61/169,586, filed on Apr. 15, 2009.

(51) Int. Cl.
| | | |
|---|---|---|
| *A61K 31/137* | (2006.01) | |
| *C07C 225/18* | (2006.01) | |
| *A61P 25/24* | (2006.01) | |
| *A61P 3/04* | (2006.01) | |
| *A61P 25/34* | (2006.01) | |
| *A61P 25/00* | (2006.01) | |
| *A61P 3/00* | (2006.01) | |
| *A61P 25/16* | (2006.01) | |
| *A61P 25/22* | (2006.01) | |
| *A61P 25/06* | (2006.01) | |
| *A61P 25/36* | (2006.01) | |
| *A01N 33/24* | (2006.01) | |
| *C07C 225/16* | (2006.01) | |
| *C07C 211/27* | (2006.01) | |
| *C07C 211/29* | (2006.01) | |
| *C07C 211/35* | (2006.01) | |

(52) U.S. Cl.
CPC ............ *C07C 225/16* (2013.01); *C07C 211/27* (2013.01); *C07C 211/29* (2013.01); *C07C 211/35* (2013.01); *C07C 225/18* (2013.01); *C07C 2101/02* (2013.01); *C07C 2101/04* (2013.01); *C07C 2101/08* (2013.01); *C07C 2101/14* (2013.01)

(58) Field of Classification Search
USPC ................................. 514/649; 564/345, 342
See application file for complete search history.

(56) References Cited

U.S. PATENT DOCUMENTS

| | | | |
|---|---|---|---|
| 2,151,459 A | 3/1939 | Bockmühl et al. | |
| 2,776,993 A | 1/1957 | Alles | |
| 3,225,096 A * | 12/1965 | Mills et al. | 564/344 |
| 3,819,706 A | 6/1974 | Mehta | |
| 3,885,046 A | 5/1975 | Mehta | |
| 4,980,377 A | 12/1990 | Lafon | |
| 6,693,192 B1 | 2/2004 | Chrysselis et al. | |
| 8,906,908 B2 | 12/2014 | Carroll et al. | |

FOREIGN PATENT DOCUMENTS

| | | |
|---|---|---|
| DE | 2152686 | 5/1972 |
| EP | 0 007843 | 2/1980 |
| EP | 0 174 242 | 3/1986 |
| GB | 1 218 135 | 1/1971 |
| GB | 1 282 822 | 7/1972 |
| GB | 1 298 771 | 12/1972 |
| GB | 1 298 772 | 12/1972 |
| GB | 1 336 732 | 11/1993 |
| JP | H03206084 | 9/1991 |
| WO | WO 88/02254 | 4/1988 |
| WO | WO 99/37305 | 7/1999 |
| WO | WO 01/62257 | 8/2001 |
| WO | WO 2005/066194 | 7/2005 |

OTHER PUBLICATIONS

Sayed et al., "Reactions of N,N-Diarylethylenediimines with Grignard Reagents, henylisocyanate and Succinic Anhydride Part-III," *J. Chem. Soc. Pak.*, 1987, pp. 53-56, vol. 9, No. 1.

Cloonan et al., "Synthesis and Serotonin Transporter Activity of Sulphur-Substituted α-alkyl Phenethylamines as a New Class of Anticancer Agents," *European Journal of Medicinal Chemistry*, 2009, pp. 4862-4888, vol. 44.

Magyar et al. "Structure-Activity Relationship of Selective Inhibitors of MAO-B" Adv. Pharmacol. Res. Pract., Proc. Congr. Hung. Pharmacol. Soc., 3$^{rd}$ (1980), Meeting Date 1979, vol. 4, Issue Monoamine Oxidases Their Selective Inhibition, 11-21.

Kafka et al., Syntheses of 3-aminoquinoline-2,4(1H,3H)-diones, Heterocycles, 2002, vol. 57, No. 9, pp. 1659-1682.

Talaty et al., The reaction of α—lactams with Grignard reagents: A correction of the literature, Tetrahedron Letters, 1976, vol. 52, pp. 4797-4800.

Balsamo et al., "Synthesis and Pharmacological Properties of *cis*-2-(2,5-dimethoxyphenyl)-3-Methylmorpholine and Its N-isopropyl Derivative," *Eur. J. Med. Chem.—Chimica Therapeutica*, 1978, pp. 321-326, vol. 13, No. 4.

Hu et al., "Synthesis of 2-aryl-3,5,5-trimethyl-2-morpholinol Hydrochloride," *Yingyong Huaxue*, 2005, pp. 343-345, vol. 22, No. 3.

Lukas et al., "Synthesis and Characterization of In Vitro and In Vivo Profiles of Hydroxybupropion analogues: Aids to Smoking Cessation," *Journal of Medicinal Chemistry*, 2010, pp. 4731-4748, vol. 53.

Stevens et al., "Epoxy Ethers. XX. Synthesis of Diamines, Morpholines, and Piperazines," *Journal of Organic Chemistry*, 1964, pp. 3146-3151, vol. 29.

(Continued)

*Primary Examiner* — Kathrien Cruz
(74) *Attorney, Agent, or Firm* — Womble Carlyle Sandridge & Rice, LLP

(57) ABSTRACT

The invention provides bupropion analog compounds capable of inhibiting the reuptake of one or more monoamines. The compounds may selectively bind to one or more monoamine transporters, including those for dopamine, norepinephrine, and serotonin. Such compounds may be used to treat conditions that are responsive to inhibition of the reuptake of monoamines, including addiction, depression, and obesity.

5 Claims, No Drawings

(56) References Cited

OTHER PUBLICATIONS

Wee et al., "Relationship Between the Serotonergic Activity and Reinforcing Effects of a Series of Amphetamine Analogs," *The Journal of Pharmacology and Experimental Therapeutics*, 2005, pp. 848-854, vol. 313, No. 2.
Barger et al., "Phenolic Derivatives of p-Phenylethylamine," *Proceedings of the Chemical Society*, (1911) London, 26, 248—Accession No. 1911:6032 CAPLUS
Boswell et al, "Synthesis and Anti-tetrabenazine Activity of C-3 Analogues of Dimethyl-2-phenylmorpholines," *J. Heterocyclic Chemisty*, 1996, vol. 33 (1), p. 33-9.
Carroll et al., "Synthesis and Biological Evaluation of Bupropion Analogues as Potential Pharmacotherapies for Smoking Cessation," *J. Medicinal Chem.*, 2010, vol. 53 (5) pp. 2204-2214.
Hu et al., "Synthesis of 2-Aryl-3,5,5-trimethyl-2-morpholinols Hydrochloride," *Chinese Journal of Applied Chemistry*, 2005, vol. 22, No. 3, pp. 343-345.
Skita et al., "A New Synthesis of 1,2-amino Ketones," *Berichte der Deutschen Chemischen Gesellschaft [Abteilung] B: Abhandlungen* (1933), 66B, 858-66—Accession No. 1933:41264 CAPLUS.
Boswell et al., "Synthesis and Anti-Tetrabenazine Activity of C-3 Analogues of Dimethyl-2-Phenylmorpholines," *J. Heterocyclic Chem.*, pp. 33-39, vol. 33, No. 33, 1996.
Carroll et al., "Synthesis and Biological Evaluation of Bupropion analogues as Potential Pharmacotherapies for Cocaine Addiction," *J. Med. Chem.*, 2009, pp. 6768-6781, vol. 52.
Carroll et al., "Synthesis and Biological Evaluation of Bupropion analogues as Potential Pharmacotherapies for Cocaine Addiction," *J. Med. Chem.*, 2010, pp. 2204-2214, vol. 53.
Foley et al., "Novel Aminopropiophenones as Potential Antidepressants," *Drug Development Research*, pp. 252-260, vol. 60, No. 4, 2003. http://www3.interscience.wiley.com/journal/106564270/abstract?CRETRY=1&SRETRY=0.
Fuller et al., "Inhibition of Monoamine Oxidase by N-Phenacyl-Cyclopropylamine,"*Biochemical Pharmacology*, 1978, pp. 2255-2261, vol. 27.
Meltzer et al., "1-(4-Methylphenyl)-2-pyrrolidin-l-yl-pentan-l-one (Pyrovalerone) Analogues: A Promising Class of Monoamine Uptake Inhibitors," *J. Med. Chem.*, 2006, pp. 1420-1432, vol. 49.
Musso et al., "Synthesis and Evaluation of the Anticonvulsant Activity of a Series of 2-Amino-1-Phenyl-l-Propanols Derived from the Metabolites of the Antidepressant Bupropion," *Bioorganic & Medicinal Chemistry Letters*, 1997, pp. 1-6, vol. 7.

* cited by examiner

MONOAMINE REUPTAKE INHIBITORS

CROSS-REFERENCE TO RELATED APPLICATIONS

This application is a continuation of international application number PCT/US2010/031230, filed Apr. 15, 2010, which claims priority to U.S. Provisional Patent Application No. 61/169,586, filed Apr. 15, 2009, both of which are incorporated herein by reference in their entirety and for all purposes.

FEDERALLY SPONSORED RESEARCH OR DEVELOPMENT

This invention was made with United States Government support under R01DA12970 and N01DA18815, awarded by the National Institute of Health. The United States Government has certain rights in the invention.

FIELD OF THE INVENTION

The present application is directed to various compounds and methods of preparation of compounds that are capable of functioning as monoamine reuptake inhibitors. The application is also directed to pharmaceutical compositions containing one or more monoamine reuptake inhibitors, which may also contain one or more additional therapeutic agents. It is also directed to methods of treatment of various conditions that may be responsive to inhibition of monoamine reuptake, such as addiction and depression.

BACKGROUND OF THE INVENTION

Drug abuse and addiction are significant medical problems in the United States. According to the 2007 National Survey on Drug Use and Health, a reported 19.9 million Americans aged 12 or older were current illicit drug users, meaning that they had used an illicit drug during the month prior to the survey. This estimate represents 0.8 percent of the population aged 12 years old or older. An estimated 3.2 million were classified with dependence on or abuse of both alcohol and illicit drugs, and 3.7 million were dependent on or abused illicit drugs but not alcohol.

Cocaine has one of the highest rates of abuse, and the annual number of new cocaine users continues to steadily increase. In 2007, there were 2.1 million current cocaine users aged 12 or older. Cocaine is a powerfully addictive drug, often leading to severe medical complications including cardiovascular effects, such as disturbances in heart rhythm and heart attacks; respiratory effects such as chest pain and respiratory failure; neurological effects, including strokes, seizures, and headaches; and gastrointestinal complications, such as abdominal pain and nausea. In addition to its direct effects, cocaine abuse has also contributed to the increase of the spread of human immunodeficiency virus (HIV) infection and drug-resistant tuberculosis. As a result, considerable effort has been devoted to the development of a pharmacotherapy to treat patients addicted to cocaine; however, no effective medication is yet available for use in the clinic.

Indirect dopamine agonists have been postulated to be a class of compounds that may show promise for the treatment of cocaine addiction. Studies directed toward the development of indirect dopamine agonists have involved structurally diverse classes of compounds including analogues of 3-phenyltropane, 1,4-dialkylpiperazines, phenylpiperidine, benztropine, methylphenidate, and mazindol.

Bupropion ((±)-2-tert-butylamino-3'-chloropropiophenone, Wellbutrin®) is a well-known antidepressant that has been widely used for the past 30 years. Although the neurochemical mechanisms underlying its action still are not well defined, bupropion is thought to function, at least in part, as an indirect dopamine agonist. It is known to inhibit the reuptake of dopamine (DA) and norepinephrine (NE) but, unlike many other antidepressants, has very little effect on serotonin (5HT) reuptake. Its antidepressant effects have been attributed to its effects on the noradrenergic system, but some reports suggest that bupropion is more potent as a DA reuptake inhibitor than an NE reuptake inhibitor. Microdialysis studies have shown that acute bupropion administration increases extracellular DA. In behavioral pharmacology studies, bupropion has been shown to induce locomotor activity, generalize to cocaine and amphetamine in drug discrimination (DS) studies, produce condition place preference (CPP), and is self-administered in both rats and non-human primates. In addition, bupropion has been reported to increase response on a fixed interval (FI) schedule stimulus-shock termination study in squirrel monkeys. These studies appear to demonstrate bupropion's action as a DA reuptake inhibitor and, thus, indicate that bupropion has the properties of an indirect dopamine agonist.

Bupropion has shown efficacy in addiction. It has been formulated in a sustained release formulation for nicotine addiction and is currently marketed for this purpose as Zyban®. In a clinical trial of bupropion for cocaine abuse, an exploratory analysis suggested that patients with depression may have benefited. Another clinical study has evaluated bupropion-augmented contingency management for cocaine dependence in methadone-maintained patients, finding that the combination of contingency management with bupropion treatment may successfully reduce cocaine use, although there was no evidence for efficacy of bupropion alone. Bupropion has also been studied as a treatment for methamphetamine dependence. In one study, bupropion reduced methamphetamine-induced subjective effects and cue-induced craving. In another study, treatment with bupropion reduced methamphetamine use in relatively light users.

Although bupropion is a successful treatment for both depression and nicotine addiction, relatively few chemical analogues have been prepared and evaluated. Structural analogues of bupropion that function by the same mechanisms of action may be successful in treating depression and nicotine addiction, as well as possibly other related diseases, including addictions of other types and obesity.

SUMMARY OF THE INVENTION

The present invention provides compounds useful as monoamine reuptake inhibitors and methods of synthesis of such compounds. It also provides pharmaceutical compositions containing the compounds, which may be useful in the treatment of various conditions or disorders that may be responsive to the inhibition of monoamine reuptake by cells. The invention further provides methods of treating such conditions and disorders, including but not limited to, depression and addiction. For example, in one aspect, the invention is directed to a method of treating a condition comprising administering to a subject in need of treatment of the condition a pharmaceutical composition comprising a therapeutically effective amount of a compound of the present invention or a pharmaceutically acceptable ester, amide, salt, solvate, prodrug, or isomer thereof.

Accordingly, in one aspect, the present invention provides a compound that inhibits the reuptake of one or more monoamines. In some embodiments, the invention provides a compound according to the following structure:

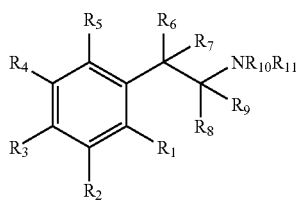

Formula I wherein:

$R_1$-$R_5$ are each independently selected from H, OH, optionally substituted C1-4 alkyl, optionally substituted C1-3 alkoxy, optionally substituted C2-4 alkenyl, optionally substituted C2-4 alkynyl, halogen, amino, acylamido, CN, $CF_3$, $NO_2$, $N_3$, $CONH_2$, $CO_2R_{12}$, $CH_2OR_{12}$, $NR_{12}R_{13}$, $NHCOR_{12}$, $NHCO_2R_{12}$, $CONR_{12}R_{13}$; C1-3 alkylthio, $R_{12}SO$, $R_{12}SO_2$, $CF_3S$, and $CF_3SO_2$;

$R_6$ and $R_7$ are each independently selected from H or optionally substituted C1-10alkyl, or $R_6$ and $R_7$ together constitute =O or =$CH_2$;

$R_8$ and $R_9$ are each independently selected from H or optionally substituted C1-10alkyl;

$R_{10}$, $R_{11}$, $R_{12}$, and $R_{13}$ are each independently selected from H or optionally substituted C1-10 alkyl;

and wherein $R_1$ and $R_8$ may be joined to form a cyclic ring; or a pharmaceutically acceptable ester, amide, salt, solvate, prodrug, or isomer thereof, with the proviso that when one of $R_8$ and $R_9$ is $CH_3$, then at least one of $R_{10}$ and $R_{11}$ is optionally substituted C3-C10 cycloalkyl.

In some aspects, the invention provides a compound of Formula I, wherein one of $R_{10}$ and $R_{11}$ is H and the other of $R_{10}$ and $R_{11}$ is optionally substituted C3-10 cycloalkyl. In certain aspects, the C3-10 cycloalkyl is selected from cyclopropyl, cyclobutyl, and cyclopentyl. In some aspects, the invention provides a compound of Formula I, wherein one of $R_{10}$ and $R_{11}$ is H and the other of $R_{10}$ and $R_{11}$ is optionally substituted tert-butyl.

In some aspects, the invention provides a compound of Formula I, wherein one or both of $R_8$ and $R_9$ are C2-C7 alkyl. In certain aspects, one of $R_8$ and $R_9$ is C2-C7 alkyl and the other of $R_8$ and $R_9$ is H. For example, in some aspects, the C2-C7 alkyl is selected from the group consisting of ethyl, propyl, butyl, hexyl, or isobutyl.

In some aspects, the invention provides a compound of Formula I, wherein one or more of $R_1$, $R_2$, $R_3$, $R_4$, or $R_5$ is a substituent other than H. For example, in certain aspects, the substituent comprises halo, and in particular embodiments, comprises chloro. Further, in certain aspects, $R_6$ and $R_7$ together constitute =O.

In certain aspects, the invention provides a compound selected from 2-(N-cyclopropylamino)-3'-chloropropiophenone, 2-(N-cyclopropylamino)-3'-chlorobutyrophenone, 2-(N-cyclopropylamino)-3'-chloropentanophenone, 2-(N-cyclobutylamino)-3'-chloropropiophenone, 2-(N-cyclopentylamino)-3'-chloropropiophenone, 2-(N-tert-butylamino)-3'-chlorobutyrophenone; 2-(N-tert-butylamino)-3',4'-dichlorobutyrophenone; 2-(N-tert-butylamino)-3'-chloropentanophenone; 2-(N-tert-butylamino)-3',4'-dichloropentanophenone; 2-(N-tert-butylamino)-3'-chlorohexanophenone; 2-(N-tert-butylamino)-3'-chloroheptanophenone; 2-(N-tert-butylamino)-3'-chlorooctanophenone; and 2-(N-tert-butylamino)-3'-chlorophenyl-4-methylpentanophenone.

In another aspect of the invention is provided a method for treating or delaying the progression of disorders that are alleviated by inhibiting monoamine reuptake in a patient, the method comprising administering a therapeutically effective amount of at least one compound of Formula I. The disorder for which treatment is administered may be, but is not limited to, the group consisting of addiction, depression, obesity, bipolar disorder, attention deficit disorder (ADD), attention-deficit/hyperactivity disorder (ADHD), hypoactive sexual desire disorder, antidepressant-induced sexual dysfunction, orgasmic dysfunction, seasonal affective disorder/winter depression, mania, bulimia and other eating disorders, panic disorders, obsessive compulsive disorder, schitzophrenia, schitzo-affective disorder, Parkinson's disease, narcolepsy, anxiety disorders, insomnia, chronic pain, migraine headaches, and restless legs syndrome. In particular, the method may relate to treatment for addiction to cocaine, methamphetamine, or nicotine.

In a further aspect of the invention is provided a pharmaceutical composition comprising a compound according to Formula I and a pharmaceutically acceptable carrier.

DETAILED DESCRIPTION OF THE INVENTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The present invention provides compounds that may function as monoamine reuptake inhibitors, as well as methods of preparation and pharmaceutical compositions thereof. It also provides methods for using such compounds to treat a variety of disorders that may be responsive to the inhibition of monoamine reuptake. In particular, the compositions and methods can be used in the treatment of various drug addictions, depression, and obesity. Treatment can comprise the use of a compound of the present invention as a single active agent. In other embodiments, treatment can comprise the use of a compound of the present invention in combination with one or more further active agents. The specific pharmaceutical composition (or compositions) used in the invention, and the methods of treatment provided by the invention, are further described below.

DEFINITIONS

The term "alkyl" as used herein means saturated straight, branched, or cyclic hydrocarbon groups (i.e., cycloalkyl). In particular embodiments, alkyl refers to groups comprising 1 to 10 carbon atoms ("C1-10 alkyl"). In further embodiments, alkyl refers to groups comprising 1 to 8 carbon atoms ("C1-8 alkyl"), 1 to 6 carbon atoms ("C1-6 alkyl"), or 1 to 4 carbon atoms ("C1-4 alkyl"). In other embodiments, alkyl refers to groups comprising 3-10 carbon atoms ("C3-10 alkyl"), 3-8 carbon atoms ("C3-8 alkyl"), or 3-6 carbon atoms ("C3-6 alkyl"). In specific embodiments, alkyl refers to methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl.

The term "optionally substituted" refers to moieties optionally containing one or more distinct substituent groups therein, such as one or more of the following substituent groups: halo (e.g., Cl, F, Br, and I); halogenated alkyl (e.g., $CF_3$, 2-Br-ethyl, $CH_2F$, $CH_2Cl$, $CH_2CF_3$, or $CF_2CF_3$; hydroxyl; amino; carboxylate; carboxamido; alkylamino; arylamino; alkoxy; aryloxy; nitro; azido; cyano; thio; sulfonic acid; sulfate; phosphonic acid; phosphate; and phosphonate.

The term "alkenyl" as used herein means alkyl moieties wherein at least one saturated C—C bond is replaced by a double bond. In particular embodiments, alkenyl refers to groups comprising 2 to 10 carbon atoms ("C2-10 alkenyl"). In further embodiments, alkenyl refers to groups comprising 2 to 8 carbon atoms ("C2-8 alkenyl"), 2 to 6 carbon atoms ("C2-6 alkenyl"), or 2 to 4 carbon atoms ("C2-4 alkenyl"). In specific embodiments, alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl.

The term "alkynyl" as used herein means alkyl moieties wherein at least one saturated C—C bond is replaced by a triple bond. In particular embodiments, alkynyl refers to groups comprising 2 to 10 carbon atoms ("C2-10 alkynyl"). In further embodiments, alkynyl refers to groups comprising 2 to 8 carbon atoms ("C2-8 alkynyl"), 2 to 6 carbon atoms ("C2-6 alkynyl"), or 2 to 4 carbon atoms ("C2-4 alkynyl"). In specific embodiments, alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl.

The term "alkoxy" as used herein means straight or branched chain alkyl groups linked by an oxygen atom (i.e., —O-alkyl), wherein alkyl is as described above. In particular embodiments, alkoxy refers to oxygen-linked groups comprising 1 to 10 carbon atoms ("C1-10 alkoxy"). In further embodiments, alkoxy refers to oxygen-linked groups comprising 1 to 8 carbon atoms ("C1-8 alkoxy"), 1 to 6 carbon atoms ("C1-6 alkoxy"), 1 to 4 carbon atoms ("C1-4 alkoxy") or 1 to 3 carbon atoms ("C1-3 alkoxy").

The term "halo" or "halogen" as used herein means fluorine, chlorine, bromine, or iodine.

The term "alkylthio" as used herein means a thio group with one or more alkyl substituents, where alkyl is defined as above.

The term "acylamido" refers to an amide group with one or more acyl substituents, where acyl is as defined below.

The term "acyl" as used herein means a group that can be represented by C(=O)R, in which R is selected from H, alkyl; alkoxy; alkoxyalkyl including methoxymethyl; aralkyl including optionally substituted benzyl; aryloxyalkyl such as phenoxymethyl; aryl including phenyl optionally substituted with halogen, C1-C6 alkyl or C1-C6 alkoxy; sulfonate esters such as alkyl or aralkyl sulphonyl including methanesulfonyl; amino, mono-, di-, or triphosphate ester; trityl or monomethoxytrityl; trialkylsilyl such as dimethyl-t-butylsilyl or diphenylmethylsilyl.

The terms "aralkyl" and "arylalkyl" as used herein mean an aryl group as defined above linked to the molecule through an alkyl group as defined above.

The terms "alkaryl" and "alkylaryl" as used herein means an alkyl group as defined above linked to the molecule through an aryl group as defined above.

The term "amino" as used herein means a moiety represented by the structure $NR_2$, and includes primary amines, and secondary and tertiary amines substituted by alkyl (i.e., alkylamino). Thus, $R_2$ may represent two hydrogen atoms, two alkyl moieties, or one hydrogen atom and one alkyl moiety.

The term "cycloalkyl" means a non-aromatic, monocyclic or polycyclic ring comprising carbon and hydrogen atoms.

The term "aryl" as used herein means a stable monocyclic, bicyclic, or tricyclic carbon ring of up to 8 members in each ring, wherein at least one ring is aromatic as defined by the Hückel 4n+2 rule. Exemplary aryl groups according to the invention include phenyl, naphthyl, tetrahydronaphthyl, and biphenyl.

The term "analogue" as used herein means a compound in which one or more individual atoms or functional groups have been replaced, either with a different atom or a different functional, generally giving rise to a compound with similar properties.

The term "derivative" as used herein means a compound that is formed from a similar, beginning compound by attaching another molecule or atom to the beginning compound. Further, derivatives, according to the invention, encompass one or more compounds formed from a precursor compound through addition of one or more atoms or molecules or through combining two or more precursor compounds.

The term "prodrug" as used herein means any compound which, when administered to a mammal, is converted in whole or in part to a compound of the invention.

The term "active metabolite" as used herein means a physiologically active compound which results from the metabolism of a compound of the invention, or a prodrug thereof, when such compound or prodrug is administered to a mammal.

The terms "therapeutically effective amount" or "therapeutically effective dose" as used herein are interchangeable and mean a concentration of a compound according to the invention, or a biologically active variant thereof, sufficient to elicit the desired therapeutic effect according to the methods of treatment described herein.

The term "pharmaceutically acceptable carrier" as used herein means a carrier that is conventionally used in the art to facilitate the storage, administration, and/or the healing effect of a biologically active agent.

The term "intermittent administration" as used herein means administration of a therapeutically effective dose of a composition according to the invention, followed by a time period of discontinuance, which is then followed by another administration of a therapeutically effective dose, and so forth.

The term "monoamine" as used herein encompasses monoamine neurotransmitters and neuromodulators. In particular, it is used to refer to dopamine, norepinephrine, and serotonin. Monoamine transporters facilitate the reuptake or reabsorption of these monoamines into the presynapses of an individual.

Active Agents

The invention provides bupropion analogue compounds having the following structure:

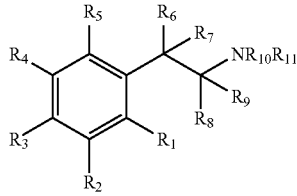

Formula I wherein:

$R_1$-$R_5$ are each independently selected from H, OH, optionally substituted C1-4 alkyl, optionally substituted C1-3 alkoxy, optionally substituted C2-4 alkenyl, optionally substituted C2-4 alkynyl, halogen, amino, acylamido, CN, $CF_3$, $NO_2$, $N_3$, $CONH_2$, $CO_2R_{12}$, $CH_2OR_{12}$, $NR_{12}R_{13}$, $NHCOR_{12}$, $NHCO_2R_{12}$, $CONR_{12}R_{13}$; C1-3 alkylthio, $R_{12}SO$, $R_{12}SO_2$, $CF_3S$, and $CF_3SO_2$;

$R_6$ and $R_7$ are each independently selected from H or optionally substituted C1-10 alkyl, or $R_6$ and $R_7$ together constitute =O or =$CH_2$;

$R_8$ and $R_9$ are each independently selected from H or optionally substituted C1-10 alkyl;

$R_{10}$, $R_{11}$, $R_{12}$, and $R_{13}$ are each independently selected from H or optionally substituted C1-10 alkyl;

and wherein $R_1$ and $R_8$ may be joined to form a cyclic ring;

or a pharmaceutically acceptable ester, amide, salt, solvate, prodrug, or isomer thereof, with the proviso that when one of $R_8$ and $R_9$ is $CH_3$, then at least one of $R_{10}$ and $R_{11}$ is optionally substituted C3-C10 cycloalkyl.

Such compounds of the present invention may be capable of affecting monoamine uptake efficacy. In particular, in some embodiments, compounds of the present invention may be capable of inhibiting dopamine and/or norepinephrine reuptake. In preferred embodiments, the compounds may be capable of selectively inhibiting dopamine reuptake.

In preferred embodiments of Formula I, $R_1$-$R_5$ are independently H or a halogen. In some embodiments, $R_1$ and $R_5$ are H and $R_2$-$R_4$ may be H or halogen. In some preferred embodiments, one of $R_8$ and $R_9$ is H and the other is an optionally substituted C1-C10 alkyl. In additional preferred embodiments, $R_6$ and $R_7$ together constitute =O. In some preferred embodiments, one of $R_{10}$ and $R_{11}$ is H and the other of $R_{10}$ and $R_{11}$ is an optionally substituted cycloalkyl. In some additional preferred embodiments, one of $R_{10}$ and $R_{11}$ is H and the other of $R_{10}$ and $R_{11}$ is an optionally substituted cyclopropyl. According to one embodiment, at least one of $R_8$ or $R_9$ is a C2-C10 alkyl and/or at least one of $R_{10}$ and $R_{11}$ is a C3-C10 cycloalkyl.

In particular embodiments, compounds according to the following structure are provided:

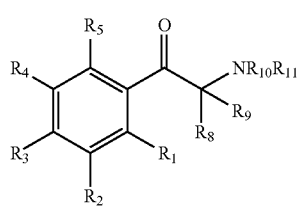

Formula Ia wherein:

$R_1$-$R_5$ are each independently selected from H, OH, optionally substituted C1-4 alkyl, optionally substituted C1-3 alkoxy, optionally substituted C2-4 alkenyl, optionally substituted C2-4 alkynyl, halogen, amino, acylamido, CN, $CF_3$, $NO_2$, $N_3$, $CONH_2$, $CO_2R_{12}$, $CH_2OR_{12}$, $NR_{12}R_{13}$, $NHCOR_{12}$, $NHCO_2R_{12}$, $CONR_{12}R_{13}$; C1-3 alkylthio, $R_{12}SO$, $R_{12}SO_2$, $CF_3S$, and $CF_3SO_2$;

$R_8$ and $R_9$ are each independently selected from H or optionally substituted C1-10 alkyl;

$R_{10}$, $R_{11}$, $R_{12}$, and $R_{13}$ are each independently selected from H or optionally substituted C1-10 alkyl;

and wherein $R_1$ and $R_8$ may be joined to form a cyclic ring, or a pharmaceutically acceptable ester, amide, salt, solvate, prodrug, or isomer thereof, with the proviso that when one of $R_8$ and $R_9$ is $CH_3$, then at least one of $R_{10}$ and $R_{11}$ is optionally substituted C3-C10 cycloalkyl.

In preferred embodiments of Formula Ia, $R_1$-$R_5$ are independently H or a halogen. In some embodiments, $R_1$ and $R_5$ are H and $R_2$-$R_4$ may be H or halogen. In some preferred embodiments, one of $R_8$ and $R_9$ is H and the other is an optionally substituted C1-C10 alkyl. In additional preferred embodiments, one of $R_{10}$ and $R_{11}$ is H and the other of $R_{10}$ and $R_{11}$ is an optionally substituted cycloalkyl. In some additional preferred embodiments, one of $R_{10}$ and $R_{11}$ is H and the other of $R_{10}$ and $R_{11}$ is an optionally substituted cyclopropyl.

In further particular embodiments, compounds according to the following structure are provided:

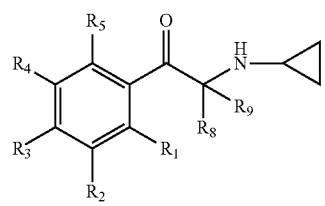

Formula Ib wherein:

$R_1$-$R_5$ are each independently selected from H, OH, optionally substituted C1-4 alkyl, optionally substituted C1-3 alkoxy, optionally substituted C2-4 alkenyl, optionally substituted C2-4 alkynyl, halogen, amino, acylamido, CN, $CF_3$, $NO_2$, $N_3$, $CONH_2$, $CO_2R_{12}$, $CH_2OR_{12}$, $NR_{12}R_{13}$, $NHCOR_{12}$, $NHCO_2R_{12}$, $CONR_{11}R_{13}$; C1-3 alkylthio, $R_{12}SO$, $R_{12}SO_2$, $CF_3S$, and $CF_3SO_2$;

$R_8$ and $R_9$ are each independently selected from H or optionally substituted C1-10 alkyl;

$R_{12}$ and $R_{13}$ are each independently selected from H or optionally substituted C1-10alkyl;

and wherein $R_1$ and $R_8$ may be joined to form a cyclic ring, or a pharmaceutically acceptable ester, amide, salt, solvate, prodrug, or isomer thereof.

In preferred embodiments of Formula Ib, $R_1$-$R_5$ are independently H or a halogen. In some embodiments, $R_1$ and $R_5$ are H and $R_2$-$R_4$ may be H or halogen. In some preferred embodiments, one of $R_8$ and $R_9$ is H and the other is an optionally substituted C1-C10 alkyl.

In some embodiments, compounds with one or more chiral centers are provided. While racemic mixtures of compounds of the invention can be active, selective, and bioavailable, isolated isomers may be of interest as well.

The compounds disclosed herein as active agents may contain chiral centers, which may be either of the (R) or (S) configuration, or may comprise a mixture thereof. Accordingly, the present invention also includes stereoisomers of the compounds described herein, where applicable, either individually or admixed in any proportions. Stereoisomers may include, but are not limited to, enantiomers, diastereomers, racemic mixtures, and combinations thereof. Such stereoisomers can be prepared and separated using conventional techniques, either by reacting enantiomeric starting materials, or by separating isomers of compounds of the present invention. Isomers may include geometric isomers. Examples of geometric isomers include, but are not limited to, cis isomers or trans isomers across a double bond. Other isomers are contemplated among the compounds of the present invention. The isomers may be used either in pure form or in admixture with other isomers of the compounds described herein.

Various methods are known in the art for preparing optically active forms and determining activity. Such methods include standard tests described herein other similar tests which are will known in the art. Examples of methods that can be used to obtain optical isomers of the compounds according to the present invention include the following:

i) physical separation of crystals whereby macroscopic crystals of the individual enantiomers are manually separated. This technique may particularly be used when crystals of the separate enantiomers exist (i.e., the material is a conglomerate), and the crystals are visually distinct;

ii) simultaneous crystallization whereby the individual enantiomers are separately crystallized from a solution of the racemate, possible only if the latter is a conglomerate in the solid state;

iii) enzymatic resolutions whereby partial or complete separation of a racemate by virtue of differing rates of reaction for the enantiomers with an enzyme;

iv) enzymatic asymmetric synthesis, a synthetic technique whereby at least one step of the synthesis uses an enzymatic reaction to obtain an enantiomerically pure or enriched synthetic precursor of the desired enantiomer;

v) chemical asymmetric synthesis whereby the desired enantiomer is synthesized from an achiral precursor under conditions that produce asymmetry (i.e., chirality) in the product, which may be achieved using chiral catalysts or chiral auxiliaries;

vi) diastereomer separations whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomers;

viii) kinetic resolutions comprising partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors whereby the desired enantiomer is obtained from non-chiral starting materials and where the stereochemical integrity is not or is only minimally compromised over the course of the synthesis;

x) chiral liquid chromatography whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography whereby the racemate is volatilized and enantiomers are separated by virtue of their differing interactions in the gaseous mobile phase with a column containing a fixed non-racemic chiral adsorbent phase;

xii) extraction with chiral solvents whereby the enantiomers are separated by virtue of preferential dissolution of one enantiomer into a particular chiral solvent; and xiii) transport across chiral membranes whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

The compound optionally may be provided in a composition that is enantiomerically enriched, such as a mixture of enantiomers in which one enantiomer is present in excess, in particular to the extent of 95% or more, or 98% or more, including 100%.

In some embodiments, a compound according to Formula I is provided, wherein $R_6$ and $R_7$ are not the same substituent, forming a chiral center at the carbon to which $R_6$ and $R_7$ are attached. The compound may be the R or S enantiomer. In some embodiments, a compound according to Formula I is provided, wherein $R_8$ and $R_9$ are not the same substituent, forming a chiral center at the carbon to which $R_8$ and $R_9$ are attached. The compound may be the R or S enantiomer. In some embodiments, $R_6$ and $R_7$ are not the same substituent, forming a chiral center at the carbon to which $R_6$ and $R_7$ are attached and $R_8$ and $R_9$ are not the same substituent, forming a chiral center at the carbon to which $R_8$ and $R_9$ are attached. These compounds may be (R,R), (S,S), (R,S), or (S,R) isomers.

The terms (R), (S), (R,R), (S,S), (R,S) and (S,R) as used herein mean that the composition contains a greater proportion of the named isomer of the compound in relation to other isomers. In a preferred embodiment, these terms indicate that the composition contains at least 90% by weight of the named isomer and 10% by weight or less of the one or more other isomers; or more preferably about 95% by weight of the named isomer and 5% or less of the one or more other isomers. These percentages are based on the total amount of the compound of the present invention present in the composition.

The compounds of the present invention may be utilized per se or in the form of a pharmaceutically acceptable ester, amide, salt, solvate, prodrug, or isomer. For example, the compound may be provided as a pharmaceutically acceptable salt. If used, a salt of the drug compound should be both pharmacologically and pharmaceutically acceptable, but non-pharmaceutically acceptable salts may conveniently be used to prepare the free active compound or pharmaceutically acceptable salts thereof and are not excluded from the scope of this invention. Such pharmacologically and pharmaceutically acceptable salts can be prepared by reaction of the drug with an organic or inorganic acid, using standard methods detailed in the literature. Examples of pharmaceutically acceptable salts of the compounds useful according to the invention include acid addition salts. Salts of non-pharmaceutically acceptable acids, however, may be useful, for example, in the preparation and purification of the compounds. Suitable acid addition salts according to the present invention include organic and inorganic acids. Preferred salts include those formed from hydrochloric, hydrobromic, sulfuric, phosphoric, citric, tartaric, lactic, pyruvic, acetic, succinic, fumaric, maleic, oxaloacetic, methanesulfonic, ethanesulfonic, p-toluenesulfonic, benzenesulfonic, and isethionic acids. Other useful acid addition salts include propionic acid, glycolic acid, oxalic acid, malic acid, malonic acid, benzoic acid, cinnamic acid, mandelic acid, salicylic acid, and the like. Particular example of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxyenzoates, phthalates, sulfonates, xylenesulfonates, phenylacetates, phenylpropionates, phenylbutyrates, citrates, lactates, γ-hydroxybutyrates, glycolates, tartrates, methanesulfonates, propanesulfonates, naphthalene-1-sulfonates, naphthalene-2-sulfonates, and mandelates.

An acid addition salt may be reconverted to the free base by treatment with a suitable base. Preparation of basic salts of acid moieties which may be present on a compound useful according to the present invention may be prepared in a similar manner using a pharmaceutically acceptable base, such as sodium hydroxide, potassium hydroxide, ammonium hydroxide, calcium hydroxide, triethylamine, or the like.

Esters of the active agent compounds according to the present invention may be prepared through functionalization of hydroxyl and/or carboxyl groups that may be present within the molecular structure of the compound. Amides and prodrugs may also be prepared using techniques known to those skilled in the art. For example, amides may be prepared from esters, using suitable amine reactants, or they may be prepared from anhydride or an acid chloride by reaction with ammonia or a lower alkyl amine. Moreover, esters and amides of compounds of the invention can be made by reaction with a carbonylating agent (e.g., ethyl formate, acetic anhydride, methoxyacetyl chloride, benzoyl chloride, methyl isocyanate, ethyl chloroformate, methanesulfonyl chloride) and a suitable base (e.g., 4-dimethylaminopyridine, pyridine, triethylamine, potassium carbonate) in a suitable organic solvent (e.g., tetrahydrofuran, acetone, methanol, pyridine, N,N-dimethylformamide) at a temperature of 0° C. to 60° C. Prodrugs are typically prepared by covalent attachment of a moiety, which results in a compound that is therapeutically inactive until modified by an individual's metabolic system. Examples of pharmaceutically acceptable solvates include, but are not limited to, compounds according to the invention in combination with water, isopropanol, ethanol, methanol, DMSO, ethyl acetate, acetic acid, or ethanolamine.

In the case of solid compositions, it is understood that the compounds used in the methods of the invention may exist in different forms. For example, the compounds may exist in stable and metastable crystalline forms and isotropic and amorphous forms, all of which are intended to be within the scope of the present invention.

If a compound useful as an active agent according to the invention is a base, the desired salt may be prepared by any suitable method known to the art, including treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, pyranosidyl acids such as glucuronic acid and galacturonic acid, alpha-hydroxy acids such as citric acid and tartaric acid, amino acids such as aspartic acid and glutamic acid, aromatic acids such as benzoic acid and cinnamic acid, sulfonic acids such a p-toluenesulfonic acid or ethanesulfonic acid, or the like.

If a compound described herein as an active agent is an acid, the desired salt may be prepared by any suitable method known to the art, including treatment of the free acid with an inorganic or organic base, such as an amine (primary, secondary or tertiary), an alkali metal or alkaline earth metal hydroxide or the like. Illustrative examples of suitable salts include organic salts derived from amino acids such as glycine and arginine, ammonia, primary, secondary and tertiary amines, and cyclic amines such as piperidine, morpholine and piperazine, and inorganic salts derived from sodium, calcium, potassium, magnesium, manganese, iron, copper, zinc, aluminum and lithium.

The present invention further includes prodrugs and active metabolites of the active agent compounds described herein. Any of the compounds described herein can be administered as a prodrug to increase the activity, bioavailability, or stability of the compound or to otherwise alter the properties of the compound. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, and/or dephosphorylated to produce the active compound.

A number of prodrug ligands are known. In general, alkylation, acylation, or other lipophilic modification of one or more heteroatoms of the compound, such as a free amine or carboxylic acid residue, reduces polarity and allows passage into cells. Examples of substituent groups that can replace one or more hydrogen atoms on the free amine and/or carboxylic acid moiety include, but are not limited to, the following: aryl; steroids; carbohydrates (including sugars); 1,2-diacylglycerol; alcohols; acyl (including lower acyl); alkyl (including lower alkyl); sulfonate ester (including alkyl or arylalkyl sulfonyl, such as methanesulfonyl and benzyl, wherein the phenyl group is optionally substituted with one or more substituents as provided in the definition of an aryl given herein); optionally substituted arylsulfonyl; lipids (including phospholipids); phosphotidylcholine; phosphocholine; amino acid residues or derivatives; amino acid acyl residues or derivatives; peptides; cholesterols; or other pharmaceutically acceptable leaving groups which, when administered in vivo, provide the free amine and/or carboxylic acid moiety. Any of these can be used in combination with the disclosed active agents to achieve a desired effect.

In particular embodiments, the present invention provides a compound wherein $R_6$ and $R_7$ together constitute =O. In particular embodiments, the present invention provides a compound wherein $R_8$ and $R_9$ are independently selected from H and optionally substituted C1-10 alkyl. In some embodiments, $R_8$ and $R_9$ are independently selected from H and optionally substituted C1-7 alkyl, preferably C1-6 alkyl. In some embodiments, $R_8$ and $R_9$ are independently selected from H and optionally substituted C2-7 alkyl, preferably C2-6 alkyl. In some embodiments, one of $R_8$ and $R_9$ is H and the other of $R_8$ and $R_9$ is optionally substituted C1-10 alkyl. In some embodiments, one of $R_8$ and $R_9$ is H and the other of $R_8$ and $R_9$ is optionally substituted C1-7 alkyl, and preferably, is optionally substituted C1-6 alkyl. In some embodiments, one of $R_8$ and $R_9$ is H and the other of $R_8$ and $R_9$ is optionally substituted C2-7 alkyl, and preferably, is optionally substituted C2-6 alkyl. In some embodiments, the C2-C7 alkyl is selected from the group consisting of ethyl, propyl, butyl, hexyl, or isobutyl. In some embodiments, one of $R_8$ and $R_9$ is H and the other of $R_8$ and $R_9$ is optionally substituted C1-4 alkyl, preferably C2-4 alkyl. In certain embodiments, one of $R_{10}$ and $R_{11}$ is H and the other of $R_{10}$ and $R_{11}$ is optionally substituted C1-10 alkyl. In some embodiments, one of $R_{10}$ and $R_{11}$ is H and the other of $R_{10}$ and $R_{11}$ is tert-butyl. In some embodiments, one of $R_{10}$ and $R_{11}$ is H and the other of $R_{10}$ and $R_{11}$ is optionally substituted C3-10 cycloalkyl. In some embodiments, the cycloalkyl is selected from the group consisting of cyclopropyl, cyclobutyl, and cyclopentyl. In particular embodiments, the present invention provides a compound wherein one or more of $R_1$-$R_5$ is a substituent other than H. For example, in some embodiments, one or more of $R_1$-$R_5$ is a halogen (e.g., Cl, Br, or I).

Particularly preferred compounds of the present invention include the following:

2-(N-cyclopropylamino)-3'-chloropropiophenone;

2-(N-cyclopropylamino)-3'-chlorobutyrophenone;

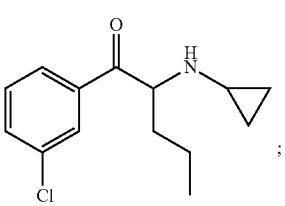

2-(N-cyclopropylamino)-3'-chloropentanophenone

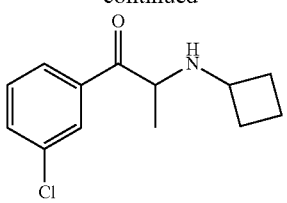

2-(N-cyclobutylamino)-3'-chloropropiophenone;

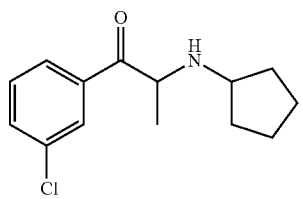

2-(N-cyclopentylamino)-3'-chloropropiophenone;

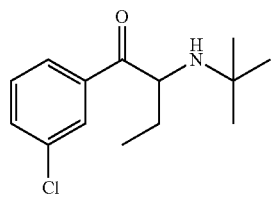

2-(N-tert-butylamino)-3'-chlorobutyrophenone;

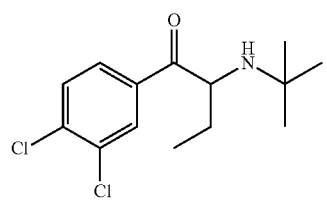

2-(N-tert-butylamino)-3',4'-dichlorobutyrophenone;

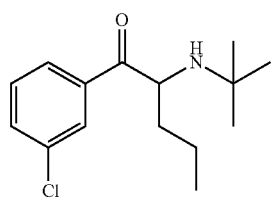

2-(N-tert-butylamino)-3'-chloropentanophenone;

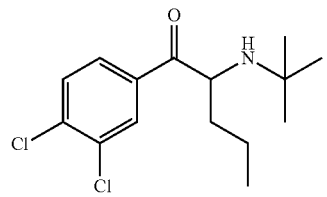

2-(N-tert-butylamino)-3',4'-dichloropentanophenone;

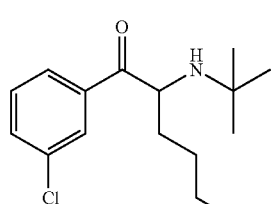

2-(N-tert-butylamino)-3'-chlorohexanophenone;

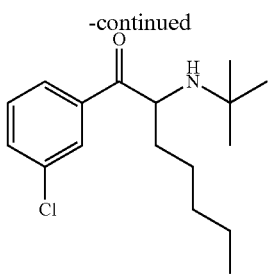

2-(N-tert-butylamino)-3'-chloroheptanophenone;

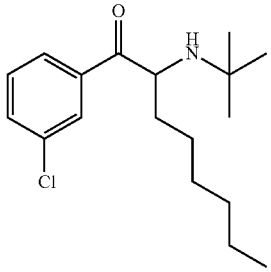

2-(N-tert-butylamino)-3'-chlorooctanophenone; and

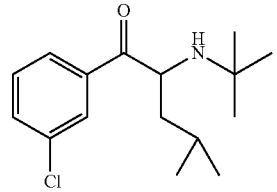

2-(N-tert-butylamino)-3'-chlorophenyl-4-methylpentanophenone.

Additional representative, non-limiting compounds of Formula I of the present invention are indicated below in Table 1, wherein $R_{11}$ is a cycloalkyl.

TABLE 1

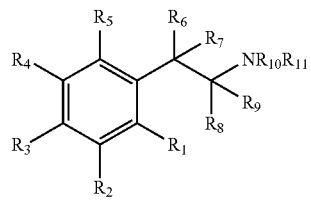

Formula I

Representative compounds of Formula I

| $R_1$ | $R_2$ | $R_3$ | $R_4$ | $R_5$ | $R_6$ | $R_7$ | $R_8$ | $R_9$ | $R_{10}$ | $R_{11}$ |
|---|---|---|---|---|---|---|---|---|---|---|
| H | H | H | H | H | $CH_3$ | H | $CH_3$ | H | H | $CH(CH_2CH_2)$ |
| H | Cl | H | H | H | $CH_3$ | H | $CH_3$ | H | H | $CH(CH_2CH_2)$ |
| H | H | Cl | H | H | $CH_3$ | H | $CH_3$ | H | H | $CH(CH_2CH_2)$ |
| H | H | H | Cl | H | $CH_3$ | H | $CH_3$ | H | H | $CH(CH_2CH_2)$ |
| H | Br | H | H | H | $CH_3$ | H | $CH_3$ | H | H | $CH(CH_2CH_2)$ |
| H | H | Br | H | H | $CH_3$ | H | $CH_3$ | H | H | $CH(CH_2CH_2)$ |
| H | H | H | Br | H | $CH_3$ | H | $CH_3$ | H | H | $CH(CH_2CH_2)$ |
| H | $CH_3$ | H | H | H | $CH_3$ | H | $CH_3$ | H | H | $CH(CH_2CH_2)$ |
| H | H | $CH_3$ | H | H | $CH_3$ | H | $CH_3$ | H | H | $CH(CH_2CH_2)$ |
| H | H | H | $CH_3$ | H | $CH_3$ | H | $CH_3$ | H | H | $CH(CH_2CH_2)$ |
| H | F | H | H | H | $CH_3$ | H | $CH_3$ | H | H | $CH(CH_2CH_2)$ |
| H | H | F | H | H | $CH_3$ | H | $CH_3$ | H | H | $CH(CH_2CH_2)$ |
| H | H | H | F | H | $CH_3$ | H | $CH_3$ | H | H | $CH(CH_2CH_2)$ |
| H | Cl | Cl | H | H | $CH_3$ | H | $CH_3$ | H | H | $CH(CH_2CH_2)$ |
| H | Br | Br | H | H | $CH_3$ | H | $CH_3$ | H | H | $CH(CH_2CH_2)$ |
| H | F | F | H | H | $CH_3$ | H | $CH_3$ | H | H | $CH(CH_2CH_2)$ |
| H | $CH_3$ | $CH_3$ | H | H | $CH_3$ | H | $CH_3$ | H | H | $CH(CH_2CH_2)$ |
| H | Cl | $CH_3$ | H | H | $CH_3$ | H | $CH_3$ | H | H | $CH(CH_2CH_2)$ |
| H | Br | $CH_3$ | H | H | $CH_3$ | H | $CH_3$ | H | H | $CH(CH_2CH_2)$ |
| H | F | $CH_3$ | H | H | $CH_3$ | H | $CH_3$ | H | H | $CH(CH_2CH_2)$ |
| H | $CH_3$ | Cl | H | H | $CH_3$ | H | $CH_3$ | H | H | $CH(CH_2CH_2)$ |
| H | $CH_3$ | Br | H | H | $CH_3$ | H | $CH_3$ | H | H | $CH(CH_2CH_2)$ |
| H | $CH_3$ | F | H | H | $CH_3$ | H | $CH_3$ | H | H | $CH(CH_2CH_2)$ |
| H | Cl | H | Cl | H | $CH_3$ | H | $CH_3$ | H | H | $CH(CH_2CH_2)$ |
| H | Br | H | Br | H | $CH_3$ | H | $CH_3$ | H | H | $CH(CH_2CH_2)$ |
| H | F | H | F | H | $CH_3$ | H | $CH_3$ | H | H | $CH(CH_2CH_2)$ |
| H | $CH_3$ | H | $CH_3$ | H | $CH_3$ | H | $CH_3$ | H | H | $CH(CH_2CH_2)$ |
| H | Cl | H | Cl | H | $CH_3$ | H | $CH_3$ | H | H | $CH(CH_2CH_2)$ |
| H | Br | H | Br | H | $CH_3$ | H | $CH_3$ | H | H | $CH(CH_2CH_2)$ |
| H | F | H | F | H | $CH_3$ | H | $CH_3$ | H | H | $CH(CH_2CH_2)$ |
| H | H | $CH_3$ | $CH_3$ | H | $CH_3$ | H | $CH_3$ | H | H | $CH(CH_2CH_2)$ |
| H | H | Cl | Cl | H | $CH_3$ | H | $CH_3$ | H | H | $CH(CH_2CH_2)$ |
| H | H | Br | Br | H | $CH_3$ | H | $CH_3$ | H | H | $CH(CH_2CH_2)$ |

TABLE 1-continued

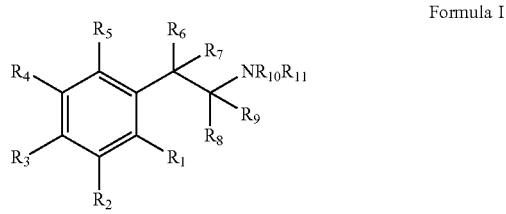

Formula I

Representative compounds of Formula I

| $R_1$ | $R_2$ | $R_3$ | $R_4$ | $R_5$ | $R_6$ | $R_7$ | $R_8$ | $R_9$ | $R_{10}$ | $R_{11}$ |
|---|---|---|---|---|---|---|---|---|---|---|
| H | H | F | F | H | $CH_3$ | H | $CH_3$ | H | H | $CH(CH_2CH_2)$ |
| H | H | Cl | $CH_3$ | H | $CH_3$ | H | $CH_3$ | H | H | $CH(CH_2CH_2)$ |
| H | H | Br | $CH_3$ | H | $CH_3$ | H | $CH_3$ | H | H | $CH(CH_2CH_2)$ |
| H | H | F | $CH_3$ | H | $CH_3$ | H | $CH_3$ | H | H | $CH(CH_2CH_2)$ |
| H | H | $CH_3$ | Cl | H | $CH_3$ | H | $CH_3$ | H | H | $CH(CH_2CH_2)$ |
| H | H | $CH_3$ | Br | H | $CH_3$ | H | $CH_3$ | H | H | $CH(CH_2CH_2)$ |
| H | H | $CH_3$ | F | H | $CH_3$ | H | $CH_3$ | H | H | $CH(CH_2CH_2)$ |
| H | H | H | H | H | $CH_3$ | H | $CH_3$ | H | H | $CH(CH_2CH_2CH_2)$ |
| H | Cl | H | H | H | $CH_3$ | H | $CH_3$ | H | H | $CH(CH_2CH_2CH_2)$ |
| H | H | Cl | H | H | $CH_3$ | H | $CH_3$ | H | H | $CH(CH_2CH_2CH_2)$ |
| H | H | H | Cl | H | $CH_3$ | H | $CH_3$ | H | H | $CH(CH_2CH_2CH_2)$ |
| H | Br | H | H | H | $CH_3$ | H | $CH_3$ | H | H | $CH(CH_2CH_2CH_2)$ |
| H | H | Br | H | H | $CH_3$ | H | $CH_3$ | H | H | $CH(CH_2CH_2CH_2)$ |
| H | H | H | Br | H | $CH_3$ | H | $CH_3$ | H | H | $CH(CH_2CH_2CH_2)$ |
| H | $CH_3$ | H | H | H | $CH_3$ | H | $CH_3$ | H | H | $CH(CH_2CH_2CH_2)$ |
| H | H | $CH_3$ | H | H | $CH_3$ | H | $CH_3$ | H | H | $CH(CH_2CH_2CH_2)$ |
| H | H | H | $CH_3$ | H | $CH_3$ | H | $CH_3$ | H | H | $CH(CH_2CH_2CH_2)$ |
| H | F | H | H | H | $CH_3$ | H | $CH_3$ | H | H | $CH(CH_2CH_2CH_2)$ |
| H | H | F | H | H | $CH_3$ | H | $CH_3$ | H | H | $CH(CH_2CH_2CH_2)$ |
| H | H | H | F | H | $CH_3$ | H | $CH_3$ | H | H | $CH(CH_2CH_2CH_2)$ |
| H | Cl | Cl | H | H | $CH_3$ | H | $CH_3$ | H | H | $CH(CH_2CH_2CH_2)$ |
| H | Br | Br | H | H | $CH_3$ | H | $CH_3$ | H | H | $CH(CH_2CH_2CH_2)$ |
| H | F | F | H | H | $CH_3$ | H | $CH_3$ | H | H | $CH(CH_2CH_2CH_2)$ |
| H | $CH_3$ | $CH_3$ | H | H | $CH_3$ | H | $CH_3$ | H | H | $CH(CH_2CH_2CH_2)$ |
| H | Cl | $CH_3$ | H | H | $CH_3$ | H | $CH_3$ | H | H | $CH(CH_2CH_2CH_2)$ |
| H | Br | $CH_3$ | H | H | $CH_3$ | H | $CH_3$ | H | H | $CH(CH_2CH_2CH_2)$ |
| H | F | $CH_3$ | H | H | $CH_3$ | H | $CH_3$ | H | H | $CH(CH_2CH_2CH_2)$ |
| H | $CH_3$ | Cl | H | H | $CH_3$ | H | $CH_3$ | H | H | $CH(CH_2CH_2CH_2)$ |
| H | $CH_3$ | Br | H | H | $CH_3$ | H | $CH_3$ | H | H | $CH(CH_2CH_2CH_2)$ |
| H | $CH_3$ | F | H | H | $CH_3$ | H | $CH_3$ | H | H | $CH(CH_2CH_2CH_2)$ |
| H | Cl | H | Cl | H | $CH_3$ | H | $CH_3$ | H | H | $CH(CH_2CH_2CH_2)$ |
| H | Br | H | Br | H | $CH_3$ | H | $CH_3$ | H | H | $CH(CH_2CH_2CH_2)$ |
| H | F | H | F | H | $CH_3$ | H | $CH_3$ | H | H | $CH(CH_2CH_2CH_2)$ |
| H | $CH_3$ | H | $CH_3$ | H | $CH_3$ | H | $CH_3$ | H | H | $CH(CH_2CH_2CH_2)$ |
| H | Cl | H | Cl | H | $CH_3$ | H | $CH_3$ | H | H | $CH(CH_2CH_2CH_2)$ |
| H | Br | H | Br | H | $CH_3$ | H | $CH_3$ | H | H | $CH(CH_2CH_2CH_2)$ |
| H | F | H | F | H | $CH_3$ | H | $CH_3$ | H | H | $CH(CH_2CH_2CH_2)$ |
| H | H | $CH_3$ | $CH_3$ | H | $CH_3$ | H | $CH_3$ | H | H | $CH(CH_2CH_2CH_2)$ |
| H | H | Cl | Cl | H | $CH_3$ | H | $CH_3$ | H | H | $CH(CH_2CH_2CH_2)$ |
| H | H | Br | Br | H | $CH_3$ | H | $CH_3$ | H | H | $CH(CH_2CH_2CH_2)$ |
| H | H | F | F | H | $CH_3$ | H | $CH_3$ | H | H | $CH(CH_2CH_2CH_2)$ |
| H | H | Cl | $CH_3$ | H | $CH_3$ | H | $CH_3$ | H | H | $CH(CH_2CH_2CH_2)$ |
| H | H | Br | $CH_3$ | H | $CH_3$ | H | $CH_3$ | H | H | $CH(CH_2CH_2CH_2)$ |
| H | H | F | $CH_3$ | H | $CH_3$ | H | $CH_3$ | H | H | $CH(CH_2CH_2CH_2)$ |
| H | H | $CH_3$ | Cl | H | $CH_3$ | H | $CH_3$ | H | H | $CH(CH_2CH_2CH_2)$ |
| H | H | $CH_3$ | Br | H | $CH_3$ | H | $CH_3$ | H | H | $CH(CH_2CH_2CH_2)$ |
| H | H | $CH_3$ | F | H | $CH_3$ | H | $CH_3$ | H | H | $CH(CH_2CH_2CH_2)$ |
| H | H | H | H | H | $CH_2CH_3$ | H | $CH_3$ | H | H | $CH(CH_2CH_2)$ |
| H | Cl | H | H | H | $CH_2CH_3$ | H | $CH_3$ | H | H | $CH(CH_2CH_2)$ |
| H | H | Cl | H | H | $CH_2CH_3$ | H | $CH_3$ | H | H | $CH(CH_2CH_2)$ |
| H | H | H | Cl | H | $CH_2CH_3$ | H | $CH_3$ | H | H | $CH(CH_2CH_2)$ |
| H | Br | H | H | H | $CH_2CH_3$ | H | $CH_3$ | H | H | $CH(CH_2CH_2)$ |
| H | H | Br | H | H | $CH_2CH_3$ | H | $CH_3$ | H | H | $CH(CH_2CH_2)$ |
| H | H | H | Br | H | $CH_2CH_3$ | H | $CH_3$ | H | H | $CH(CH_2CH_2)$ |
| H | $CH_3$ | H | H | H | $CH_2CH_3$ | H | $CH_3$ | H | H | $CH(CH_2CH_2)$ |
| H | H | $CH_3$ | H | H | $CH_2CH_3$ | H | $CH_3$ | H | H | $CH(CH_2CH_2)$ |
| H | H | H | $CH_3$ | H | $CH_2CH_3$ | H | $CH_3$ | H | H | $CH(CH_2CH_2)$ |
| H | F | H | H | H | $CH_2CH_3$ | H | $CH_3$ | H | H | $CH(CH_2CH_2)$ |
| H | H | F | H | H | $CH_2CH_3$ | H | $CH_3$ | H | H | $CH(CH_2CH_2)$ |
| H | H | H | F | H | $CH_2CH_3$ | H | $CH_3$ | H | H | $CH(CH_2CH_2)$ |
| H | Cl | Cl | H | H | $CH_2CH_3$ | H | $CH_3$ | H | H | $CH(CH_2CH_2)$ |
| H | Br | Br | H | H | $CH_2CH_3$ | H | $CH_3$ | H | H | $CH(CH_2CH_2)$ |
| H | F | F | H | H | $CH_2CH_3$ | H | $CH_3$ | H | H | $CH(CH_2CH_2)$ |
| H | $CH_3$ | $CH_3$ | H | H | $CH_2CH_3$ | H | $CH_3$ | H | H | $CH(CH_2CH_2)$ |
| H | Cl | $CH_3$ | H | H | $CH_2CH_3$ | H | $CH_3$ | H | H | $CH(CH_2CH_2)$ |

TABLE 1-continued

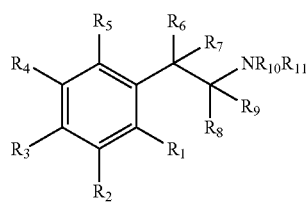

Formula I

Representative compounds of Formula I

| $R_1$ | $R_2$ | $R_3$ | $R_4$ | $R_5$ | $R_6$ | $R_7$ | $R_8$ | $R_9$ | $R_{10}$ | $R_{11}$ |
|---|---|---|---|---|---|---|---|---|---|---|
| H | Br | $CH_3$ | H | H | $CH_2CH_3$ | H | $CH_3$ | H | H | $CH(CH_2CH_2)$ |
| H | F | $CH_3$ | H | H | $CH_2CH_3$ | H | $CH_3$ | H | H | $CH(CH_2CH_2)$ |
| H | $CH_3$ | Cl | H | H | $CH_2CH_3$ | H | $CH_3$ | H | H | $CH(CH_2CH_2)$ |
| H | $CH_3$ | Br | H | H | $CH_2CH_3$ | H | $CH_3$ | H | H | $CH(CH_2CH_2)$ |
| H | $CH_3$ | F | H | H | $CH_2CH_3$ | H | $CH_3$ | H | H | $CH(CH_2CH_2)$ |
| H | Cl | H | Cl | H | $CH_2CH_3$ | H | $CH_3$ | H | H | $CH(CH_2CH_2)$ |
| H | Br | H | Br | H | $CH_2CH_3$ | H | $CH_3$ | H | H | $CH(CH_2CH_2)$ |
| H | F | H | F | H | $CH_2CH_3$ | H | $CH_3$ | H | H | $CH(CH_2CH_2)$ |
| H | $CH_3$ | H | $CH_3$ | H | $CH_2CH_3$ | H | $CH_3$ | H | H | $CH(CH_2CH_2)$ |
| H | Cl | H | Cl | H | $CH_2CH_3$ | H | $CH_3$ | H | H | $CH(CH_2CH_2)$ |
| H | Br | H | Br | H | $CH_2CH_3$ | H | $CH_3$ | H | H | $CH(CH_2CH_2)$ |
| H | F | H | F | H | $CH_2CH_3$ | H | $CH_3$ | H | H | $CH(CH_2CH_2)$ |
| H | H | $CH_3$ | $CH_3$ | H | $CH_2CH_3$ | H | $CH_3$ | H | H | $CH(CH_2CH_2)$ |
| H | H | Cl | Cl | H | $CH_2CH_3$ | H | $CH_3$ | H | H | $CH(CH_2CH_2)$ |
| H | H | Br | Br | H | $CH_2CH_3$ | H | $CH_3$ | H | H | $CH(CH_2CH_2)$ |
| H | H | F | F | H | $CH_2CH_3$ | H | $CH_3$ | H | H | $CH(CH_2CH_2)$ |
| H | H | Cl | $CH_3$ | H | $CH_2CH_3$ | H | $CH_3$ | H | H | $CH(CH_2CH_2)$ |
| H | H | Br | $CH_3$ | H | $CH_2CH_3$ | H | $CH_3$ | H | H | $CH(CH_2CH_2)$ |
| H | H | F | $CH_3$ | H | $CH_2CH_3$ | H | $CH_3$ | H | H | $CH(CH_2CH_2)$ |
| H | H | $CH_3$ | Cl | H | $CH_2CH_3$ | H | $CH_3$ | H | H | $CH(CH_2CH_2)$ |
| H | H | $CH_3$ | Br | H | $CH_2CH_3$ | H | $CH_3$ | H | H | $CH(CH_2CH_2)$ |
| H | H | $CH_3$ | F | H | $CH_2CH_3$ | H | $CH_3$ | H | H | $CH(CH_2CH_2)$ |
| H | H | H | H | H | $CH_2CH_3$ | H | $CH_3$ | H | H | $CH(CH_2CH_2CH_2)$ |
| H | Cl | H | H | H | $CH_2CH_3$ | H | $CH_3$ | H | H | $CH(CH_2CH_2CH_2)$ |
| H | H | Cl | H | H | $CH_2CH_3$ | H | $CH_3$ | H | H | $CH(CH_2CH_2CH_2)$ |
| H | H | H | Cl | H | $CH_2CH_3$ | H | $CH_3$ | H | H | $CH(CH_2CH_2CH_2)$ |
| H | Br | H | H | H | $CH_2CH_3$ | H | $CH_3$ | H | H | $CH(CH_2CH_2CH_2)$ |
| H | H | Br | H | H | $CH_2CH_3$ | H | $CH_3$ | H | H | $CH(CH_2CH_2CH_2)$ |
| H | H | H | Br | H | $CH_2CH_3$ | H | $CH_3$ | H | H | $CH(CH_2CH_2CH_2)$ |
| H | $CH_3$ | H | H | H | $CH_2CH_3$ | H | $CH_3$ | H | H | $CH(CH_2CH_2CH_2)$ |
| H | H | $CH_3$ | H | H | $CH_2CH_3$ | H | $CH_3$ | H | H | $CH(CH_2CH_2CH_2)$ |
| H | H | H | $CH_3$ | H | $CH_2CH_3$ | H | $CH_3$ | H | H | $CH(CH_2CH_2CH_2)$ |
| H | F | H | H | H | $CH_2CH_3$ | H | $CH_3$ | H | H | $CH(CH_2CH_2CH_2)$ |
| H | H | F | H | H | $CH_2CH_3$ | H | $CH_3$ | H | H | $CH(CH_2CH_2CH_2)$ |
| H | H | H | F | H | $CH_2CH_3$ | H | $CH_3$ | H | H | $CH(CH_2CH_2CH_2)$ |
| H | Cl | Cl | H | H | $CH_2CH_3$ | H | $CH_3$ | H | H | $CH(CH_2CH_2CH_2)$ |
| H | Br | Br | H | H | $CH_2CH_3$ | H | $CH_3$ | H | H | $CH(CH_2CH_2CH_2)$ |
| H | F | F | H | H | $CH_2CH_3$ | H | $CH_3$ | H | H | $CH(CH_2CH_2CH_2)$ |
| H | $CH_3$ | $CH_3$ | H | H | $CH_2CH_3$ | H | $CH_3$ | H | H | $CH(CH_2CH_2CH_2)$ |
| H | Cl | $CH_3$ | H | H | $CH_2CH_3$ | H | $CH_3$ | H | H | $CH(CH_2CH_2CH_2)$ |
| H | Br | $CH_3$ | H | H | $CH_2CH_3$ | H | $CH_3$ | H | H | $CH(CH_2CH_2CH_2)$ |
| H | F | $CH_3$ | H | H | $CH_2CH_3$ | H | $CH_3$ | H | H | $CH(CH_2CH_2CH_2)$ |
| H | $CH_3$ | Cl | H | H | $CH_2CH_3$ | H | $CH_3$ | H | H | $CH(CH_2CH_2CH_2)$ |
| H | $CH_3$ | Br | H | H | $CH_2CH_3$ | H | $CH_3$ | H | H | $CH(CH_2CH_2CH_2)$ |
| H | $CH_3$ | F | H | H | $CH_2CH_3$ | H | $CH_3$ | H | H | $CH(CH_2CH_2CH_2)$ |
| H | Cl | H | Cl | H | $CH_2CH_3$ | H | $CH_3$ | H | H | $CH(CH_2CH_2CH_2)$ |
| H | Br | H | Br | H | $CH_2CH_3$ | H | $CH_3$ | H | H | $CH(CH_2CH_2CH_2)$ |
| H | F | H | F | H | $CH_2CH_3$ | H | $CH_3$ | H | H | $CH(CH_2CH_2CH_2)$ |
| H | $CH_3$ | H | $CH_3$ | H | $CH_2CH_3$ | H | $CH_3$ | H | H | $CH(CH_2CH_2CH_2)$ |
| H | Cl | H | Cl | H | $CH_2CH_3$ | H | $CH_3$ | H | H | $CH(CH_2CH_2CH_2)$ |
| H | Br | H | Br | H | $CH_2CH_3$ | H | $CH_3$ | H | H | $CH(CH_2CH_2CH_2)$ |
| H | F | H | F | H | $CH_2CH_3$ | H | $CH_3$ | H | H | $CH(CH_2CH_2CH_2)$ |
| H | H | $CH_3$ | $CH_3$ | H | $CH_2CH_3$ | H | $CH_3$ | H | H | $CH(CH_2CH_2CH_2)$ |
| H | H | Cl | Cl | H | $CH_2CH_3$ | H | $CH_3$ | H | H | $CH(CH_2CH_2CH_2)$ |
| H | H | Br | Br | H | $CH_2CH_3$ | H | $CH_3$ | H | H | $CH(CH_2CH_2CH_2)$ |
| H | H | F | F | H | $CH_2CH_3$ | H | $CH_3$ | H | H | $CH(CH_2CH_2CH_2)$ |
| H | H | Cl | $CH_3$ | H | $CH_2CH_3$ | H | $CH_3$ | H | H | $CH(CH_2CH_2CH_2)$ |
| H | H | Br | $CH_3$ | H | $CH_2CH_3$ | H | $CH_3$ | H | H | $CH(CH_2CH_2CH_2)$ |
| H | H | F | $CH_3$ | H | $CH_2CH_3$ | H | $CH_3$ | H | H | $CH(CH_2CH_2CH_2)$ |
| H | H | $CH_3$ | Cl | H | $CH_2CH_3$ | H | $CH_3$ | H | H | $CH(CH_2CH_2CH_2)$ |
| H | H | $CH_3$ | Br | H | $CH_2CH_3$ | H | $CH_3$ | H | H | $CH(CH_2CH_2CH_2)$ |
| H | H | $CH_3$ | F | H | $CH_2CH_3$ | H | $CH_3$ | H | H | $CH(CH_2CH_2CH_2)$ |

Additional representative, non-limiting compounds of the present invention encompassed by Formula Ia are indicated below in Table 2, wherein $R_8$ is ethyl or propyl.

TABLE 2

Formula Ia

Representative compounds of Formula Ia

| $R_1$ | $R_2$ | $R_3$ | $R_4$ | $R_5$ | $R_8$ | $R_9$ | $R_{10}$ | $R_{11}$ |
|---|---|---|---|---|---|---|---|---|
| H | H | H | H | H | $C_2H_5$ | H | H | $C(CH_3)_3$ |
| H | Cl | H | H | H | $C_2H_5$ | H | H | $C(CH_3)_3$ |
| H | H | Cl | H | H | $C_2H_5$ | H | H | $C(CH_3)_3$ |
| H | H | H | Cl | H | $C_2H_5$ | H | H | $C(CH_3)_3$ |
| H | Br | H | H | H | $C_2H_5$ | H | H | $C(CH_3)_3$ |
| H | H | Br | H | H | $C_2H_5$ | H | H | $C(CH_3)_3$ |
| H | H | H | Br | H | $C_2H_5$ | H | H | $C(CH_3)_3$ |
| H | $CH_3$ | H | H | H | $C_2H_5$ | H | H | $C(CH_3)_3$ |
| H | H | $CH_3$ | H | H | $C_2H_5$ | H | H | $C(CH_3)_3$ |
| H | H | H | $CH_3$ | H | $C_2H_5$ | H | H | $C(CH_3)_3$ |
| H | F | H | H | H | $C_2H_5$ | H | H | $C(CH_3)_3$ |
| H | H | F | H | H | $C_2H_5$ | H | H | $C(CH_3)_3$ |
| H | H | H | F | H | $C_2H_5$ | H | H | $C(CH_3)_3$ |
| H | Cl | Cl | H | H | $C_2H_5$ | H | H | $C(CH_3)_3$ |
| H | Br | Br | H | H | $C_2H_5$ | H | H | $C(CH_3)_3$ |
| H | F | F | H | H | $C_2H_5$ | H | H | $C(CH_3)_3$ |
| H | $CH_3$ | $CH_3$ | H | H | $C_2H_5$ | H | H | $C(CH_3)_3$ |
| H | Cl | $CH_3$ | H | H | $C_2H_5$ | H | H | $C(CH_3)_3$ |
| H | Br | $CH_3$ | H | H | $C_2H_5$ | H | H | $C(CH_3)_3$ |
| H | F | $CH_3$ | H | H | $C_2H_5$ | H | H | $C(CH_3)_3$ |
| H | $CH_3$ | Cl | H | H | $C_2H_5$ | H | H | $C(CH_3)_3$ |
| H | $CH_3$ | Br | H | H | $C_2H_5$ | H | H | $C(CH_3)_3$ |
| H | $CH_3$ | F | H | H | $C_2H_5$ | H | H | $C(CH_3)_3$ |
| H | Cl | H | Cl | H | $C_2H_5$ | H | H | $C(CH_3)_3$ |
| H | Br | H | Br | H | $C_2H_5$ | H | H | $C(CH_3)_3$ |
| H | F | H | F | H | $C_2H_5$ | H | H | $C(CH_3)_3$ |
| H | $CH_3$ | H | $CH_3$ | H | $C_2H_5$ | H | H | $C(CH_3)_3$ |
| H | Cl | H | Cl | H | $C_2H_5$ | H | H | $C(CH_3)_3$ |
| H | Br | H | Br | H | $C_2H_5$ | H | H | $C(CH_3)_3$ |
| H | F | H | F | H | $C_2H_5$ | H | H | $C(CH_3)_3$ |
| H | H | $CH_3$ | $CH_3$ | H | $C_2H_5$ | H | H | $C(CH_3)_3$ |
| H | H | Cl | Cl | H | $C_2H_5$ | H | H | $C(CH_3)_3$ |
| H | H | Br | Br | H | $C_2H_5$ | H | H | $C(CH_3)_3$ |
| H | H | F | F | H | $C_2H_5$ | H | H | $C(CH_3)_3$ |
| H | H | Cl | $CH_3$ | H | $C_2H_5$ | H | H | $C(CH_3)_3$ |
| H | H | Br | $CH_3$ | H | $C_2H_5$ | H | H | $C(CH_3)_3$ |
| H | H | F | $CH_3$ | H | $C_2H_5$ | H | H | $C(CH_3)_3$ |
| H | H | $CH_3$ | Cl | H | $C_2H_5$ | H | H | $C(CH_3)_3$ |
| H | H | $CH_3$ | Br | H | $C_2H_5$ | H | H | $C(CH_3)_3$ |
| H | H | $CH_3$ | F | H | $C_2H_5$ | H | H | $C(CH_3)_3$ |
| H | H | H | H | H | $C_3H_7$ | H | H | $C(CH_3)_3$ |
| H | Cl | H | H | H | $C_3H_7$ | H | H | $C(CH_3)_3$ |
| H | H | Cl | H | H | $C_3H_7$ | H | H | $C(CH_3)_3$ |
| H | H | H | Cl | H | $C_3H_7$ | H | H | $C(CH_3)_3$ |
| H | Br | H | H | H | $C_3H_7$ | H | H | $C(CH_3)_3$ |
| H | H | Br | H | H | $C_3H_7$ | H | H | $C(CH_3)_3$ |
| H | H | H | Br | H | $C_3H_7$ | H | H | $C(CH_3)_3$ |
| H | $CH_3$ | H | H | H | $C_3H_7$ | H | H | $C(CH_3)_3$ |
| H | H | $CH_3$ | H | H | $C_3H_7$ | H | H | $C(CH_3)_3$ |
| H | H | H | $CH_3$ | H | $C_3H_7$ | H | H | $C(CH_3)_3$ |
| H | F | H | H | H | $C_3H_7$ | H | H | $C(CH_3)_3$ |
| H | H | F | H | H | $C_3H_7$ | H | H | $C(CH_3)_3$ |
| H | H | H | F | H | $C_3H_7$ | H | H | $C(CH_3)_3$ |
| H | Cl | Cl | H | H | $C_3H_7$ | H | H | $C(CH_3)_3$ |
| H | Br | Br | H | H | $C_3H_7$ | H | H | $C(CH_3)_3$ |
| H | F | F | H | H | $C_3H_7$ | H | H | $C(CH_3)_3$ |
| H | $CH_3$ | $CH_3$ | H | H | $C_3H_7$ | H | H | $C(CH_3)_3$ |
| H | Cl | $CH_3$ | H | H | $C_3H_7$ | H | H | $C(CH_3)_3$ |
| H | Br | $CH_3$ | H | H | $C_3H_7$ | H | H | $C(CH_3)_3$ |
| H | F | $CH_3$ | H | H | $C_3H_7$ | H | H | $C(CH_3)_3$ |
| H | $CH_3$ | Cl | H | H | $C_3H_7$ | H | H | $C(CH_3)_3$ |
| H | $CH_3$ | Br | H | H | $C_3H_7$ | H | H | $C(CH_3)_3$ |
| H | $CH_3$ | F | H | H | $C_3H_7$ | H | H | $C(CH_3)_3$ |
| H | Cl | H | Cl | H | $C_3H_7$ | H | H | $C(CH_3)_3$ |
| H | Br | H | Br | H | $C_3H_7$ | H | H | $C(CH_3)_3$ |
| H | F | H | F | H | $C_3H_7$ | H | H | $C(CH_3)_3$ |
| H | $CH_3$ | H | $CH_3$ | H | $C_3H_7$ | H | H | $C(CH_3)_3$ |
| H | Cl | H | Cl | H | $C_3H_7$ | H | H | $C(CH_3)_3$ |
| H | Br | H | Br | H | $C_3H_7$ | H | H | $C(CH_3)_3$ |
| H | F | H | F | H | $C_3H_7$ | H | H | $C(CH_3)_3$ |
| H | H | $CH_3$ | $CH_3$ | H | $C_3H_7$ | H | H | $C(CH_3)_3$ |
| H | H | Cl | Cl | H | $C_3H_7$ | H | H | $C(CH_3)_3$ |
| H | H | Br | Br | H | $C_3H_7$ | H | H | $C(CH_3)_3$ |
| H | H | F | F | H | $C_3H_7$ | H | H | $C(CH_3)_3$ |
| H | H | Cl | $CH_3$ | H | $C_3H_7$ | H | H | $C(CH_3)_3$ |
| H | H | Br | $CH_3$ | H | $C_3H_7$ | H | H | $C(CH_3)_3$ |
| H | H | F | $CH_3$ | H | $C_3H_7$ | H | H | $C(CH_3)_3$ |

TABLE 2-continued

Formula Ia

Representative compounds of Formula Ia

| $R_1$ | $R_2$ | $R_3$ | $R_4$ | $R_5$ | $R_8$ | $R_9$ | $R_{10}$ | $R_{11}$ |
|---|---|---|---|---|---|---|---|---|
| H | $CH_3$ | Cl | H | H | $C_3H_7$ | H | H | $C(CH_3)_3$ |
| H | $CH_3$ | Br | H | H | $C_3H_7$ | H | H | $C(CH_3)_3$ |
| H | $CH_3$ | F | H | H | $C_3H_7$ | H | H | $C(CH_3)_3$ |
| H | Cl | H | Cl | H | $C_3H_7$ | H | H | $C(CH_3)_3$ |
| H | Br | H | Br | H | $C_3H_7$ | H | H | $C(CH_3)_3$ |
| H | F | H | H | H | $C_3H_7$ | H | H | $C(CH_3)_3$ |
| H | $CH_3$ | H | $CH_3$ | H | $C_3H_7$ | H | H | $C(CH_3)_3$ |
| H | Cl | H | Cl | H | $C_3H_7$ | H | H | $C(CH_3)_3$ |
| H | Br | H | Br | H | $C_3H_7$ | H | H | $C(CH_3)_3$ |
| H | F | H | F | H | $C_3H_7$ | H | H | $C(CH_3)_3$ |
| H | H | $CH_3$ | $CH_3$ | H | $C_3H_7$ | H | H | $C(CH_3)_3$ |
| H | H | Cl | Cl | H | $C_3H_7$ | H | H | $C(CH_3)_3$ |
| H | H | Br | Br | H | $C_3H_7$ | H | H | $C(CH_3)_3$ |
| H | H | F | F | H | $C_3H_7$ | H | H | $C(CH_3)_3$ |
| H | H | Cl | $CH_3$ | H | $C_3H_7$ | H | H | $C(CH_3)_3$ |
| H | H | Br | $CH_3$ | H | $C_3H_7$ | H | H | $C(CH_3)_3$ |
| H | H | F | $CH_3$ | H | $C_3H_7$ | H | H | $C(CH_3)_3$ |
| H | H | $CH_3$ | Cl | H | $C_3H_7$ | H | H | $C(CH_3)_3$ |
| H | H | $CH_3$ | Br | H | $C_3H_7$ | H | H | $C(CH_3)_3$ |
| H | H | $CH_3$ | F | H | $C_3H_7$ | H | H | $C(CH_3)_3$ |
| H | H | H | H | H | $C_2H_5$ | H | H | $CH(CH_2CH_2CH_2)$ |
| H | Cl | H | H | H | $C_2H_5$ | H | H | $CH(CH_2CH_2CH_2)$ |
| H | H | Cl | H | H | $C_2H_5$ | H | H | $CH(CH_2CH_2CH_2)$ |
| H | H | H | Cl | H | $C_2H_5$ | H | H | $CH(CH_2CH_2CH_2)$ |
| H | Br | H | H | H | $C_2H_5$ | H | H | $CH(CH_2CH_2CH_2)$ |
| H | H | Br | H | H | $C_2H_5$ | H | H | $CH(CH_2CH_2CH_2)$ |
| H | H | H | Br | H | $C_2H_5$ | H | H | $CH(CH_2CH_2CH_2)$ |
| H | $CH_3$ | H | H | H | $C_2H_5$ | H | H | $CH(CH_2CH_2CH_2)$ |
| H | H | $CH_3$ | H | H | $C_2H_5$ | H | H | $CH(CH_2CH_2CH_2)$ |
| H | H | H | $CH_3$ | H | $C_2H_5$ | H | H | $CH(CH_2CH_2CH_2)$ |
| H | F | H | H | H | $C_2H_5$ | H | H | $CH(CH_2CH_2CH_2)$ |
| H | H | F | H | H | $C_2H_5$ | H | H | $CH(CH_2CH_2CH_2)$ |
| H | H | H | F | H | $C_2H_5$ | H | H | $CH(CH_2CH_2CH_2)$ |
| H | Cl | Cl | H | H | $C_2H_5$ | H | H | $CH(CH_2CH_2CH_2)$ |
| H | Br | Br | H | H | $C_2H_5$ | H | H | $CH(CH_2CH_2CH_2)$ |
| H | F | F | H | H | $C_2H_5$ | H | H | $CH(CH_2CH_2CH_2)$ |
| H | $CH_3$ | $CH_3$ | H | H | $C_2H_5$ | H | H | $CH(CH_2CH_2CH_2)$ |
| H | Cl | $CH_3$ | H | H | $C_2H_5$ | H | H | $CH(CH_2CH_2CH_2)$ |
| H | Br | $CH_3$ | H | H | $C_2H_5$ | H | H | $CH(CH_2CH_2CH_2)$ |
| H | F | $CH_3$ | H | H | $C_2H_5$ | H | H | $CH(CH_2CH_2CH_2)$ |
| H | $CH_3$ | Cl | H | H | $C_2H_5$ | H | H | $CH(CH_2CH_2CH_2)$ |
| H | $CH_3$ | Br | H | H | $C_2H_5$ | H | H | $CH(CH_2CH_2CH_2)$ |
| H | $CH_3$ | F | H | H | $C_2H_5$ | H | H | $CH(CH_2CH_2CH_2)$ |
| H | Cl | H | Cl | H | $C_2H_5$ | H | H | $CH(CH_2CH_2CH_2)$ |
| H | Br | H | Br | H | $C_2H_5$ | H | H | $CH(CH_2CH_2CH_2)$ |
| H | F | H | F | H | $C_2H_5$ | H | H | $CH(CH_2CH_2CH_2)$ |
| H | $CH_3$ | H | $CH_3$ | H | $C_2H_5$ | H | H | $CH(CH_2CH_2CH_2)$ |
| H | Cl | H | Cl | H | $C_2H_5$ | H | H | $CH(CH_2CH_2CH_2)$ |
| H | Br | H | Br | H | $C_2H_5$ | H | H | $CH(CH_2CH_2CH_2)$ |
| H | F | H | F | H | $C_2H_5$ | H | H | $CH(CH_2CH_2CH_2)$ |
| H | H | $CH_3$ | $CH_3$ | H | $C_2H_5$ | H | H | $CH(CH_2CH_2CH_2)$ |
| H | H | Cl | Cl | H | $C_2H_5$ | H | H | $CH(CH_2CH_2CH_2)$ |
| H | H | Br | Br | H | $C_2H_5$ | H | H | $CH(CH_2CH_2CH_2)$ |
| H | H | F | F | H | $C_2H_5$ | H | H | $CH(CH_2CH_2CH_2)$ |
| H | H | Cl | $CH_3$ | H | $C_2H_5$ | H | H | $CH(CH_2CH_2CH_2)$ |
| H | H | Br | $CH_3$ | H | $C_2H_5$ | H | H | $CH(CH_2CH_2CH_2)$ |
| H | H | F | $CH_3$ | H | $C_2H_5$ | H | H | $CH(CH_2CH_2CH_2)$ |
| H | H | $CH_3$ | Cl | H | $C_2H_5$ | H | H | $CH(CH_2CH_2CH_2)$ |
| H | H | $CH_3$ | Br | H | $C_2H_5$ | H | H | $CH(CH_2CH_2CH_2)$ |
| H | H | $CH_3$ | F | H | $C_2H_5$ | H | H | $CH(CH_2CH_2CH_2)$ |
| H | H | H | H | H | $C_3H_7$ | H | H | $CH(CH_2CH_2CH_2)$ |
| H | Cl | H | H | H | $C_3H_7$ | H | H | $CH(CH_2CH_2CH_2)$ |
| H | H | Cl | H | H | $C_3H_7$ | H | H | $CH(CH_2CH_2CH_2)$ |
| H | H | H | Cl | H | $C_3H_7$ | H | H | $CH(CH_2CH_2CH_2)$ |
| H | Br | H | H | H | $C_3H_7$ | H | H | $CH(CH_2CH_2CH_2)$ |

TABLE 2-continued

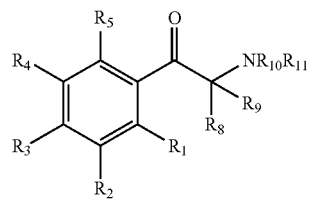

Formula Ia

Representative compounds of Formula Ia

| R$_1$ | R$_2$ | R$_3$ | R$_4$ | R$_5$ | R$_8$ | R$_9$ | R$_{10}$ | R$_{11}$ |
|---|---|---|---|---|---|---|---|---|
| H | H | Br | H | H | C$_3$H$_7$ | H | H | CH(CH$_2$CH$_2$CH$_2$) |
| H | H | H | Br | H | C$_3$H$_7$ | H | H | CH(CH$_2$CH$_2$CH$_2$) |
| H | CH$_3$ | H | H | H | C$_3$H$_7$ | H | H | CH(CH$_2$CH$_2$CH$_2$) |
| H | H | CH$_3$ | H | H | C$_3$H$_7$ | H | H | CH(CH$_2$CH$_2$CH$_2$) |
| H | H | H | CH$_3$ | H | C$_3$H$_7$ | H | H | CH(CH$_2$CH$_2$CH$_2$) |
| H | F | H | H | H | C$_3$H$_7$ | H | H | CH(CH$_2$CH$_2$CH$_2$) |
| H | H | F | H | H | C$_3$H$_7$ | H | H | CH(CH$_2$CH$_2$CH$_2$) |
| H | H | H | F | H | C$_3$H$_7$ | H | H | CH(CH$_2$CH$_2$CH$_2$) |
| H | Cl | Cl | H | H | C$_3$H$_7$ | H | H | CH(CH$_2$CH$_2$CH$_2$) |
| H | Br | Br | H | H | C$_3$H$_7$ | H | H | CH(CH$_2$CH$_2$CH$_2$) |
| H | F | F | H | H | C$_3$H$_7$ | H | H | CH(CH$_2$CH$_2$CH$_2$) |
| H | CH$_3$ | CH$_3$ | H | H | C$_3$H$_7$ | H | H | CH(CH$_2$CH$_2$CH$_2$) |
| H | Cl | CH$_3$ | H | H | C$_3$H$_7$ | H | H | CH(CH$_2$CH$_2$CH$_2$) |
| H | Br | CH$_3$ | H | H | C$_3$H$_7$ | H | H | CH(CH$_2$CH$_2$CH$_2$) |
| H | F | CH$_3$ | H | H | C$_3$H$_7$ | H | H | CH(CH$_2$CH$_2$CH$_2$) |
| H | CH$_3$ | Cl | H | H | C$_3$H$_7$ | H | H | CH(CH$_2$CH$_2$CH$_2$) |
| H | CH$_3$ | Br | H | H | C$_3$H$_7$ | H | H | CH(CH$_2$CH$_2$CH$_2$) |
| H | CH$_3$ | F | H | H | C$_3$H$_7$ | H | H | CH(CH$_2$CH$_2$CH$_2$) |
| H | Cl | H | Cl | H | C$_3$H$_7$ | H | H | CH(CH$_2$CH$_2$CH$_2$) |
| H | Br | H | Br | H | C$_3$H$_7$ | H | H | CH(CH$_2$CH$_2$CH$_2$) |
| H | F | H | F | H | C$_3$H$_7$ | H | H | CH(CH$_2$CH$_2$CH$_2$) |
| H | CH$_3$ | H | CH$_3$ | H | C$_3$H$_7$ | H | H | CH(CH$_2$CH$_2$CH$_2$) |
| H | Cl | H | Cl | H | C$_3$H$_7$ | H | H | CH(CH$_2$CH$_2$CH$_2$) |
| H | Br | H | Br | H | C$_3$H$_7$ | H | H | CH(CH$_2$CH$_2$CH$_2$) |
| H | F | H | F | H | C$_3$H$_7$ | H | H | CH(CH$_2$CH$_2$CH$_2$) |
| H | H | CH$_3$ | CH$_3$ | H | C$_3$H$_7$ | H | H | CH(CH$_2$CH$_2$CH$_2$) |
| H | H | Cl | Cl | H | C$_3$H$_7$ | H | H | CH(CH$_2$CH$_2$CH$_2$) |
| H | H | Br | Br | H | C$_3$H$_7$ | H | H | CH(CH$_2$CH$_2$CH$_2$) |
| H | H | F | F | H | C$_3$H$_7$ | H | H | CH(CH$_2$CH$_2$CH$_2$) |
| H | H | Cl | CH$_3$ | H | C$_3$H$_7$ | H | H | CH(CH$_2$CH$_2$CH$_2$) |
| H | H | Br | CH$_3$ | H | C$_3$H$_7$ | H | H | CH(CH$_2$CH$_2$CH$_2$) |
| H | H | F | CH$_3$ | H | C$_3$H$_7$ | H | H | CH(CH$_2$CH$_2$CH$_2$) |
| H | H | CH$_3$ | Cl | H | C$_3$H$_7$ | H | H | CH(CH$_2$CH$_2$CH$_2$) |
| H | H | CH$_3$ | Br | H | C$_3$H$_7$ | H | H | CH(CH$_2$CH$_2$CH$_2$) |
| H | H | CH$_3$ | F | H | C$_3$H$_7$ | H | H | CH(CH$_2$CH$_2$CH$_2$) |

Representative, non-limiting compounds of Formula Ib of the present invention are indicated below in Table 3.

TABLE 3

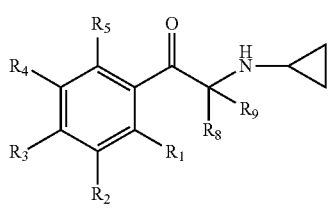

Formula Ib

Representative compounds of Formula Ib

| R$_1$ | R$_2$ | R$_3$ | R$_4$ | R$_5$ | R$_8$ | R$_9$ |
|---|---|---|---|---|---|---|
| H | H | H | H | H | CH$_3$ | H |
| H | Cl | H | H | H | CH$_3$ | H |
| H | H | Cl | H | H | CH$_3$ | H |
| H | H | H | Cl | H | CH$_3$ | H |
| H | Br | H | H | H | CH$_3$ | H |
| H | H | Br | H | H | CH$_3$ | H |
| H | H | H | Br | H | CH$_3$ | H |

TABLE 3-continued

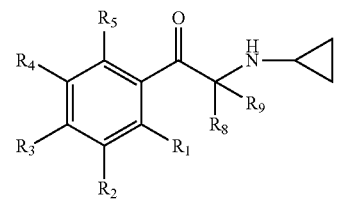

Formula Ib

Representative compounds of Formula Ib

| R$_1$ | R$_2$ | R$_3$ | R$_4$ | R$_5$ | R$_8$ | R$_9$ |
|---|---|---|---|---|---|---|
| H | CH$_3$ | H | H | H | CH$_3$ | H |
| H | H | CH$_3$ | H | H | CH$_3$ | H |
| H | H | H | CH$_3$ | H | CH$_3$ | H |
| H | F | H | H | H | CH$_3$ | H |
| H | H | F | H | H | CH$_3$ | H |
| H | H | H | F | H | CH$_3$ | H |
| H | Cl | Cl | H | H | CH$_3$ | H |
| H | Br | Br | H | H | CH$_3$ | H |
| H | F | F | H | H | CH$_3$ | H |
| H | CH$_3$ | CH$_3$ | H | H | CH$_3$ | H |
| H | Cl | CH$_3$ | H | H | CH$_3$ | H |
| H | Br | CH$_3$ | H | H | CH$_3$ | H |
| H | F | CH$_3$ | H | H | CH$_3$ | H |
| H | CH$_3$ | Cl | H | H | CH$_3$ | H |
| H | CH$_3$ | Br | H | H | CH$_3$ | H |
| H | CH$_3$ | F | H | H | CH$_3$ | H |
| H | Cl | H | Cl | H | CH$_3$ | H |
| H | Br | H | Br | H | CH$_3$ | H |
| H | F | H | F | H | CH$_3$ | H |
| H | CH$_3$ | H | CH$_3$ | H | CH$_3$ | H |
| H | Cl | H | Cl | H | CH$_3$ | H |
| H | Br | H | Br | H | CH$_3$ | H |
| H | F | H | F | H | CH$_3$ | H |
| H | H | CH$_3$ | CH$_3$ | H | CH$_3$ | H |
| H | H | Cl | Cl | H | CH$_3$ | H |
| H | H | Br | Br | H | CH$_3$ | H |
| H | H | F | F | H | CH$_3$ | H |
| H | H | Cl | CH$_3$ | H | CH$_3$ | H |
| H | H | Br | CH$_3$ | H | CH$_3$ | H |
| H | H | F | CH$_3$ | H | CH$_3$ | H |
| H | H | CH$_3$ | Cl | H | CH$_3$ | H |
| H | H | CH$_3$ | Br | H | CH$_3$ | H |
| H | H | CH$_3$ | F | H | CH$_3$ | H |
| H | H | H | H | H | C$_2$H$_5$ | H |
| H | Cl | H | H | H | C$_2$H$_5$ | H |
| H | H | Cl | H | H | C$_2$H$_5$ | H |
| H | H | H | Cl | H | C$_2$H$_5$ | H |
| H | Br | H | H | H | C$_2$H$_5$ | H |
| H | H | Br | H | H | C$_2$H$_5$ | H |
| H | H | H | Br | H | C$_2$H$_5$ | H |
| H | CH$_3$ | H | H | H | C$_2$H$_5$ | H |
| H | H | CH$_3$ | H | H | C$_2$H$_5$ | H |
| H | H | H | CH$_3$ | H | C$_2$H$_5$ | H |
| H | F | H | H | H | C$_2$H$_5$ | H |
| H | H | F | H | H | C$_2$H$_5$ | H |
| H | H | H | F | H | C$_2$H$_5$ | H |
| H | Cl | Cl | H | H | C$_2$H$_5$ | H |
| H | Br | Br | H | H | C$_2$H$_5$ | H |
| H | F | F | H | H | C$_2$H$_5$ | H |
| H | CH$_3$ | CH$_3$ | H | H | C$_2$H$_5$ | H |
| H | Cl | CH$_3$ | H | H | C$_2$H$_5$ | H |
| H | Br | CH$_3$ | H | H | C$_2$H$_5$ | H |
| H | F | CH$_3$ | H | H | C$_2$H$_5$ | H |
| H | CH$_3$ | Cl | H | H | C$_2$H$_5$ | H |
| H | CH$_3$ | Br | H | H | C$_2$H$_5$ | H |
| H | CH$_3$ | F | H | H | C$_2$H$_5$ | H |
| H | Cl | H | Cl | H | C$_2$H$_5$ | H |
| H | Br | H | Br | H | C$_2$H$_5$ | H |
| H | F | H | F | H | C$_2$H$_5$ | H |
| H | CH$_3$ | H | CH$_3$ | H | C$_2$H$_5$ | H |
| H | Cl | H | Cl | H | C$_2$H$_5$ | H |
| H | Br | H | Br | H | C$_2$H$_5$ | H |
| H | F | H | F | H | C$_2$H$_5$ | H |
| H | H | CH$_3$ | CH$_3$ | H | C$_2$H$_5$ | H |
| H | H | Cl | Cl | H | C$_2$H$_5$ | H |

TABLE 3-continued

Formula Ib

Representative compounds of Formula Ib

| R₁ | R₂ | R₃ | R₄ | R₅ | R₈ | R₉ |
|---|---|---|---|---|---|---|
| H | H | Br | Br | H | C₂H₅ | H |
| H | H | F | F | H | C₂H₅ | H |
| H | H | Cl | CH₃ | H | C₂H₅ | H |
| H | H | Br | CH₃ | H | C₂H₅ | H |
| H | H | F | CH₃ | H | C₂H₅ | H |
| H | H | CH₃ | Cl | H | C₂H₅ | H |
| H | H | CH₃ | Br | H | C₂H₅ | H |
| H | H | CH₃ | F | H | C₂H₅ | H |
| H | H | H | H | H | C₃H₇ | H |
| H | Cl | H | H | H | C₃H₇ | H |
| H | H | Cl | H | H | C₃H₇ | H |
| H | H | H | Cl | H | C₃H₇ | H |
| H | Br | H | H | H | C₃H₇ | H |
| H | H | Br | H | H | C₃H₇ | H |
| H | H | H | Br | H | C₃H₇ | H |
| H | CH₃ | H | H | H | C₃H₇ | H |
| H | H | CH₃ | H | H | C₃H₇ | H |
| H | H | H | CH₃ | H | C₃H₇ | H |
| H | F | H | H | H | C₃H₇ | H |
| H | H | F | H | H | C₃H₇ | H |
| H | H | H | F | H | C₃H₇ | H |
| H | Cl | Cl | H | H | C₃H₇ | H |
| H | Br | Br | H | H | C₃H₇ | H |
| H | F | F | H | H | C₃H₇ | H |
| H | CH₃ | CH₃ | H | H | C₃H₇ | H |
| H | Cl | CH₃ | H | H | C₃H₇ | H |
| H | Br | CH₃ | H | H | C₃H₇ | H |
| H | F | CH₃ | H | H | C₃H₇ | H |
| H | CH₃ | Cl | H | H | C₃H₇ | H |
| H | CH₃ | Br | H | H | C₃H₇ | H |
| H | CH₃ | F | H | H | C₃H₇ | H |
| H | Cl | H | Cl | H | C₃H₇ | H |
| H | Br | H | Br | H | C₃H₇ | H |
| H | F | H | F | H | C₃H₇ | H |
| H | CH₃ | H | CH₃ | H | C₃H₇ | H |
| H | Cl | H | Cl | H | C₃H₇ | H |
| H | Br | H | Br | H | C₃H₇ | H |
| H | F | H | F | H | C₃H₇ | H |
| H | H | CH₃ | CH₃ | H | C₃H₇ | H |
| H | H | Cl | Cl | H | C₃H₇ | H |
| H | H | Br | Br | H | C₃H₇ | H |
| H | H | F | F | H | C₃H₇ | H |
| H | H | Cl | CH₃ | H | C₃H₇ | H |
| H | H | Br | CH₃ | H | C₃H₇ | H |
| H | H | F | CH₃ | H | C₃H₇ | H |
| H | H | CH₃ | Cl | H | C₃H₇ | H |
| H | H | CH₃ | Br | H | C₃H₇ | H |
| H | H | CH₃ | F | H | C₃H₇ | H |

In particular embodiments, the compounds of the present invention are compounds of Formula Ia, which include one or more of the following: an alkyl group alpha to the ketone, one or more substituents on the phenyl ring, and/or one or more alkyl substituents on the amine. Such compounds may show enhanced activity in monoamine transporter binding properties and may effectively inhibit monoamine uptake.

Methods of Preparation

The present invention also encompasses methods of preparing compounds with structures encompassed by Formula I, Formula Ia, and/or Formula Ib. Scheme 1 shows a general synthesis used for some compounds represented by Formula Ia of the present invention. In general, the original procedure used to prepare bupropion and modified by Chenard and co-workers was followed. See Mehta, N. B., The Chemistry of Bupropion, *J. Clin. Psychiat.* 1983, 45, (5 (sec. 2)), 56-59 and Chenard, B L. et al., (1S,2S)-1-(4-Hydroxyphenyl)-2-(4-hydroxy-4-phenylpiperidino)-1-propanol: A Potent New Neuroprotectant Which Blocks N-methyl-D-aspartate Responses, *J. Med. Chem.* 1995, 38, 3138-3145, both of which are incorporated by reference herein. Briefly, a benzonitrile is converted to a substituted phenone, which is brominated at the carbon alpha to the carbonyl to form a bromo intermediate, which can then be reacted with an amine by nucleophilic substitution to form the amine. One of skill in the art would be able to adapt this method as required to accommodate various functional groups that may affect the chemistry of the synthesis.

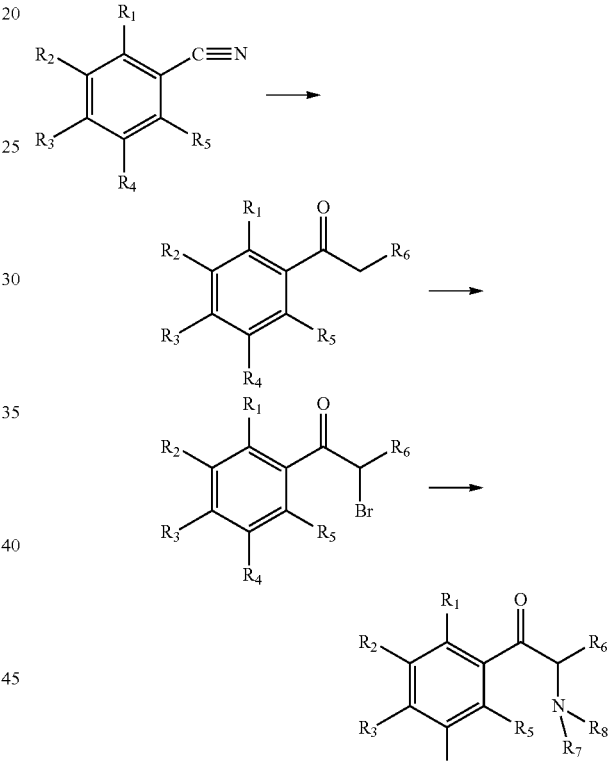

Scheme 1

Compositions

While it is possible for the compounds of the present invention to be administered in the raw chemical form, it is preferred for the compounds to be delivered as a pharmaceutical formulation. Accordingly, there are provided by the present invention pharmaceutical compositions comprising at least one compound capable of inhibiting the reuptake of one or more monoamines. As such, the formulations of the present invention comprise a compound of Formula I, as described above, or a pharmaceutically acceptable ester, amide, salt, or solvate thereof, together with one or more pharmaceutically acceptable carriers therefore, and optionally, other therapeutic ingredients.

By "pharmaceutically acceptable carrier" is intended a carrier that is conventionally used in the art to facilitate the storage, administration, and/or the healing effect of the agent. The carrier(s) must be pharmaceutically acceptable in the sense of being compatible with the other ingredients of the formulation and not unduly deleterious to the recipient thereof. A carrier may also reduce any undesirable side effects of the agent. Such carriers are known in the art. See, Wang et al. (1980) *J. Parent Drug Assn.* 34(6):452-462, herein incorporated by reference in its entirety.

Adjuvants or accessory ingredients for use in the formulations of the present invention can include any pharmaceutical ingredient commonly deemed acceptable in the art, such as binders, fillers, lubricants, disintegrants, diluents, surfactants, stabilizers, preservatives, flavoring and coloring agents, and the like. The compositions may further include diluents, buffers, binders, disintegrants, thickeners, lubricants, preservatives (including antioxidants), flavoring agents, taste-masking agents, inorganic salts (e.g., sodium chloride), antimicrobial agents (e.g., benzalkonium chloride), sweeteners, antistatic agents, surfactants (e.g., polysorbates such as "TWEEN 20" and "TWEEN 80", and pluronics such as F68 and F88, available from BASF), sorbitan esters, lipids (e.g., phospholipids such as lecithin and other phosphatidylcholines, phosphatidylethanolamines, fatty acids and fatty esters, steroids (e.g., cholesterol)), and chelating agents (e.g., EDTA, zinc and other such suitable cations). Other pharmaceutical excipients and/or additives suitable for use in the compositions according to the invention are listed in "Remington: The Science & Practice of Pharmacy," $19^{th}$ ed., Williams & Williams, (1995), in the "Physician's Desk Reference," $52^{nd}$ ed., Medical Economics, Montvale, N.J. (1998), and in "Handbook of Pharmaceutical Excipients," Third Ed., Ed. A. H. Kibbe, Pharmaceutical Press, 2000.

Binders are generally used to facilitate cohesiveness of the tablet and ensure the tablet remains intact after compression. Suitable binders include, but are not limited to: starch, polysaccharides, gelatin, polyethylene glycol, propylene glycol, waxes, and natural and synthetic gums. Acceptable fillers include silicon dioxide, titanium dioxide, alumina, talc, kaolin, powdered cellulose, and microcrystalline cellulose, as well as soluble materials, such as mannitol, urea, sucrose, lactose, dextrose, sodium chloride, and sorbitol. Lubricants are useful for facilitating tablet manufacture and include vegetable oils, glycerin, magnesium stearate, calcium stearate, and stearic acid. Disintegrants, which are useful for facilitating disintegration of the tablet, generally include starches, clays, celluoses, algins, gums, and crosslinked polymers. Diluents, which are generally included to provide bulk to the tablet, may include dicalcium phosphate, calcium sulfate, lactose, cellulose, kaolin, mannitol, sodium chloride, dry starch, and powdered sugar. Surfactants suitable for use in the formulation according to the present invention may be anionic, cationic, amphoteric, or nonionic surface active agents. Stabilizers may be included in the formulations to inhibit or lessen reactions leading to decomposition of the active agent, such as oxidative reactions.

Formulations of the present invention may include short-term, rapid-onset, rapid-offset, controlled release, sustained release, delayed release, and pulsatile release formulations, providing the formulations achieve administration of a compound as described herein. See *Remington's Pharmaceutical Sciences* ($18^{th}$ ed.; Mack Publishing Company, Eaton, Pa., 1990), herein incorporated by reference in its entirety.

Pharmaceutical formulations according to the present invention are suitable for various modes of delivery, including oral, parenteral (including intravenous, intramuscular, subcutaneous, intradermal, and transdermal), topical (including dermal, buccal, and sublingual), and rectal administration. The most useful and/or beneficial mode of administration can vary, especially depending upon the condition of the recipient and the disorder being treated.

The pharmaceutical formulations may be conveniently made available in a unit dosage form, whereby such formulations may be prepared by any of the methods generally known in the pharmaceutical arts. Generally speaking, such methods of preparation comprise combining (by various methods) an active agent, such as the compounds of Formula I according to the present invention (or a pharmaceutically acceptable ester, amide, salt, or solvate thereof) with a suitable carrier or other adjuvant, which may consist of one or more ingredients. The combination of the active ingredient with the one or more adjuvants is then physically treated to present the formulation in a suitable form for delivery (e.g., shaping into a tablet or forming an aqueous suspension).

Pharmaceutical formulations according to the present invention suitable as oral dosage may take various foul's, such as tablets, capsules, caplets, and wafers (including rapidly dissolving or effervescing), each containing a predetermined amount of the active agent. The formulations may also be in the form of a powder or granules, a solution or suspension in an aqueous or non-aqueous liquid, and as a liquid emulsion (oil-in-water and water-in-oil). The active agent may also be delivered as a bolus, electuary, or paste. It is generally understood that methods of preparations of the above dosage forms are generally known in the art, and any such method would be suitable for the preparation of the respective dosage forms for use in delivery of the compounds according to the present invention.

A tablet containing a compound according to the present invention may be manufactured by any standard process readily known to one of skill in the art, such as, for example, by compression or molding, optionally with one or more adjuvant or accessory ingredient. The tablets may optionally be coated or scored and may be formulated so as to provide slow or controlled release of the active agent.

Solid dosage forms may be formulated so as to provide a delayed release of the active agent, such as by application of a coating. Delayed release coatings are known in the art, and dosage forms containing such may be prepared by any known suitable method. Such methods generally include that, after preparation of the solid dosage form (e.g., a tablet or caplet), a delayed release coating composition is applied. Application can be by methods, such as airless spraying, fluidized bed coating, use of a coating pan, or the like. Materials for use as a delayed release coating can be polymeric in nature, such as cellulosic material (e.g., cellulose butyrate phthalate, hydroxypropyl methylcellulose phthalate, and carboxymethyl ethylcellulose), and polymers and copolymers of acrylic acid, methacrylic acid, and esters thereof.

Solid dosage forms according to the present invention may also be sustained release (i.e., releasing the active agent over a prolonged period of time), and may or may not also be delayed release. Sustained release formulations are known in the art and are generally prepared by dispersing a drug within a matrix of a gradually degradable or hydrolyzable material, such as an insoluble plastic, a hydrophilic polymer, or a fatty compound. Alternatively, a solid dosage form may be coated with such a material.

Formulations for parenteral administration include aqueous and non-aqueous sterile injection solutions, which may further contain additional agents, such as anti-oxidants, buffers, bacteriostats, and solutes, which render the formulations isotonic with the blood of the intended recipient. The formulations may include aqueous and non-aqueous sterile suspensions, which contain suspending agents and thickening agents. Such formulations for patenteral administration may be presented in unit-dose or multi-dose containers, such as, for example, sealed ampoules and viles, and may be stores in a freeze-dried (lyophilized) condition requiring only the addition of the sterile liquid carrier, for example, water (for injection), immediately prior to use. Extemporaneous injection solutions and suspensions may be prepared from sterile powders, granules, and tablets of the kind previously described.

The compounds according to the present invention may also be administered transdermally, wherein the active agent is incorporated into a laminated structure (generally referred to as a "patch") that is adapted to remain in intimate contact with the epidermis of the recipient for a prolonged period of time. Typically, such patches are available as single layer "drug-in-adhesive" patches or as multi-layer patches where the active agent is contained in a layer separate from the adhesive layer. Both types of patches also generally contain a backing layer and a liner that is removed prior to attachment to the skin of the recipient. Transdermal drug delivery patches may also be comprised of a reservoir underlying the backing layer that is separated from the skin of the recipient by a semi-permeable membrane and adhesive layer. Transdermal drug delivery may occur through passive diffusion or may be facilitated using electrotransport or iontophoresis.

Formulations for rectal delivery of the compounds of the present invention include rectal suppositories, creams, ointments, and liquids. Suppositories may be presented as the active agent in combination with a carrier generally known in the art, such as polyethylene glycol. Such dosage forms may be designed to disintegrate rapidly or over an extended period of time, and the time to complete disintegration can range from a short time, such as about 10 minutes, to an extended period of time, such as about 6 hours.

The compounds of Formula I above may be formulated in compositions including those suitable for oral, buccal, rectal, topical, nasal, ophthalmic, or parenteral (including intraperitoneal, intravenous, subcutaneous, or intramuscular injection) administration. The compositions may conveniently be presented in unit dosage form and may be prepared by any of the methods well known in the art of pharmacy. All methods include the step of bringing a compound of Formula I into association with a carrier that constitutes one or more accessory ingredients. In general, the compositions are prepared by bringing a compound of the invention into association with a liquid carrier to form a solution or a suspension, or alternatively, bringing a compound of the invention into association with formulation components suitable for forming a solid, optionally a particulate product, and then, if warranted, shaping the product into a desired delivery form. Solid formulations of the invention, when particulate, will typically comprise particles with sizes ranging from about 1 nanometer to about 500 microns. In general, for solid formulations intended for intravenous administration, particles will typically range from about 1 nm to about 10 microns in diameter.

The amount of the compound of Formula I in the formulation will vary depending the specific compound selected, dosage form, target patient population, and other considerations, and will be readily determined by one skilled in the art. The amount of the compound of Formula I in the formulation will be that amount necessary to deliver a therapeutically effective amount of the compound to a patient in need thereof to achieve at least one of the therapeutic effects associated with the compounds of the invention. In practice, this will vary widely depending upon the particular compound, its activity, the severity of the condition to be treated, the patient population, the stability of the formulation, and the like. Compositions will generally contain anywhere from about 1% by weight to about 99% by weight of a compound of the invention, typically from about 5% to about 70% by weight, and more typically from about 10% to about 50% by weight, and will also depend upon the relative amounts of excipients/additives contained in the composition.

Combinations

In specific embodiments, active agents used in combination with compounds of the present invention comprise one or more compounds generally recognized as useful for treating the conditions discussed herein. For example, in certain embodiments, the present invention provides a method for treating depression comprising administering a combination of a compound of the present invention and one or more known antidepressants. Antidepressants useful according to the invention comprise selective serotonin reuptake inhibitors (SSRIs), tricyclics, serotonin norepinephrine reuptake inhibitors (5-HT-NE dual reuptake inhibitors), and norepinephrine and dopamine reuptake inhibitors (NDRIs).

In one embodiment, compounds of Formula I may be combined with one or more compounds that are serotonin reuptake inhibitors. Serotonin reuptake inhibitors increase the extracellular level of the serotonin by inhibiting its reuptake into the presynaptic cell, which increases the level of serotonin available to bind to and stimulate the postsynaptic receptor. A significant percentage of bupropion use currently occurs in combination with one or more antidepressant drugs, most commonly by combining bupropion with one or more SSRIs. Examples of SSRIs include fluoxetine (PROZAC®) paroxetine (PAXIL®), sertraline (ZOLOFT®), citalopram (CELEXA®), escitalopram (LEXAPRO®), nefazodone (SERZONE®) and fluvoxamine (LUVOX®).

In another embodiment, compounds of Formula I may be combined with one or more compounds that at least partially inhibit the function of monoamine oxidase. Monoamine oxidase inhibitors (MAOIs) comprise a class of compounds understood to act by inhibiting the activity of monoamine oxidase, an enzyme generally found in the brain and liver of the human body, which functions to break down monoamine compounds, typically through deamination. There are two isoforms of monoamine oxidase inhibitors, MAO-A and MAO-B. The MAO-A isoform preferentially deaminates monoamines typically occurring as neurotransmitters (e.g., serotonin, melatonin, epinephrine, norepinephrine, and dopamine). Thus, MAOIs have been historically prescribed as antidepressants and for treatment of other social disorders, such as agoraphobia and social anxiety. The MAO-B isoform preferentially deaminates phenylethylamine and trace amines. Dopamine is equally deaminated by both isoforms. MAOIs may by reversible or non-reversible and may be selective for a specific isoform. For example, the MAOI moclobemide (also known as Manerix or Aurorix) is known to be approximately three times more selective for MAO-A than MAO-B.

Any compound generally recognized as being an MAOI may be useful according to the present invention. Non-limiting examples of MAOIs useful in combination with compounds of the present invention for preparing compositions according to the invention include the following: isocarboxazid (MARPLAN®); moclobemide (Aurorix, Manerix, or Moclodura); phenelzine (NARDIL®); tranylcypromine (PARNATE®); selegiline (ELDEPRYL®, EMSAM®, or 1-deprenyl); lazabemide; nialamide; iproniazid (marsilid, iprozid, iprozid, rivivol, or propilniazida); iproclozide; toloxatone; harmala; brofaromine (Consonar); benmoxin (Neuralex); and certain tryptamines, such as 5-MeO-DMT (5-Methoxy-N,N-dimethyltryptamine) or 5-MeO-AMT (5-methoxy-α-methyltryptamine).

According to still another embodiment of the invention, compounds of Formula I may be combined with one or more compounds that is a norepinephrine reuptake inhibitor (NRI). NRIs are also known as noradrenaline reuptake inhibitors (NARIs) and generally function to elevate the level of norepinephrine in the central nervous system (CNS) by inhibiting reuptake of norepinephrine from the synaptic cleft into the presynaptic neuronal terminal Norepinephrine is a catecholamine and phenylethylamine that functions as a neurotransmitter and is known to affect many conditions. Any compound typically recognized as inhibiting the reuptake of norepinephrine in the CNS can be used according to the present invention. Non-limiting examples of NRIs useful according to the invention comprise atomoxetine (STRATTERA®), reboxetine (EDRONAX®, VESTRA®, or NOREBOX®), viloxazine (EMOVIT®, VIVALAN®, VIVARINT®, or VIVILAN®), maprotiline (DEPRILEPT®, LUDIOMIL®, or PSYMION®), bupropion (WELLBUTRIN® or ZYBAN®), and radafaxine.

Further non-limiting examples of specific antidepressants useful according to the invention include tricyclics such as amitriptyline, nortriptyline, and desipramine; serotonin-norepinephrine reuptake inhibitors such as venlafaxine (EFFEXOR®), duloxetine (CYMBALTA®), and milnacipran; tetracyclics such as maprotiline and mirtazapine; and other classes of compounds, including triazolopyridines such as trazodone.

The above compounds and classes of compounds are only examples of the types of active agents that can be used in combination with a compound of the present invention for the treatment of mood disorders, sleep disorders, or attention deficit disorders and are not intended to be limiting of the invention. Rather, various further active agents can be combined with one or more compounds of the present invention according to the invention. For example, any drug generally recognized as being an antidepressant, antinarcoleptic, or ADHD treatment can be used in combination with one or more compounds of the present invention. Moreover, it is possible according to the invention to combine two or more additional active agents with a compound of the present invention for the treatment of the noted conditions.

Non-limiting examples of further active agents that can be combined with compounds of the present invention include: mood stabilizers (such as lithium, olanzipine, verapamil, quetiapine, lamotrigine, carbamazepine, valproate, oxcarbazepine, risperidone, aripiprazole, and ziprasidone); antipsychotics (such as haloperidol and other butyrophenones, chlorpromazine, fluphenazine, perphenazine, prochlorperazine, and other phenothiazines, and clozapine); serotonin receptor antagonist (5-HT2 and 5-HT3 antagonists) (such as ondansetron, tropisetron, katenserin, methysergide, cyproheptadine, and pizotifen); serotonin receptor agonists (5-HT1A receptor agonists) (such as buspirone); stimulants [such as caffeine, ADDERALL®, methylphenidate (METADATE®, RITALIN®, or CONCERTA®), pemoline (CYLERT®), or modafinil (PROVIGIL®)]; and gamma-hydroxybutyrate (GHB) (XYREM®). Although the above compounds are described in terms of classes of compounds and specific compounds, it is understood that there is substantial overlap between certain classes of compounds (such as between mood stabilizers, antipsychotics, antidepressants, and serotonin receptor antagonists). Thus, specific compounds exemplifying a specific class of compounds may also properly be identified with one or more further classes of compounds. Accordingly, the above classifications should not be viewed as limiting the scope of the types of compounds useful in combination with compounds of the present invention for treating the conditions described herein.

Bupropion is also commonly combined with other therapeutic agents for the treatment of nicotine addiction. Thus, in one embodiment, a compound of the present invention is combined with one or more nicotine substitutes for the treatment of nicotine addiction. Nicotinic replacement therapies that may be combined with compounds of the present invention include, but are not limited to transdermal nicotine patches (e.g., Habitrol®, Nicoderm CQ®, and Nicotrol®), nicotine gum (e.g., Nicorette®), nicotine lozenges (e.g., Commit®), nicotine-containing sublingual tablets (e.g., Nicorette®Microtabs), and nicotine nasal sprays or inhalers. Compounds of the present invention may also be combined with one or more nicotinic drugs. One particular class of nicotinic drugs that may be used with compounds of the present invention encompasses α-4-β2 nicotinic receptor partial agonists, including varenicline (Chantix®). Combinations of compounds of the present invention with other therapeutic agents are also included in the present invention, wherein the condition to be treated is responsive to the inhibition of dopamine and/or norepinephrine reuptake.

The compound of Formula I and the one or more other therapeutic agents may be contained within a single composition or alternatively may be administered concurrently or sequentially (consecutively) in any order. For sequential administration, each of the compound of Formula I and the one or more other therapeutic agents can be formulated in its own pharmaceutical composition, each of which is to be administered sequentially, in any order. Alternatively, the compound of Formula I and the one or more other therapeutic agents can be formulated together. The compositions may be formulated for oral, systemic, topical, intravenous, intraparenteral, intravaginal, intraocular, transbuccal, transmucosal, or transdermal administration.

Methods of Use

In a further embodiment, the present invention provides a method for treating or delaying the progression of disorders that are alleviated by inhibiting monoamine reuptake in a patient, the method comprising administering a therapeutically effective amount of at least one compound of Formula I to the patient. In particular, the present invention relates to the field of treating addiction and depressive conditions in animals, particularly humans and other mammals, and associated effects of these conditions. It also may relate to the treatment of other conditions that may benefit from the inhibition of monoamine reuptake. It may particularly relate to the treatment of conditions that may benefit from one or more of dopamine, norepinephrine, and serotonin reuptake inhibition. In some embodiments, the compounds of the present invention are selective for one or more monoamine transporter. In some embodiments, the compounds bind more strongly to the dopamine and norepinephrine transporters than to the serotonin transporters. In preferred embodiments, the compounds bind more strongly to the dopamine transporters than the norepinephrine or serotonin transporters.

Addiction has its common meaning, e.g., the condition that exists when an individual persists in the use of a substance despite impairment or distress related to the use of the substance. In preferred embodiments, the compounds of the present invention show a slow onset and long duration of activity. These features make the compounds of the present invention particularly suitable for the treatment of addiction to abused substances, which commonly exhibit a fast onset and/or short duration of activity. Administration of the compounds of the present invention to subjects with addiction to one or more substances may be particularly suited for the treatment of cocaine, methamphetamine, and nicotine addiction.

The compounds of the present invention may also be applicable to treating depression and depressive conditions. Depression has its common meaning, e.g., a common mental disorder that presents with depressed mood, loss of interest or pleasure, feelings of guilt or low self-worth, disturbed sleep or appetite, low energy, and poor concentration or a mental state characterized by a pessimistic sense of inadequacy and a despondent lack of activity. Physical changes, such as insomnia, anorexia, weight loss, and decreased energy and libido can also occur as a result of depression. Depression includes dysthymic disorder or dysthymia, defined as a chronic low-grade depression and major depression as well as other stages or levels of depression. It also includes post-partum depression.

The compounds of the present invention may also be used for other conditions that may be responsive to inhibition of reuptake of one or more monoamines. In some embodiments, the compounds may be used to treat patients for conditions that are responsive to the inhibition of dopamine, norepinephrine, and/or serotonin. For example, in some embodiments, compounds of Formula I may be used to treat patients with bipolar disorder, attention deficit disorder (ADD), attention-deficit/hyperactivity disorder (ADHD), hypoactive sexual desire disorder, antidepressant-induced sexual dysfunction, orgasmic dysfunction, seasonal affective disorder/winter depression, obesity and food addiction, mania, bulimia and other eating disorders, panic disorders, obsessive compulsive disorder, schitzophrenia, schitzo-affective disorder, Parkinson's disease, narcolepsy, anxiety disorders, insomnia, chronic pain, migraine headaches, and restless legs syndrome.

The method of treatment generally includes administering a therapeutically effective amount of a compound of Formula I, optionally in a pharmaceutical composition including one or more pharmaceutically acceptable carriers. The therapeutically effective amount is preferably sufficient to inhibit the reuptake of one or more monoamines. The therapeutically effective amount is further preferably sufficient to cause some relief to the patient in the symptoms of the disorder for which the patient is being treated.

For example, in one embodiment, a method of treating cocaine addiction is provided. In such methods, a therapeutically effective amount of a compound of the present invention to treat a patient with cocaine addiction may be that amount capable of exerting some dopaminergic effects. Cocaine functions by inhibiting the reuptake of dopamine by blocking the dopamine transporter that transports excess dopamine back into the presynaptic cell. It has a fast onset of activity and short duration. Chronic cocaine use produces a withdrawal syndrome that is associated with depletion of dopamine and deficits in dopaminergic signaling. By providing a compound of the present invention with slow onset and long duration of activity, the compound may be able to reverse dopaminergic deficits in chronic cocaine users.

A therapeutically effective amount of a compound of the present invention to treat a patient with depression may be that amount capable of providing some relief from symptoms such as changes in mood, feelings of intense sadness and despair, mental slowing, loss of concentration, pessimistic worry, agitation, and self-deprecation and/or from physical changes such as insomnia, anorexia and weight loss, and decreased energy and libido. The levels of one or more of dopamine, norepinephrine, and serotonin may be low in subjects with depression and thus, inhibition of the reuptake of any of these monoamines by the appropriate transporter may be effective to adjust the monoamine levels and treat the symptoms of depression.

The therapeutically effective dosage amount of any specific formulation will vary somewhat from drug to drug, patient to patient, and will depend upon factors such as the condition of the patient and the route of delivery. When administered conjointly with other pharmaceutically active agents, even less of the compounds of the invention may be therapeutically effective. Further more, the therapeutically effective amount may vary depending on the specific condition to be treated.

The compounds of the invention can be administered once or several times a day. The daily dose can be administered either by a single dose in the form of an individual dosage unit or several smaller dosage units or by multiple administration of subdivided dosages at certain intervals. Possible routes of delivery include buccally, subcutaneously, transdermally, intramuscularly, intravenously, orally, or by inhalation.

The compounds of the invention may be used with other types of therapy, including those which are non-drug based. For example, addiction is commonly treated using one or more therapeutics in combination with behavior therapy. Thus, in some embodiments, the methods of the present invention comprise administering to a subject a compound that that is capable of functioning as a monoamine reuptake inhibitor in conjunction with one or more other types of non-drug-based therapy.

EXPERIMENTAL SECTION

Example 1

Synthesis

Nuclear magnetic resonance ($^1$H NMR and $^{13}$C NMR) spectra were recorded on a 300 MHz (Bruker AVANCE 300) or 500 MHz (Varian Unity ANOVA) spectrometer. Chemical shift data for the proton resonances were reported in parts per million ($\delta$) relative to internal $(CH_3)_4Si$ ($\delta 0.0$). Elemental analyses were performed by Atlantic Microlab, Norcross, Ga. Analytical thin-layer chromatography (TLC) was carried out on plates precoated with silica gel GHLF (250 µM thickness). TLC visualization was accomplished with a UV lamp or in an iodine chamber. All moisture-sensitive reactions were performed under a positive pressure of nitrogen maintained by a direct line from a nitrogen source. Anhydrous solvents were purchased from Aldrich Chemical Co. or VWR. The compounds described herein are referred to using a number-letter combination that can be cross-referenced with data presented in Example 2.

a) Synthesis of Compounds of the Present Invention

Synthesis of
2-(N-tert-Butylamino)-3-chlorobutanophenone (2o)

Step 1. 3'-Chlorobutanophenone (9o). 3-Chlorobenzonitrile 8d (3.0 g, 0.022 mol) and THF (75 mL) were placed in a 250 mL flask equipped with a magnetic stir bar. The flask was cooled to 0° C. with an ice-water bath. Propylmagnesium chloride (26.2 mL, 2M in Et$_2$O) was syringed in over a 10 min period. The reaction was stirred under nitrogen at room temperature. After 96 h, the flask was cooled to 0° C. The reaction was quenched by adding 0.1 M hydrochloric acid (75 mL). After stirring for 1 h at room temperature, the solution was transferred to a separatory funnel. Water (50 mL) and ammonium hydroxide (2 mL) were added to basify the reaction, and the aqueous layer was extracted three times with methylene chloride. The organic layer was dried (Na$_2$SO$_4$) and filtered. The solvent was removed under reduced pressure to give 3.51 g (88%) of 9o as a light-yellow oil. $^1$H NMR (CDCl$_3$) δ 7.95 (s, 1H), 7.81-7.87 (d, 1H), 7.50-7.56 (d, 1H), 7.38-7.40 (t, 1H), 2.90-2.95 (t, 2H), 1.72-1.81 (m, 2H), 0.99-1.05 (t, 3H).

Step 2. 2-Bromo-3'-chlorobutanophenone (10o). Ketone 9o (3.51 g, 0.01 mol) and methylene chloride (75 mL) were placed in a 500 mL flask equipped with a magnetic stir bar. The solution was stirred under nitrogen, and bromine (0.98 mL, 0.019 mol) was syringed into the flask. A small amount of bromine was added initially to catalyze the reaction. After reaction started, the remaining bromine was added over a 10 min period. After stirring for 14 h, the solution was transferred to a separatory funnel. A saturated sodium bicarbonate solution was added to basify the reaction. The aqueous layer was washed with a 1 M sodium thiosulfate solution and extracted three times with methylene chloride. The organic layer was dried (Na$_2$SO$_4$) and filtered. The solvent was removed under reduced pressure to give 5.20 g of an oil. The orange oil was purified by flash chromatography on silica gel using 5:1 hexane/methylene chloride as eluent to afford 4.04 g (80%) of 10o as a colorless oil. $^1$H NMR (CDCl$_3$) δ 8.00 (s, 1H), 7.86-7.91 (d, 1H), 7.54-7.59 (d, 1H), 7.41-7.48 (t, 1H), 4.99-5.05 (t, 1H), 2.07-2.30 (m, 2H), 1.07-1.12 (t, 3H).

Step 3. 2-(N-tert-Butylamino)-3'-Chlorobutanophenone (2o) Fumarate. Intermediate 10o (3.90 g, 0.015 mol) and tert-butylamine (7.84 mL, 0.075 mol) were placed in a sealed tube equipped with a magnetic stir bar. The tube was sealed and heated at 75° C. with an oil bath. After 2 h, the reaction mixture was cooled to room temperature and transferred to a separatory funnel. A saturated sodium bicarbonate solution was added to basify the reaction, and the aqueous layer was extracted with methylene chloride (3×). The organic layer was dried (Na$_2$SO$_4$), and the solvent was removed under reduced pressure. The oil was dissolved in methanol, and the solvent was removed under reduced pressure to afford 3.51 g (93%) of 2o as a pale-yellow oil. $^1$H NMR (CDCl$_3$) δ 7.95 (s, 1H), 7.84-7.89 (d, 1H), 7.53-7.58 (d, 1H), 7.40-7.48 (t, 1H), 4.04-4.10 (m, 1H), 2.04-2.24 (m, 2H), 1.02 (s, 9H), 0.92-0.99 (t, 1H). Amine 2o was converted to a fumarate salt by adding one equivalent of fumaric acid to an Et$_2$O solution of 2o. Recrystallized from methanol and Et$_2$O afforded 2.64 g of 2o•fumarate as a white solid: mp 155-156° C. $^1$H NMR (CD$_3$OD) δ 8.20 (s, 1H), 8.10-8.15 (d, 1H), 7.76-7.81 (d, 1H), 7.60-7.68 (t, 1H), 6.70 (s, 2H), 5.20-5.25 (t, 1H), 2.01-2.11 (m, 2H), 1.37 (s, 9H), 1.15-1.22 (t, 3H). Anal. (C$_{18}$H$_{24}$NO$_5$) C, H, N.

Synthesis of 2-(N-tert-Butylamino)-3'-chloropentanophenone (2p)

Step 1. 3'-Chloropentanophenone (9p). 3-Chlorobenzonitrile 8d (3.0 g, 0.022 mol) and THF (75 mL) were placed in a 250-mL flask equipped with a magnetic stir bar. The flask was cooled to 0° C. with an ice-water bath. Butylmagnesium chloride (26.2 mL, 2 M in THF) was syringed in over a 10-min period. The reaction mixture was stirred under nitrogen at room temperature. After 96 h, the flask was cooled to 0° C. and quenched by adding 0.1 M hydrochloric acid (75 mL). After stirring for 1 h at room temperature, the solution was transferred to a separatory funnel, water (50 mL) and ammonium hydroxide (2 mL) were added to basify the reaction, and the aqueous layer was extracted three times with methylene chloride. The organic layer was dried (Na$_2$SO$_4$) and filtered. The solvent was removed under reduced pressure to give 4.04 g (94%) of 9p as a light yellow solid. $^1$H NMR (CDCl$_3$) δ 7.95 (s, 1H), 7.85-7.80 (d, 1H), 7.56-7.51 (d, 1H), 7.45-7.38 (t, 1H), 2.98-2.91 (t, 2H), 1.80-1.68 (m, 2H), 1.49-1.38 (m, 2H), 1.01-0.92 (t, 3H).

Step 2. 2-Bromo-3'-chloropentanophenone (10p). Ketone 10p (4.04 g, 0.021 mol) and methylene chloride (75 mL) were placed in a 500-mL flask equipped with a magnetic stir bar. The solution was stirred under nitrogen, and bromine (0.98 mL, 19.2 mmol) was syringed into the flask. A small amount of bromine was added initially to catalyze the reaction. After reaction started, the remaining bromine was added over a 10-min period. After stirring for 14 h, the solution was transferred to a separatory funnel. A saturated sodium bicarbonate solution was added to basify the reaction. The mixture was extracted with methylene chloride (3×). The organic layer was dried (Na$_2$SO$_4$) and filtered. The solvent was removed under reduced pressure to give 6.02 g of an oil. The orange oil was purified by flash chromatography on silica gel (5:1 hexane-methylene chloride) to afford 3.69 g (65%) of 10p as a colorless oil. $^1$H NMR (CDCl$_3$) δ 7.97 (s, 1H), 7.90-7.85 (d, 1H), 7.59-7.54 (d, 1H), 7.47-7.40 (t, 1H), 5.09-5.02 (t, 1H), 2.22-2.07 (m, 2H), 1.65-1.39 (m, 2H), 1.05-0.95 (t, 3H).

Step 3. 2-(N-tert-Butylamino)-3'-chloropentanophenone (2p) Fumarate. Intermediate 10p (3.60 g, 0.013 mol) and tert-butylamine (6.86 mL, 65.3 mmol) were placed in a pressure tube equipped with a magnetic stir bar. The tube was sealed and heated at 75° C. with an oil bath. After 9 h, the reaction mixture was cooled to room temperature and transferred to a separatory funnel. A saturated sodium bicarbonate solution was added to basify the reaction, and the aqueous layer was extracted with methylene chloride (3×). The organic layer was dried (Na$_2$SO$_4$) and filtered. The solvent was removed under reduced pressure. The resulting oil was dissolved in methanol, and the solvent was removed under reduced pressure to afford 3.25 g (93%) of 2p as a pale yellow oil. $^1$H NMR (CDCl$_3$) δ 7.99 (s, 1H), 7.90-7.85 (d, 1H), 7.60-7.55 (d, 1H), 7.50-7.42 (t, 1H), 4.15-4.09 (m, 1H), 1.60-1.43 (m, 2H), 1.43-1.25 (m, 2H), 1.02 (s, 9H), 0.94-0.88 (t, 3H). Amine 2p was converted to a fumarate salt using the procedure described for 2b. Recrystallization from methanol and Et$_2$O afforded 2.64 g of 2p•fumarate as a white solid: mp 159-160° C. $^1$H NMR (CDCl$_3$/CD$_3$OD) δ 8.05 (s, 1H), 7.98-7.93 (d, 1H), 7.71-7.66 (d, 1H), 7.60-7.52 (t, 1H), 6.77 (s, 2H), 4.74-4.69 (t, 1H), 1.91-1.69 (m, 2H), 1.39-1.17 (m, 2H), 1.25 (s, 9H), 0.91-0.85 (t, 3H). Anal. (C$_{19}$H$_{26}$NO$_5$) C, H, N.

Synthesis of 2-(N-tert-Butylamino)-3'-chlorohexanophenone (2q)

Step 1. 3'-Chlorohexanophenone (9q). 3-Chlorobenzonitrile 8d (5 g, 0.036 mol) and dry THF (110 mL) were placed in a flask equipped with a magnetic stir bar. The flask was cooled to 0° C. with an ice-water bath and stirred under nitrogen. Pentylmagnesium bromide (22 mL, 2 M in Et$_2$O) was syringed in over a 10-min period. After 1 h, the reaction mixture was warmed to room temperature. After 6 days, the flask was cooled to 0° C., and cold 1 M hydrochloric acid (75 mL) was added slowly. The reaction mixture was allowed to stir at room temperature overnight. The solution was transferred to a separatory funnel and basified with ammonium hydroxide. The aqueous layer was extracted three times with ethyl acetate. The organic layer was dried (Na$_2$SO$_4$) and filtered. The solvent was removed under reduced pressure to give 7.55 g (99%) of 9q as a light yellow solid. $^1$H NMR (CDCl$_3$) δ 7.93 (s, 1H), 7.85-7.81 (d, 1H), 7.55-7.51 (d, 1H), 7.43-7.37 (t, 1H), 2.97-2.91 (t, 2H), 1.76-1.68 (m, 2H), 1.40-1.33 (m, 4H), 0.94-0.89 (m, 3H).

Step 2. 2-Bromo-3'-chlorohexanophenone (10q). Ketone 9q (7.55 g, 0.036 mol) was dissolved in chloroform (200 mL) and stirred under nitrogen. Bromine (1.9 mL, 36 mmol) was syringed into the flask. The flask was heated briefly with a heat gun to initiate the reaction (approx. 1 min). The HBr evolved was allowed to escape via a syringe needle placed in the rubber septa. After stirring 5 h, the solution was transferred to a separatory funnel. The reaction mixture was basified with saturated sodium bicarbonate, and the aqueous layer was extracted with chloroform (3×). The organic layer was dried (Na$_2$SO$_4$) and filtered. The solvent was removed under reduced pressure to afford 10.66 g (100%) of 10q as a yellow oil. $^1$H NMR (CDCl$_3$) δ 7.99 (s, 1H), 7.91-7.86 (d, 1H), 7.60-7.55 (d, 1H), 7.47-7.40 (t, 1H), 5.08-5.02 (t, 1H), 2.21-2.09 (m, 2H), 1.55-1.34 (m, 4H), 0.96-0.90 (t, 3H).

Step 3. 2-(N-tert-Butylamino)-3'-chlorohexanophenone (2q) Fumarate. Intermediate 10q (10.66 g, 0.037 mol) and tert-butylamine (20 mL) were placed in a flask equipped with a magnetic stir bar and a reflux condenser. The reaction mixture was refluxed under nitrogen at 60° C. After 26 h, the reaction mixture was cooled to room temperature, basified with saturated sodium bicarbonate, and extracted with methylene chloride (3×). The organic layer was dried (Na$_2$SO$_4$) and filtered. The solvent was removed under reduced pressure to give about 10 g of an oil. The orange oil was purified by flash chromatography [CMA 80 (80% CH$_2$Cl$_2$, 18% CH$_3$OH, 2% conc. NH$_4$OH)] to afford 2.75 g (27%) of 2q as a light yellow oil. $^1$H NMR (CDCl$_3$) δ 7.96 (s, 1H), 7.88-7.84 (d, 1H), 7.58-7.54 (d, 1H), 7.47-7.41 (t, 1H), 4.12-4.08 (m, 1H), 1.60-1.45 (m, 2H), 1.39-1.25 (m, 4H), 1.02 (s, 9H), 0.92-0.87 (t, 3H). Amine 2q was converted to a fumarate salt using the procedure described for 2b. Recrystallization from methanol and ethyl acetate to afford 3.06 g of 2q•fumarate as a white crystalline solid: mp 172-173° C. $^1$H NMR (CD$_3$OD) δ 8.19 (s, 1H), 8.14-8.11 (d, 1H), 7.80-7.77 (d, 1H), 7.67-7.60 (t, 1H), 6.70 (s, 2H), 5.23-5.19 (t, 1H), 2.01-1.95 (m, 2H), 1.36 (s, 9H), 1.39-1.19 (m, 4H), 0.86-0.81 (t, 3H). Anal. (C$_{20}$H$_{28}$ClNO$_5$) C, H, N.

Synthesis of 2-(N-tert-Butylamino)-3'-chloroheptanophenone (2r)

Step 1. 3'-Chloroheptanophenone (9r). 3-Chlorobenzonitrile 8d (5 g, 0.036 mol) and dry THF (100 mL) were placed in a flask equipped with a magnetic stir bar. The flask was cooled to 0° C. with an ice-water bath and stirred under nitrogen. Hexylmagnesium bromide (22 mL, 2 M in Et$_2$O) was syringed in over a 10-min period. After 1 h, the reaction mixture was warmed to room temperature. After 6 days, the flask was cooled to 0° C., and cold 1 M hydrochloric acid (75 mL) was added slowly. The reaction mixture was allowed to stir at room temperature overnight. The solution was transferred to a separatory funnel and basified with ammonium hydroxide. The aqueous layer was extracted three times with ethyl acetate. The organic layer was dried (Na$_2$SO$_4$) and filtered. The solvent was removed under reduced pressure to give 7.74 g (95%) of 9r as a light yellow solid. $^1$H NMR (CDCl$_3$) δ 7.93 (s, 1H), 7.85-7.81 (d, 1H), 7.55-7.51 (d, 1H), 7.43-7.37 (t, 1H), 2.97-2.91 (t, 2H), 1.78-1.67 (m, 2H), 1.43-1.23 (m, 6H), 0.92-0.87 (t, 3H).

Step 2. 2-Bromo-3'-chloroheptanophenone (10r). Ketone 9r (7.74 g, 0.034 mol) was dissolved in chloroform (200 mL) and stirred under nitrogen. Bromine (1.8 mL, 34 mmol) was syringed into the flask. The flask was heated briefly with a heat gun to initiate the reaction (approx. 1 min). The HBr evolved was allowed to escape via a syringe needle placed in the rubber septa. After stirring 5 h, the solution was transferred to a separatory funnel. The reaction mixture was basified with saturated sodium bicarbonate, and the resulting aqueous layer was extracted three times with chloroform. The organic layer was dried (Na$_2$SO$_4$) and filtered. The solvent was removed under reduced pressure to afford 10.42 g (100%) of 10b as a yellow oil. $^1$H NMR (CDCl$_3$) δ 7.99 (s, 1H), 7.90-7.87 (d, 1H), 7.59-7.55 (d, 1H), 7.47-7.40 (t, 1H), 5.08-5.02 (t, 1H), 2.22-2.09 (m, 2H), 1.56-1.33 (m, 6H), 0.92-0.87 (m, 3H).

Step 3. 2-(N-tert-Butylamino)-3'-chloroheptanophenone (2r) Fumarate. Intermediate 10r (10.42 g, 0.034 mol) and tert-butylamine (18 mL) were placed in a flask equipped with a magnetic stir bar and a reflux condenser. The reaction mixture was refluxed under nitrogen at 60° C. After 16 h, the reaction mixture was cooled to room temperature, basified with saturated sodium bicarbonate, and extracted three times with methylene chloride. The organic layer was dried (Na$_2$SO$_4$) and filtered. The solvent was removed under reduced pressure to give about 10 g of an oil. The orange oil was purified by flash chromatography [CMA 80 (80% CH$_2$Cl$_2$, 18% CH$_3$OH, 2% conc. NH$_4$OH)] to afford 3.08 g (30%) of 2r as a light yellow oil. $^1$H NMR (CDCl$_3$) δ 7.96 (s, 1H), 7.87-7.84 (d, 1H), 7.58-7.54 (d, 1H), 7.47-7.41 (t, 1H), 4.12-4.09 (m, 1H), 1.57-1.45 (m, 2H), 1.34-1.24 (m, 6H), 1.02 (s, 9H), 0.89-0.84 (t, 3H). Amine 2r was converted to a fumarate salt using the procedure described for 2b. Recrystallization from ethyl acetate afforded 3.02 g of 2r•fumarate as a white crystalline solid: mp 162-163° C. $^1$H NMR (CD$_3$OD) δ 8.19 (s, 1H), 8.13-8.09 (d, 1H), 7.80-7.76 (d, 1H), 7.66-7.60 (t, 1H), 6.69 (s, 2H), 5.19-5.15 (t, 1H), 2.01-1.91 (m, 2H), 1.34 (s, 9H), 1.25-1.15 (m, 6H), 0.86-0.81 (m, 3H). Anal. (C$_{21}$H$_{30}$ClNO$_5$) C, H, N.

Synthesis of 2-(N-tert-Butylamino)-3'-chlorooctanophenone (2s)

Step 1. 3'-Chlorooctanophenone (9s). To a flame-dried flask equipped with a magnetic stir bar, 1-iodoheptane (14.46 g, 0.064 mol) was added in 100 mL of the solvent system. The solvent was 3:2 by volume of dry n-pentane-dry Et$_2$O (60 mL:40 mL). The solution was cooled to −78° C. and stirred under a nitrogen atmosphere. tert-Butyllithium (2.2 equivalents, 75 mL, 1.7 M in pentane) were added dropwise over two 30-min periods using a syringe pump. The reaction turned light yellow, and a white precipitate formed. After the addition was complete, the solution was warmed to room temperature. After warming for 30 min, the reaction mixture was cooled to −78° C., and 3'-chlorobenzonitrile 8b (10 g, 0.073 mol) was added. After stirring for 10 min, the reaction mixture was warmed to room temperature. The reaction turned yellow-orange. After 3 h, the solvent was removed under nitrogen, and 1 M hydrochloric acid (50 mL) was added. After stirring for 30 min, the solution was transferred to a separatory funnel. The aqueous layer was extracted three times with ethyl acetate. The organic layer was dried (Na$_2$SO$_4$) and filtered. The solvent was removed under reduced pressure to afford 17 g of an oil. The orange oil was purified by flash chromatography (6:1 hexane-methylene chloride) to afford 15.8 g (91%) of 9s as a light yellow oil. $^1$H NMR (CDCl$_3$) δ 7.93 (s, 1H), 7.85-7.81 (d, 1H), 7.55-7.50 (d, 1H), 7.43-7.37 (t, 1H), 2.97-2.91 (t, 2H), 1.76-1.70 (m, 2H), 1.41-1.29 (m, 8H), 0.86-0.91 (t, 3H).

Step 2. 2-Bromo-3'-chlorooctanophenone (10s). In a flask equipped with a magnetic stir bar, ketone 9s (15 g, 0.063 mol) was dissolved in chloroform (200 mL) and stirred under nitrogen. Bromine (3.23 mL, 63 mmol) was syringed in over a short period of time. The reaction mixture initially turned dark orange, but the color dissipated over time. The reaction mixture was stirred under nitrogen, and the hydrogen bromide gas evolved in the reaction mixture was allowed to escape into the hood via a syringe needle placed into the rubber septa. After 2 h, the reaction mixture was transferred to a separatory funnel, basified with saturated sodium bicarbonate, and extracted three times with chloroform. The organic layer was dried (Na$_2$SO$_4$) and filtered. The solvent was removed under reduced pressure to give 19.95 g (100%) of 10s as an orange oil. $^1$H NMR (CDCl$_3$) δ 7.99 (s, 1H), 7.90-7.87 (d, 1H), 7.58-7.54 (d, 1H), 7.43-7.36 (t, 1H), 5.08-5.02 (t, 1H), 2.19-2.14 (m, 2H), 1.55-1.30 (m, 8H), 0.91-0.86 (m, 3H).

Step 3. 2-(N-tert-Butylamino)-3'-chlorooctanophenone (2s) Fumarate. Intermediate 10s (19 g, 0.060 mol) and tert-butylamine (63 mL) were placed in a flask equipped with a magnetic stir bar and a reflux condenser. The reaction mixture was refluxed under nitrogen at 60° C. After 24 h, the reaction mixture was cooled to room temperature, basified with saturated sodium bicarbonate solution, and extracted three times with methylene chloride. The organic layer was dried (Na$_2$SO$_4$) and filtered. The solvent was removed under reduced pressure to give 17.2 g (93%) of 2s as a dark orange oil. The orange oil was used without further purification. $^1$H NMR (CDCl$_3$) δ 7.96 (s, 1H), 7.87-7.82 (d, 1H), 7.58-7.54 (d, 1H), 7.37-7.31 (t, 1H), 4.13-4.08 (m, 1H), 1.54-1.17 (m, 10H), 1.02 (s, 9H), 0.89-0.83 (t, 3H). Amine 2s was converted to a fumarate salt using the procedure described for 2b. Recrystallization from methanol and Et$_2$O afforded 9.61 g of 2s•fumarate as a white crystalline solid: mp 139-140° C. $^1$H NMR (CD$_3$OD) δ 8.18 (s, 1H), 8.13-8.09 (d, 1H), 7.79-7.75 (d, 1H), 7.65-7.59 (t, 1H), 6.69 (s, 2H), 5.23-5.19 (m, 1H), 2.00-1.97 (m, 2H), 1.35 (s, 9H), 1.19-1.10 (m, 8H), 0.82-0.79 (m, 3H). Anal. (C$_{22}$H$_{32}$ClNO$_5$.0.5 H$_2$O)C, H, N.

Synthesis of 2-(N-tert-Butylamino)-3'-chlorophenyl-4-methylpentanophenone (2t)

Step 1. 3'-Chlorophenyl-4-methylpentanophenone (9t). 3'-Chlorobenzonitrile 8a (4.5 g, 0.033 mol) and tetrahydrofuran (dry, 150 mL) were place in a flask equipped with a magnetic stir bar. The Grignard reagent (CH$_3$)$_2$CHCH$_2$MgBr (5.8 g, 0.033 mol) was added, and the reaction mixture was stirred under nitrogen for 72 h. The reaction mixture became orange in color. A solution of 1 M hydrochloric acid (20 mL) was added, and the reaction mixture was stirred overnight. The yellow solution was transferred to a separatory funnel, a saturated sodium bicarbonate solution was added to basify the reaction, and the aqueous layer was extracted three times with methylene chloride. The organic layer was dried (Na$_2$SO$_4$) and filtered. The solvent was removed under reduced pressure to give 4.5 g of an oil. The orange oil was purified by flash chromatography (7:1 hexane-methylene chloride) to afford 2.20 g (32%) of 9t as a pale yellow oil. $^1$H NMR (CDCl$_3$) δ 7.92 (s, 1H), 7.85-7.81 (d, 1H), 7.55-7.51 (d, 1H), 7.46-7.38 (t, 1H), 2.97-2.91 (t, 2H), 1.71-1.59 (m, 3H), 0.96-0.94 (d, 6H). (Note: The Grignard reagent was made by adding the alkyl bromide and magnesium together in tetrahydrofuran).

Step 2. 2-Bromo-3'-chlorophenyl-4-methylpentanophenone (10t). Ketone 9t (2.2 g, 0.01 mol) and methylene chloride (150 mL) were placed in a 500-mL flask equipped with a magnetic stir bar. Bromine (0.53 mL, 10.4 mmol) was syringed in over a short period of time. The reaction mixture initially turned dark orange, but the color dissipated over time. The reaction was stirred under nitrogen, and the hydrogen bromide gas evolved in the reaction was allowed to escape. After 4 h, the reaction mixture was transferred to a separatory funnel and basified with a saturated sodium bicarbonate solution. The aqueous layer was extracted three times with methylene chloride. The organic layer was dried (Na$_2$SO$_4$) and filtered. The solvent was removed under reduced pressure to give 2.92 g of an oil. The orange oil was purified by flash chromatography (7:1 hexane-methylene chloride) to afford 2.42 g (81%) of 10t as a colorless oil. $^1$H NMR (CDCl$_3$) δ 7.99 (s, 1H), 7.91-7.87 (d, 1H), 7.59-7.55 (d, 1H), 7.47-7.41 (t, 1H), 5.16-5.10 (t, 1H), 2.15-1.76 (m, 3H), 1.00-0.97 (d, 6H).

Step 3. 2-(N-tert-Butylamino)-3'-chlorophenyl-4-methylpentanophenone (2t) Fumarate. Intermediate 10t (2.42 g, 0.084 mol) and tert-butylamine (8.82 mL, 84 mmol) were placed in a pressure tube equipped with a magnetic stir bar. The tube was sealed, and the reaction mixture was stirred at 80° C. for 12 h. A white precipitate formed. The reaction mixture was cooled and transferred to a separatory funnel. The reaction mixture was basified with a saturated sodium bicarbonate solution, and the aqueous layer was extracted three times with methylene chloride. The organic layer was dried (Na$_2$SO$_4$) and filtered. The solvent was removed under reduced pressure to give 2.30 g of an oil. The yellowish oil was purified by flash chromatography [7:1 hexane-(9:1 Et$_2$O-Et$_3$N)] to afford 800 mg (34%) of 2q as a colorless oil. $^1$H NMR (CDCl$_3$) δ 7.95 (s, 1H), 7.88-7.84 (d, 1H), 7.58-7.54 (d, 1H), 7.47-7.41 (t, 1H), 4.20-4.14 (m, 1H), 1.26-1.19 (m, 3H), 1.02 (s, 9H), 0.82-0.79 (d, 6H). Amine 2t was converted to a fumarate salt using the procedure described for 2b. Recrystallization from Et$_2$O afforded 728 mg of 2t•fumarate as a white solid: mp 172-174° C. $^1$H NMR (CD$_3$OD) δ 8.04 (s, 1H), 7.99-7.95 (d, 1H), 7.73-7.69 (d, 1H), 7.62-7.54 (t, 1H), 6.76 (s, 2H), 1.66-1.57 (m, 3H), 1.29 (s, 9H), 1.10-1.07 (d, 3H), 0.94-0.91 (d, 3H). Anal. (C$_{20}$H$_{28}$ClNO$_5$.0.25 H$_2$O)C, H, N.

Synthesis of 2-(N-tert-Butylamino)-3'-chlorophenyl-4-cyclohexylbutanophenone (2u)

Step 1. 1-Iodo-3-cyclohexylpropane. 1-Chloro-3-cyclohexylpropane (6 mL, 37 mmol) and sodium iodide (5.6 g, 0.037 mol) were dissolved in acetone (200 mL) in a 500-mL flask equipped with a magnetic stir bar. The reaction mixture was refluxed 72 h and cooled. The white precipitate was filtered, and the solvent was removed under reduced pressure. The yellow solution was transferred to a separatory funnel and 1 M sodium thiosulfate added. The aqueous layer was extracted three times with methylene chloride. The organic layer was dried (Na$_2$SO$_4$) and filtered. The solvent was removed under reduced pressure to afford 8.20 g (85%) of product as a light yellow oil. $^1$H NMR (CDCl$_3$) δ 3.20-3.14 (t, 2H), 1.89-1.65 (m, 7H), 1.34-1.24 (m, 6), 0.95-0.86 (m, 2H).

Step 2. 3'-Chlorophenyl-4-cyclohexybutanophenone (9u). To a flame-dried flask, 1-iodo-3-cyclohexylpropane (8.20 g, 0.033 mol) was dissolved (100 mL) in 3:2 by volume of dry n-pentane-dry $Et_2O$. The solution was cooled to –78° C. and stirred with a magnetic stir bar. tert-Butyllithium (2.1 equivalents, 41 mL, 1.7 M in pentane) was added dropwise over a 30-min period using a syringe pump. The reaction mixture turned light yellow, and a white precipitate formed. After the addition was complete, the reaction mixture was stirred for 5 min. The solution was warmed to room temperature and stirred for 45 min. The reaction mixture was cooled to –78° C., and 3'-chlorobenzonitrile 8a (4.5 g, 0.033 mol) was added. After stirring for 10 min, the reaction mixture was warmed to room temperature. The reaction turns orange. After 16 h, the solvent was removed under nitrogen. Saturated ammonium chloride (20 mL) was added. After 10 min, 1 M hydrochloric acid (35 mL) was added. The solution was transferred to a separatory funnel. The aqueous layer was extracted three times with methylene chloride. The organic layer was dried ($Na_2SO_4$) and filtered. The solvent was removed under reduced pressure to afford 10.78 g of an oil. The orange oil was purified by flash chromatography (11:1 hexane-ethyl acetate) to afford 4.1 g (47%) of 9u as a colorless oil. $^1H$ NMR ($CDCl_3$) δ 7.92 (s, 1H), 7.84-7.81 (d, 1H), 7.54-7.51 (d, 1H), 7.43-7.37 (t, 1H), 2.95-2.88 (t, 2H), 1.81-1.68 (m, 7H), 1.29-1.16 (m, 6H), 0.95-0.86 (m, 2H).

Step 3. 2-Bromo-3'-chlorophenyl-4-cyclohexylbutanophenone (10u). Ketone 9u (3.97 g, 0.015 mol) and methylene chloride (100 mL) were placed in a 500-mL flask equipped with a magnetic stir bar. Bromine (0.77 mL, 15 mmol) was syringed in over a short period of time. The reaction mixture initially turned dark orange, but the color dissipated over time. The reaction mixture was stirred under nitrogen, and the hydrogen bromide gas evolved in the reaction was allowed to escape into the hood. After 4 h, the reaction mixture was transferred to a separatory funnel and basified with a saturated sodium bicarbonate solution. After the addition of a 1 M sodium thiosulfate solution, the aqueous layer was extracted three times with methylene chloride. The organic layer was dried ($Na_2SO_4$) and filtered. The solvent was removed under reduced pressure to give 4.79 g of an oil. The orange oil was purified by flash chromatography (5:1 hexane-methylene chloride) to afford 3.79 g (74%) of 10u as a light yellow oil. $^1H$ NMR ($CDCl_3$) δ 7.98 (s, 1H), 7.91-7.86 (d, 1H), 7.59-7.54 (d, 1H), 7.47-7.40 (t, 1H), 5.04-4.98 (t, 1H), 2.23-2.10 (m, 2H), 1.74-1.68 (m, 5H), 1.34-1.18 (m, 6H), 0.93-0.89 (m, 2H).

Step 4. 2-(N-tert-Butylamino)-3'-chlorophenyl-4-cyclohexylbutanophenone (2u). Intermediate 10u (2.56 g, 0.0075 mol) and tert-butylamine (7.83 mL, 75 mmol) were placed in a pressure tube equipped with a magnetic stir bar. The tube was sealed, and the reaction mixture was stirred at 75° C. for 5 h. A white precipitate formed. The reaction was transferred to a separatory funnel and basified with a saturated sodium bicarbonate solution. The aqueous layer was extracted three times with methylene chloride. The organic layer was dried ($Na_2SO_4$) and filtered. The solvent was removed under reduced pressure to give 2.10 g (84%) of 2u as a light yellow oil. $^1H$ NMR ($CDCl_3$) δ 7.95 (s, 1H), 7.87-7.83 (d, 1H), 7.58-7.54 (d, 1H), 7.47-7.40 (t, 1H), 4.09-4.06 (m, 1H), 1.67-1.63 (m, 7H), 1.33-1.16 (m, 6H), 1.01 (s, 9H), 0.88-0.83 (m, 2H). Amine 2u was converted to a fumarate salt using the procedure described for 2b. Recrystallization from isopropanol and hexane afforded 1.16 g of 2u•fumarate as a white solid: mp 150-152° C. $^1H$ NMR ($CD_3OD$) δ 8.17 (s, 1H), 8.14-8.09 (d, 1H), 7.81-7.76 (d, 1H), 7.67-7.60 (t, 1H), 6.68 (s, 2H), 5.22-5.17 (m, 1H), 2.04-1.95 (m, 2H), 1.62-1.52 (m, 5H), 1.34 (s, 9H), 1.20-1.05 (m, 6H), 0.85-0.70 (m, 2H). Anal. ($C_{24}H_{34}ClNO_5$) C, H, N.

Synthesis of 2-(N-Cyclopropylamino)-3'-chloropropiophenone (2x)

2-(N-Cyclopropylamino)-3'-chloropropiophenone (2x) Hydrochloride. A solution of 2-bromo-1-(3-chlorophenyl)propanol (14.7 g, 59.3 mmol) and cyclopropylamine (5.2 mL, 75.0 mmol) in THF (300 mL) was sealed in a glass reactor with Teflon cap and heated to 50° C. for 18 h. The reaction mixture was concentrated and the residue was taken up into ethyl acetate and washed with saturated aqueous $NaHCO_3$, water and brine, dried ($MgSO_4$) and concentrated. The crude product was purified by automated flash chromatography (silica gel, 4/1 hexane/ethyl acetate) to yield 2.77 g (21%) of orange oil. This material was dissolved into diethyl ether (250 mL and treated with 4 N HCl in dioxane (16 mL, 64 mmol); the mixture stirred overnight at room temperature. The resulting solids were filtered and recrystallized (methanol/ether) to yield 1.40 g (43%) of pure 2x•hydrochloride. mp 181-183° C. (dec.); $^1H$ NMR ($CD_3OD$ 300 MHz) δ 8.10 (s, 1H), 8.03 (d, 1H, J=9 Hz), 7.76 (d, 1H, J=3 Hz), 7.62 (t, 1H, J=6 Hz, 9 Hz), 5.30-5.27 (m, 1H), 2.85-2.77 (m, 1H), 1.62 (d, 3H, J=6 Hz), 0.97-0.93 (m, 3H); $^{13}C$ NMR ($CDCl_3$, 75 MHz) δ 135.1, 133.2, 130.0, 128.4, 126.4, 98.4, 58.1, 28.7, 19.6, 8.6, 6.6, 6.3; ESI-MS, calculated for $C_{12}H_{14}ClNO$ (M+H)$^+$224.7; observed 224.1. Anal. ($C_{12}H_{15}ClNO_5$.0.25 $H_2O$)C, H, N.

Synthesis of 2-(N-Cyclobutylamino)-3'-chloropropiophenone (2y)

2-(N-Cyclobutylamino)-3'-chloropropiophenone (2y) Hydrochloride. 2-Bromo-1-(3-chlorophenyl)propan-1-one (250 mg, 1.01 mmol) was dissolved in dry ether (1 mL), and the solution was chilled to 0° C. Cyclobutylamine (0.19 mL, 2.22 mmol) was then added all at once and the reaction mixture was allowed to warm to room temperature and stir overnight. The reaction mixture was poured into an Erlenmeyer flask containing 10% aqueous HCl and EtOAc, and stirred for 10 min. The biphasic mixture was partitioned in a separatory funnel. The aqueous layer was extracted twice with EtOAc and then basified to pH 8-9 with saturated aqueous $Na_2CO_3$. The basified aqueous layer was extracted twice with ether and the combined organic extracts were washed with brine, dried over $Na_2SO_4$, filtered, and concentrated to approximately half the original volume. (Caution: Do not concentrate to dryness or the compound will decompose). To the stirring ether solution was slowly added 1 M HCl/$Et_2O$ until the solid stopped precipitating out of solution (typically 0.5 to 1 mL was needed). After stirring for 3 h, the solid was filtered, washed with ether, and dried. In order to remove the unreacted cyclobutylamine hydrochloride, the crude solid was then recrystallized from MeOH/ether and left to sit in a freezer overnight. The solid was then filtered, washed with ether, and dried to afford 60.1 mg (22% yield) of 2y•hydrochloride as a white flaky solid. mp 186-187° C. $^1H$ NMR ($CD_3OD$, 300 MHz) δ 8.09 (s, 1H), 8.02 (d, J=9.0 Hz, 1H), 7.77-7.74 (m, 1H), 7.60 (t, J=15.0, 9.0 Hz, 1H), 5.08 (q, J=21.0, 15.0, 6.0 Hz, 1H), 3.94-3.82 (m, 1H), 2.38-2.20 (m, 4H), 1.97-1.85 (m, 2H), 1.55 (d, J=6.0 Hz, 3H); $^{13}C$ NMR ($CD_3OD$, 75 MHz) ppm 196.1, 136.7, 135.9, 132.1, 129.7, 128.4, 57.7, 51.7, 28.1, 27.8, 16.5, 15.8; Anal. ($C_{13}H_{17}Cl_2NO \cdot 0.5H_2O$) C, H, N.

Synthesis of 2-(N-Cyclopentylamino)-3'-chloropropiophenone (2z)

Sodium bicarbonate (6.0 g, 0.071 mol) was suspended in a solution of 2-bromo-1-(3-chlorophenyl)propanone (6.0 g, 0.024 mol) in acetonitrile (30 mL). Cyclopentylamine (3.88 g, 0.012 mol) was added and the mixture stirred at ambient temperature for 6 h. The mixture was carefully poured into 10% hydrochloric acid (50 mL) and ethyl acetate (50 mL). After mixing, the aqueous layer was separated, washed with ethyl acetate (25 mL), and made alkaline with conc. NH$_4$OH-water (1:1) mixture. The mixture was extracted with Et$_2$O (2×100 mL), and the combined ethereal extracts were dried (K$_2$CO$_3$) and filtered. The solvent was removed to give 6.4 g of yellow oil. The fumarate salt 2z•fumarate was formed and recrystallized form methanol-Et$_2$O to give a white solid: mp 171-173° C.(dec). $^1$H NMR (D$_6$MSO) δ 9.76 (bs, 1H), 8.10 (s, 1H), 8.03 (d, 1H, J=6 Hz), 7.77 (d, 1H, J=6 Hz), 7.61 (t, 1H, J=6 Hz), 6.54 (s, 2H), 4.82 (q, 1H, J=Hz), 3.27 (m, 1H), 1.80-1.46 (m, 8H), 1.32 (d, 3H, J=9 Hz). Anal. ($C_{18}H_{22}ClNO_5$) C, H, N.

Synthesis of 2-(tert-Butylamino)-3',4'-dichlorobutyrophenone (2aa)

Step 1. 3',4'-Dichlorobutyrophenone (9aa). To a solution of 3.00 g (0.017 mol) of 8e in 40 mL of dry tetrahydrofuran cooled to 0° C. was added dropwise 21 mL (2.0 M in Et$_2$O) of propylmagnesium chloride. The reaction solution was allowed to warm to room temperature and stirred at room temperature for 144 h under nitrogen. The reaction solution was cooled to 0° C. and 150 mL of a 5% aqueous hydrochloric acid solution was added dropwise. After stirring overnight at room temperature, the reaction mixture was quenched with a saturated aqueous sodium bicarbonate solution, and the product was extracted with methylene chloride, dried (Na$_2$SO$_4$), and filtered. The solvent was removed, and the resulting residue was dried briefly under high vacuum to give 3.87 g of a brown oil. Purification by flash chromatography (silica, 5:1 hexane-methylene chloride) gave 3.15 g (83%) of 9aa as a yellow oil. $^1$H NMR (CDCl$_3$) δ 8.03 (s, 1H), 7.80-7.76 (dd, 1H), 7.54 (d, 1H), 2.91 (t, 2H), 1.84-1.69 (m, 2H), 1.00 (t, 3H).

Step 2. 2-Bromo-3',4'-dichlorobutyrophenone (10aa). To a solution of 3.91 g (0.018 mol) of 9aa in 70 mL of methylene chloride was added ten drops of bromine. After stirring at room temperature under nitrogen for several minutes, the characteristic red color of bromine disappeared indicating initiation of the reaction. The remainder of the 1 mL (18.30 mmol) of bromine was added dropwise and the reaction solution was allowed to stir at room temperature under nitrogen for 9.5 h. The reaction solution was quenched and brought to a pH of 9 with a saturated aqueous solution of sodium bicarbonate and solid sodium bicarbonate. The product was extracted with methylene chloride, dried (Na$_2$SO$_4$), and filtered. The solvent was removed, and the resulting residue was dried briefly under high vacuum to give 5.62 g (>100%) of 10aa as an orange oil. $^1$H NMR (CDCl$_3$) δ 8.10 (s, 1H), 7.86-7.82 (dd, 1H), 7.57 (d, 1H), 4.95 (t, 1H), 2.30-2.07 (m, 2H), 1.09 (t, 3H).

Step 3. 2-(tert-Butylamino)-3',4'-dichlorobutyrophenone (2aa) Fumarate. To a pressure tube was transferred 5.49 g (0.019 mol) of 10aa with a minimal amount of methylene chloride. Most of the methylene chloride was removed via positive nitrogen flow, 29 mL (278.21 mmol) of tert-butylamine was added in one portion, and the tube was sealed and placed in an oil bath heated to 55° C. After stirring at 55° C. for 15 h, the reaction mixture was allowed to cool to room temperature. The reaction mixture was quenched and brought to pH 10 with a saturated aqueous solution of sodium bicarbonate, and the product was extracted with methylene chloride, dried (Na$_2$SO$_4$), and filtered. The solvent was removed, and the resulting residue was dried briefly under high vacuum to give 5.55 g of a brown oil. Purification by flash chromatography (silica, 9:1:50 Et$_2$O-Et$_3$N-hexane) gave 3.88 g (73%) of 2aa as an orange oil. $^1$H NMR (CDCl$_3$) δ 8.08 (s, 1H), 7.85-7.80 (dd, 1H), 7.58 (d, 1H), 4.04-3.99 (m, 1H), 1.70-1.61 (m, 1H), 1.40-1.35 (m, 1H), 1.02 (s, 9H), 0.96 (t, 3H). To a solution of 3.30 g (0.013 mol) of 2aa in methylene chloride-methanol was added 1.48 g (0.013 mol) of fumaric acid. The reaction solution was allowed to stir for 15 min, and the solvent was removed in vacuo leaving a white solid. Recrystallization from methanol-Et$_2$O afforded 2.65 g of 2a•fumarate as a white solid: mp 185-186° C. $^1$H NMR (CD$_3$OD) δ 8.36 (s, 1H), 8.13-8.09 (dd, 1H), 7.81 (d, 1H), 5.20 (t, 1H), 2.13-2.01 (m, 2H), 1.35 (s, 9H), 0.90 (t, 3H). Anal. ($C_{18}H_{23}Cl_2NO_5$) C, H, N.

Synthesis of 2-(tert-Butylamino)-3',4'-dichloropentanophenone (2bb)

Step 1. 3',4'-Dichloropentanophenone (9bb). To a solution of 4.0 g (0.023 mol) of 8e in 75 mL of dry tetrahydrofuran cooled to 0° C. was added dropwise 28 mL (2.0 M in tetrahydrofuran) of butylmagnesium chloride. The reaction solution was allowed to warm to room temperature and stirred for 144 h under nitrogen. The reaction solution was cooled to 0° C., and 200 mL of a 5% aqueous hydrochloric acid solution was added dropwise. After stirring overnight at room temperature, the reaction mixture was quenched with a saturated aqueous sodium bicarbonate solution, and the product was extracted with methylene chloride, dried (Na$_2$SO$_4$), and filtered. The solvent was removed, and the resulting residue was dried briefly under high vacuum to give 5.71 g of a brown solid. Purification by flash chromatography (silica, 3:1 hexane-methylene chloride) gave 4.30 g (80%) of 9bb as a light brown solid. $^1$H NMR (CDCl$_3$) δ 8.02 (s, 1H), 7.80-7.76 (dd, 1H), 7.54 (d, 1H), 2.92 (t, 2H), 1.77-1.63 (m, 2H), 1.48-1.33 (m, 2H), 0.95 (t, 3H).

Step 2. 2-Bromo-3',4'-dichloropentanophenone (10bb). To a solution of 4.23 g (0.018 mol) of 9bb in 70 mL of methylene chloride was added ten drops of bromine. After stirring at room temperature under nitrogen for several minutes, the characteristic red color of bromine disappeared indicating initiation of the reaction. The remainder of the 1 mL (18.30 mmol) of bromine was added dropwise, and the reaction solution was allowed to stir at room temperature under nitrogen for 9.5 h. The reaction solution was quenched and brought to pH 9 with a saturated aqueous solution of sodium bicarbonate and concentrated ammonium hydroxide. The product was extracted with methylene chloride, dried (Na$_2$SO$_4$), and filtered. The solvent was removed, and the resulting residue was dried briefly under high vacuum to give 5.70 g (100%) of 10bb as an orange oil. $^1$H NMR (CDCl$_3$) δ 8.09 (s, 1H), 7.86-7.82 (dd, 1H), 7.55 (d, 1H), 5.02 (t, 1H), 2.19-2.10 (m, 2H), 1.60-1.42 (m, 2H), 0.99 (t, 3H).

Step 3. 2-(tert-Butylamino)-3',4'-dichloropentanophenone (2bb) Fumarate. To a pressure tube was transferred 5.56 g (0.018 mol) of 10bb with a minimal amount of methylene chloride. Most of the methylene chloride was removed via positive nitrogen flow, 28 mL (269.01 mmol) of tert-butylamine was added in one portion, and the tube was sealed and placed in an oil bath heated to 70° C. After stirring at 70° C. for 3 h, tert-butylamine began to escape from the reaction tube, and the reaction mixture was allowed to cool to room temperature. The reaction mixture was quenched and brought to a pH of 10 with a saturated aqueous solution of sodium bicarbonate, and the product was extracted with methylene chloride, dried ($Na_2SO_4$), and filtered. The solvent was removed, and the resulting residue was dried briefly under high vacuum to give 5.0 g of an orange oil which TLC (9:1:20 $Et_2O$-$Et_3N$-hexane) showed to be an 80/20 mixture of starting material/product. The mixture was submitted to the original reaction conditions for 24 h using 19 mL (179.30 mmol) of tert-butylamine and to the original work-up conditions to give 5.61 g of an orange oil. Purification by flash chromatography (silica, 9:1:60 $Et_2O$-$Et_3N$-hexane) gave 2.44 g (45%) of 2bb as an orange oil. $^1$H NMR ($CDCl_3$) δ 8.08 (s, 1H), 7.85-7.80 (dd, 1H), 7.58 (d, 1H), 4.10-4.05 (m, 1H), 1.54-1.26 (m, 4H), 1.01 (s, 9H), 0.94-0.88 (m, 3H). To a solution of 2.27 g (0.0075 mol) of 2bb in methylene chloride-methanol was added 0.87 g (0.0075 mol) of fumaric acid. The reaction solution was allowed to stir for 15 min, and the solvent was removed in vacuo leaving a white solid. Recrystallization from methanol-$Et_2O$ afforded 1.86 g of 2bb•fumarate as a white solid: mp 177-179° C. $^1$H NMR ($CD_3OD$) δ 8.35 (s, 1H), 8.12-8.08 (dd, 1H), 7.81 (d, 1H), 5.17 (t, 1H), 1.96-1.90 (m, 2H), 1.34 (bs, 10H), 0.89 (t, 3H). Anal. ($C19H_{25}Cl_2NO_5$) C, H, N.

a) Synthesis of Compounds for Comparison

Synthesis of 2-(N-tert-Butylamino)propiophenone (2b)

Step 1. 2-Bromopropiophenone (10b). To a solution of 5 g (0.037 mol) of priopiophenone, 9b, in 50 mL of $CH_2Cl_2$ was added 1.92 mL (37.3 mmol) of $Br_2$ over 15 min. The solution was allowed to stir for 15 min. The reaction mixture was washed with 40 mL of saturated $NaHCO_3$, 40 mL of 1 N $Na_2S_2O_3$, 40 mL of brine, dried ($Na_2SO_4$), and concentrated to afford 7.9 g (90%) of 10b as a pale yellow oil. $^1$H NMR ($CDCl_3$) δ 8.08-8.02 (d, 2H), 7.63-7.58 (t, 1H), 7.56-7.47 (t, 2H), 5.40-5.24 (q, 1H), 1.97-1.90 (d, 3H).

Step 2. 2-(N-tert-Butylamino)propiophenone (2b) Fumarate. In a 100 mL round-bottom flask was dissolved 6.27 g (0.027 mol) of 10b in 42.2 mL (402 mmol) of tert-butylamine. The flask was sealed with a rubber septum and stirred for 2 h. The reaction mixture was concentrated in vacuo, the residue was taken up in 50 mL of 2 N HCl, and 50 mL of $Et_2O$ was added. The acidic layer was collected, basified to pH 11 with 5 N NaOH and extracted with 3×25 mL of $CH_2Cl_2$. The combined organic layers were washed with 50 mL of brine, dried ($Na_2SO_4$), and filtered. The solvent was removed to afford 3.32 g (43%) of 2b as a pale yellow oil. The fumarate salt was prepared by adding one equivalent of fumaric acid to an $Et_2O$ solution of 2b. Recrystallization of the salt from $CH_3OH$-$Et_2O$ afforded a white crystalline solid; mp 183-185° C. $^1$H NMR ($CDCl_3$) δ 8.07-8.02 (d, 2H), 7.61-7.57 (t, 2H), 7.55-7.48 (t, 2H), 4.45-4.34 (q, 1H), 1.32-1.30 (d, 3H), 1.16-1.04 (s, 9H). Anal. ($C_{17}H_{23}NO_5$) C, H, N.

Synthesis of 2-(tert-Butylamino)-3'-fluoropropiophenone (2c)

Step 1. 2-Bromo-3'-fluoropropiophenone (10c). To a solution of 2.28 g (0.015 mol) of 3-fluoropropiophenone, 9c, in 60 mL of $CH_2Cl_2$ was added ten drops of bromine After stirring at room temperature under nitrogen for several min, the characteristic red color of bromine disappeared, indicating initiation of the reaction. The remainder of the 0.7 mL (15 mmol) of bromine was added drop-wise, and the reaction solution was allowed to stir at room temperature under nitrogen for 11 h. The reaction solution was quenched and brought to a pH of 9 with a saturated sodium bicarbonate solution. The product was extracted with methylene chloride, dried ($Na_2SO_4$), and filtered. The solvent was removed, and the resulting residue was dried briefly under high vacuum to give 3.39 g of a clear oil. Purification by flash chromatography (silica, 5:1 hexane-methylene chloride) gave 2.87 g (83%) of 10c as a clear oil. $^1$H NMR ($CDCl_3$) δ 7.82-7.73 (dd, 1H), 7.69 (d, 1H), 7.52-7.43 (m, 1H), 7.33-7.29 (m, 1H), 5.30-5.18 (q, 1H), 1.91 (d, 3H).

Step 2. 2-(tert-Butylamino)-3'-fluoropropiophenone (2c) Fumarate. To a sealable reaction tube was transferred 2.87 g (0.019 mol) of 10c with a minimal amount of methylene chloride. Most of the methylene chloride was removed via positive nitrogen flow, 13 mL (124.20 mmol) of tert-butylamine was added in one portion, and the tube was sealed and placed in an oil bath heated to 55° C. After stirring at 55° C. for 17 h, the reaction mixture was allowed to cool to room temperature, was quenched, and was brought to pH 10 with a saturated sodium bicarbonate solution. The product was extracted with methylene chloride, dried ($Na_2SO_4$), and filtered. The solvent was removed, and the resulting residue was dried briefly under high vacuum to give 2.74 g of a pale yellow oil. Purification by flash chromatography (silica, 9:1:50 $Et_2O$-$Et_3N$-hexane) gave 1.94 g (70%) of 2c as a clear oil. $^1$H NMR ($CDCl_3$) δ 7.80-7.77 (dd, 1H), 7.69 (d, 1H), 7.53-7.44 (m, 1H), 7.32-7.29 (m, 1H), 4.35-4.26 (q, 1H), 1.27 (d, 3H), 1.05 (s, 9H). To a solution of 1.94 g (0.0087 mol) of 2c in methanol was added 1.00 g (0.0087 mol) of fumaric acid. The reaction solution was allowed to stir for 15 min, and the solvent was removed in vacuo leaving a white solid. Recrystallization from methanol/$Et_2O$ afforded 2.52 g of 2c•fumarate as a white solid: mp 173-175° C. $^1$H NMR ($CD_3OD$) δ 8.04-8.00 (dd, 1H), 7.94-7.89 (dd, 1H), 7.69-7.62 (m, 1H), 7.56-7.52 (m, 1H), 5.27-5.18 (q, 1H), 1.59 (d, 3H), 1.36 (s, 9H). Anal. ($C_{17}H_{22}FNO_5$) C, H, N.

Synthesis of 2-(N-tert-Butylamino)-3'-bromopropiophenone (2d)

Step 1. 2-Bromo-3'-bromopropiophenone (10d). 3'-Bromopropiophenone 9d (8.0 g, 0.038 mol) was dissolved in 30 mL of methanol at room temperature in a 250 mL flask equipped with a magnetic stir bar. Bromine (9.05 g, 0.057 mol) was added over a period of 10 min. Twenty drops of 48% hydrobromic acid were added, and the reaction mixture was stirred under $N_2$. After 72 h, the solvent and excess reagents were removed under reduced pressure to give 11.66 g of an oil. The dark orange oil was purified by flash chromatography (4:1 hexane-methylene chloride) to afford 6.99 g (64%) of 10d as a pale yellow oil. $^1$H NMR ($CD_3OD$) δ 8.16 (s, 1H), 8.05-7.98 (d, 1H), 7.80-7.75 (d, 1H), 7.47-7.40 (t, 1H), 5.60-5.50 (q, 1H), 1.87-1.83 (d, 3H).

Step 2. 2-(N-tert-Butylamino)-3'-bromopropiophenone (2d) Fumarate. Intermediate 10d (6.99 g, 0.0024 mol) and tert-butylamine (25.2 mL, 240 mmol) were placed in a pressure tube equipped with a magnetic stir bar. The tube was sealed and heated at 80° C. with an oil bath. After 2 h, the mixture was transferred to a separatory funnel, saturated sodium bicarbonate solution was added, and the aqueous layer was extracted with methylene chloride. The organic layer was dried (Na$_2$SO$_4$) and filtered. The solvent was removed under reduced pressure. The resulting oil was dissolved in methanol, and the solvent was removed under reduced pressure to afford 6.42 g (94%) of 2d as a pale yellow oil. $^1$H NMR (CD$_3$OD) δ 8.20 (s, 1H), 8.10-8.05 (d, 1H), 7.83-7.78 (d, 1H), 7.50-7.45 (t, 1H), 4.55-4.45 (q, 1H), 1.28-1.23 (d, 3H), 1.06 (s, 9H). Amine 2d was converted to a fumarate salt using the procedure described for 2b. Recrystallization of the salt from methanol and Et$_2$O afforded 1.75 g of 2d•fumarate as white crystals: mp 174° C. (dec). $^1$H NMR (CD$_3$OD) δ 8.32 (s, 1H), 8.18-8.14 (d, 1H), 7.95-7.90 (d, 1H), 7.59-7.51 (t, 1H), 6.69 (s, 2H), 5.28-5.19 (q, 1H), 1.60-1.56 (d, 3H), 1.36 (s, 9H). Anal. (C$_{17}$H$_{22}$BrNO$_5$) C, H, N.

Synthesis of 2-(N-tert-Butylamino)-3'-methylpropiophenone

Step 1. 3'-Methylpropiophenone (9e). 3-Methylbenzonitrile 8a (3.25 g, 0.028 mol) and dry THF (75 mL) were placed in a 250 mL flask equipped with a magnetic stir bar. The flask was cooled to 0° C. using an ice-water bath. Ethyl magnesium bromide (33.3 mL, 1 M in THF) was added dropwise over 10 min. The solution was stirred for 30 min and warmed to room temperature. After stirring under N$_2$ for 72 h, 30 mL of crushed ice was added. The mixture was transferred to a separatory funnel, and the aqueous layer was extracted with Et$_2$O. The organic layer was dried (Na$_2$SO$_4$) and filtered. The solvent was removed under reduced pressure to afford 3.86 g (94%) of 9e as a clear oil. $^1$H NMR (CDCl$_3$) δ 7.78-7.71 (m, 2H), 7.50-7.32 (m, 2H), 2.40 (s, 3H), 3.05-2.95 (q, 2H), 1.25-1.19 (t, 3H).

Step 2. 2-Bromo-3'-methylpropiophenone (10e). Ketone 9e (3.5 g, 0.024 mol) and methylene chloride (200 mL) were placed in a 500-mL flask equipped with a magnetic stir bar. The solution was stirred under N$_2$ and bromine (1.21 mL, 23.6 mmol) was syringed into flask. (Note: a small amount of bromine was added to initiate the reaction; the color dissipated as reaction occurs; after reaction mixture was initiated, the remaining bromine was added over 10 min). A needle was placed in the septa to allow the hydrogen bromide gas formed in the reaction mixture to escape from the flask. After stirring for 10 h, the solution was transferred to a separatory funnel. Saturated sodium bicarbonate solution was added to basify the reaction. The mixture was filered, and the aqueous layer was extracted with methylene chloride. The organic layer was dried (Na$_2$SO$_4$) and filtered. The solvent was removed under reduced pressure to give 5.38 g of an oil. The dark orange oil was purified by flash chromatography on silica gel (3:1 hexane-methylene chloride) to afford 3.14 g (59%) of 10e as a pale yellow oil. $^1$H NMR (CDCl$_3$) δ 7.86-7.79 (m, 2H), 7.42-7.32 (m, 2H), 5.35-5.25 (q, 1H), 2.42 (s, 3H), 1.93-1.89 (d, 3H).

Step 3. 2-(N-tert-Butylamino)-3'-methylpropiophenone (2e) Fumarate. Compound 10e (3.0 g, 0.013 mol) and tert-butylamine (13.88 mL, 130 mmol) were placed in a pressure tube equipped with a magnetic stir bar. The tube was sealed and heated at 70° C. with an oil bath. After 2 h, the mixture was transferred to a separatory funnel. Water (50 mL) and ammonium hydroxide (5 drops) were added, and the aqueous layer was extracted with methylene chloride. The organic layer was dried (Na$_2$SO$_4$) and filtered. The solvent was removed under reduced pressure. The oil was dissolved in methanol, and the methanol was removed under reduced pressure to afford 2.83 g (98%) of 12e as a pale yellow oil. $^1$H NMR (CDCl$_3$) δ 7.81-7.76 (m, 2H), 7.41-7.35 (m, 2H), 4.40-4.30 (q, 1H), 2.44 (s, 3H), 1.29-1.23 (d, 3H), 1.05 (s, 9H). Amine 2e was converted to a fumarate salt using the procedure described for 2b. Recrystallization of the salt from methanol and Et$_2$O afforded 3.43 g of 2e•fumarate as white crystals: mp 172-174° C. (dec). $^1$H NMR (CD$_3$OD) δ 8.00-7.93 (m, 2H), 7.61-7.57 (d, 1H), 7.53-7.46 (t, 1H), 6.68 (s, 2H), 5.29-5.19 (q, 1H), 2.46 (s, 3H), 1.60-1.55 (d, 3H), 1.36 (s, 9H). Anal. (C$_{18}$H$_{25}$NO$_5$.0.25 H$_2$O)C, H, N.

Synthesis of 2-(N-tert-Butylamino)-4'-chloropropiophenone

Step 1. 2-Bromo-4'-chloropropiophenone (10f). 4'-Chloropropiophenone 9f (4.58 g, 0.027 mol) was dissolved in 30 mL of methanol at room temperature in a 250 mL flask equipped with a magnetic stir bar. Bromine (1.67 mL, 32.6 mmol) was added over a period of 10 min. Seven drops of 48% hydrobromic acid were added, and the reaction mixture was stirred under N$_2$. After 110 h, the solution was transferred to a separatory funnel, saturated sodium bicarbonate solution was added, and the aqueous layer was extracted with methylene chloride. The organic layer was dried (Na$_2$SO$_4$) and filtered. The solvent was removed under reduced pressure to give 6.60 g (98%) of 10f as an orange oil. $^1$H NMR (CDCl$_3$) δ 8.00-7.94 (d, 2H), 7.50-7.44 (d, 2H), 5.27-5.19 (q, 1H), 1.92-1.89 (d, 3H).

Step 2. 2-(N-tert-Butylamino)-4'-chloropropiophenone (2f) Fumarate. Intermediate 10f (6.60 g, 0.027 mol) and tert-butylamine (28.02 mL, 267 mmol) were placed in a pressure tube equipped with a magnetic stir bar. The tube was sealed and heated at 75° C. with an oil bath. After 1.5 h, the mixture was transferred to a separatory funnel, saturated sodium bicarbonate solution was added, and the aqueous layer was extracted with methylene chloride. The organic layer was dried (Na$_2$SO$_4$) and filtered. The solvent was removed under reduced pressure. The oil was dissolved in methanol and the solvent was removed under reduced pressure to afford 6.21 g (97%) of 2f as a light yellow oil. $^1$H NMR (CD$_3$OD) δ 8.10-8.04 (d, 2H), 7.59-7.53 (d, 2H), 4.55-4.46 (q, 1H), 1.27-1.25 (d, 3H), 1.06 (s, 9H). Amine 2f was converted to a fumarate salt using the procedure described for 2b. Recrystallization of the salt from methanol afforded 3.92 g of 2f•fumate as white crystals: mp 197° C. (dec). $^1$H NMR (CD$_3$OD) δ 8.18-8.13 (d, 2H), 7.67-7.62 (d, 2H), 5.25-5.16 (q, 1H), 1.60-1.56 (d, 3H), 1.36 (s, 9H). Anal. (C$_{17}$H$_{22}$ClNO$_5$) C, H, N.

Synthesis of 2-(N-tert-Butylamino)-4'-bromopropiophenone (2g)

Step 1. 2-Bromo-4'-bromopropiophenone (10g). A flask was charged with 4'-Bromopropiophenone (5.0 g, 0.023 mol) and 25 ml of dichloromethane and 1M ethereal HCl (0.25 mL, 0.00025 mol). A solution of bromine (7.6 ml, 0.148 mol total including the drop added earlier) and dichloromethane (25 ml) was added. A small amount of bromine was added initially to catalyze the reaction. After the reaction started, the remaining bromine was added over a 30 min period. After stirring for 18 h, the reaction mixture was poured into a saturated solution of sodium bicarbonate (50 ml) and solid sodium bicarbonate added until slightly alkaline. The layers were separated and the organic layer was washed with brine (50 ml), dried over sodium sulfate, and concentrated to give 35.1 g (96%) of 10 g of yellow oil. $^1$H NMR (CDCl$_3$) δ 7.91-7.86 (d, 2H), 7.65-7.60 (d, 2H), 5.26-5.19 (q, 1H), 1.92-1.89 (d, 3H).

Step 2. 2-(N-tert-Butylamino)-4'-bromopropiophenone (2g) Fumarate. Intermediate 10g (8.04 g, 0.028 mol) and tert-butylamine (28.9 mL, 275 mmol) were placed in a pressure tube equipped with a magnetic stir bar. The tube was sealed and heated at 80° C. with an oil bath. After 2 h, the mixture was transferred to a separatory funnel, saturated sodium bicarbonate solution was added, and the aqueous layer was extracted with methylene chloride. The organic layer was dried ($Na_2SO_4$) and filtered. The solvent was removed under reduced pressure. The oil was dissolved in methanol and the solvent was removed under reduced pressure to afford 7.53 g (96%) of 2g as a yellow oil. $^1$H NMR ($CD_3OD$) δ 8.01-7.96 (d, 2H), 7.75-7.70 (d, 2H), 4.54-4.45 (q, 1H), 1.25-1.21 (d, 3H), 1.06 (s, 9H). Amine 2g was converted to a fumarate salt using the procedure described for 2b. Recrystallization of the salt from methanol afforded 6.05 g of 2g•fumarate as white crystals: mp 206° C. (dec). $^1$H NMR ($CD_3OD$) δ 8.10-8.05 (d, 2H), 7.84-7.78 (d, 2H), 6.69 (s, 2H), 5.24-5.15 (q, 1H), 1.59-1.56 (d, 3H), 1.35 (s, 9H). Anal. ($C_{17}H_{22}BrNO_5$) C, H, N.

Synthesis of
2-(N-tert-Butylamino)-4'-methylpropiophenone (2h)

Step 1. 2-Bromo-4'-methylpropiophenone (10h). 4'-Methylpropiophenone 9h (4.0 g, 0.027 mol) and methylene chloride (100 mL) were placed in a 250-mL flask equipped with a magnetic stir bar. The solution was stirred under $N_2$ and bromine (1.38 mL, 27.0 mmol) was syringed into flask. (Note: a small amount of bromine was added to initiate the reaction; the color dissipated as the reaction occurs; after the reaction initiated, the remaining bromine was added over 10 min.). A needle was placed in the septa to allow the hydrogen bromide gas formed in the reaction to escape from the flask. After stirring for 10 h, saturated sodium bicarbonate solution was added to basify the reaction. When the pH was 9, the aqueous layer was extracted with methylene chloride. The organic layer was dried ($Na_2SO_4$) and filtered. The solvent was removed under reduced pressure to give 6.33 g of 10 h as a white solid. $^1$H NMR ($CDCl_3$) δ 7.94-7.89 (d, 2H), 7.30-7.25 (d, 2H), 5.33-5.23 (q, 1H), 2.42 (s, 3H), 1.91-1.87 (d, 3H).

Step 2. 2-(N-tert-Butylamino)-4'-methylpropiophenone (2h) Fumarate. Compound 10h (6.0 g, 0.026 mol) and tert-butylamine (27.76 mL, 260 mmol) were placed in a pressure tube equipped with a magnetic stir bar. The tube was sealed and heated at 80° C. with an oil bath. After 2 h, the mixture was transferred to a separatory funnel. Saturated sodium bicarbonate solution was added, and the aqueous layer was extracted with methylene chloride. The organic layer was dried ($Na_2SO_4$) and filtered. The solvent was removed under reduced pressure. The oil was dissolved in methanol and the solvent was removed under reduced pressure to afford 5.60 g (97%) of 2h as a light orange oil. $^1$H NMR ($CDCl_3$) δ 7.94-7.89 (d, 2H), 7.32-7.28 (d, 2H), 4.40-4.30 (q, 1H), 2.42 (s, 3H), 1.29-1.25 (d, 3H), 1.05 (s, 9H). Amine 2h was converted to a fumarate salt using the procedures] described for 2b. Recrystallization of the salt from methanol and $Et_2O$ afforded 4.50 g of 2h•fumarate as white crystals: mp 193-195° C. (dec.) $^1$H NMR ($CD_3OD$) δ 8.08-8.04 (d, 2H), 7.45-7.41 (d, 2H), 6.68 (s, 2H), 5.24-5.16 (q, 1H), 2.46 (s, 3H), 1.58-1.55 (d, 3H), 1.35 (s, 9H). Anal. ($C_{18}H_{25}NO_5$) C, H, N.

Synthesis of 2-tert-Butylamino-3',4'-difluoropropiophenone (2i)

Step 1. 2-Bromo-3',4'-difluoropropiophenone (10i). To a solution of 2 g (0.012 mol) of 3,4-difluoropropiophenone, 9i, in 20 mL of methanol under $N_2$ was added drop-wise 0.73 mL (14.2 mmol) of bromine A few drops of 48% hydrobromic acid were added to initiate the reaction, and the reaction mixture was allowed to stir at room temperature for 117 h. The reaction mixture was quenched with a saturated sodium bicarbonate solution. The product was extracted with ethyl acetate, dried ($Na_2SO_4$), and filtered. The solvent was removed, and the resulting residue was dried briefly on a high vacuum pump to afford 2.97 g (101%) of 10i as a clear oil. $^1$H NMR ($CDCl_3$) δ 7.92-7.79 (m, 2H), 7.38-7.13 (m, 1H), 5.22-5.14 (q, 1H), 1.90 (d, 3H).

Step 2. 2-tert-Butylamino-3',4'-difluoropropiophenone (2i) Fumarate. To a sealable reaction tube was transferred 2.31 g (0.0093 mol) of 10i with a minimal amount of methylene chloride. To the solution was added 9.7 mL (92.70 mmol) of tert-butylamine, the tube was sealed and heated to 75° C. in an oil bath. After stirring for 3 h, the reaction mixture was quenched with a saturated sodium bicarbonate solution, and the product was extracted with methylene chloride, dried ($Na_2SO_4$), and filtered. The solvent was removed, and the resulting residue was dried briefly on a high vacuum pump to give 2.25 g (100%) of 2i as a yellow oil. Purification by flash chromatography (silica, 9:1:20 $Et_2O$-$Et_3N$-hexane) afforded 1.42 g (52%) of 2l as a yellow solid. $^1$H NMR ($CDCl_3$) δ 7.90-7.79 (m, 2H), 7.31-7.30 (m, 1H), 4.28-4.26 (q, 1H), 1.27 (d, 3H), 1.04 (s, 9H). To a solution of 1.35 g (0.006 mol) of 2i in methanol was added 649 mg (5.59 mmol) of fumaric acid. The reaction solution was allowed to stir at room temperature for 30 min, and the solvent was removed in vacuo leaving an off-white solid which was recrystallized from methanol and $Et_2O$ to afford 1.29 g of 2i•fumarate as white crystals: mp 185° C. $^1$H NMR ($CD_3OD$) δ 8.18-8.05 (m, 2H), 7.60-7.49 (m, 1H), 5.24-5.15 (q, 1H), 1.58 (d, 3H), 1.35 (s, 9H). Anal. ($C_{17}H_{21}F_2NO_5$) C, H, N.

Synthesis of 2-(N-tert-Butylamino)-3',4'-dichloropropiophenone (2j)

Step 2. 2-Bromo-3',4'-dichloropropiophenone (10j). 3',4'-Dichloropropiophenone 9j (3.94 g, 0.019 mol) was dissolved in 30 mL of methanol at room temperature in a 250 mL flask equipped with a magnetic stir bar. Bromine (1.19 mL, 23.0 mmol) was added over a period of 10 min Seven drops of 48% hydrobromic acid was added, and the reaction mixture was stirred under $N_2$. After 110 h, the solution was transferred to a separatory funnel. Saturated sodium bicarbonate solution was added, and the aqueous layer was extracted with methylene chloride. The organic layer was dried ($Na_2SO_4$) and filtered. The solvent was removed under reduced pressure to give 5.47 g (100%) of 10j as an orange oil. $^1$H NMR ($CDCl_3$) δ 8.10 (s, 1H), 7.87-7.83 (d, 1H), 7.56-7.52 (d, 1H), 5.22-5.14 (q, 1H), 1.92-1.89 (d, 3H).

Step 3. 2-(N-tert-Butylamino)-3',4'-dichloropropiophenone (2j) Fumarate. Intermediate 10i (5.47 g, 0.019 mol) and tert-butylamine (20.39 mL, 19 mmol) were placed in a pressure tube equipped with a magnetic stir bar. The tube was sealed and heated at 75° C. with an oil bath. After 1.5 h, the mixture was transferred to a separatory funnel, saturated sodium bicarbonate solution was added, and the aqueous layer was extracted with methylene chloride. The organic layer was dried ($Na_2SO_4$) and filtered. The solvent was removed under reduced pressure. The oil was dissolved in methanol, and the solvent was removed under reduced pressure to afford 5.10 g (96%) of 2j as a pale yellow oil. $^1$H NMR ($CD_3OD$) δ 8.21 (s, 1H), 8.04-8.00 (d, 1H), 7.74-7.70 (d, 1H), 4.54-4.45 (m, 1H), 1.24-1.21 (d, 3H), 1.06 (s, 9H).

Amine 2j was converted to a fumarate salt using the procedure described for 2b. Recrystallization of the salt from methanol afforded 1.99 g of 2j•fumarate as white crystals: mp 196-197° C. (dec). $^1$H NMR (CD$_3$OD) δ 8.35 (s, 1H), 8.11-8.07 (d, 1H), 7.82-7.78 (d, 1H), 6.68 (s, 2H), 5.24-5.15 (q, 1H), 1.58-1.55 (d, 3H), 1.35 (s, 9H). Anal. (C$_{17}$H$_{22}$Cl$_2$NO$_5$) C, H, N.

Synthesis of 2-(N-tert-Butylamino)-3'-chloro-4'-methylpropiophenone (2k)

Step 1. 3'-Chloro-4'-methylpropiophenone (9k). To a solution of 2.5 g (0.017 mol) of 3-chloro-4-methylbenzonitrile, 8b, in 100 mL of dry THF cooled to 0° C. under N$_2$ was added 33.0 mL (33.0 mmol) of 1 M EtMgBr/THF via syringe over 5 min. The reaction mixture was allowed to warm to room temperature and was stirred for 72 h. The reaction mixture was cooled to 0° C., and 75 mL of 1 N HCl was slowly added. The mixture was stirred for 1.5 h at 0° C., diluted with 100 mL of H$_2$O, and extracted with 3×75 mL of Et$_2$O. The combined organic layers were washed with 50 mL of saturated NaHCO$_3$ solution, 50 mL of brine, dried (MgSO$_4$), and filtered. The solvent was removed to afford 2.96 g (98%) of 9k as a pale yellow solid. $^1$H NMR (CDCl$_3$) δ 8.21 (s, 1H), 7.87-7.3 (d, 1H), 7.39-7.20 (d, 1H), 3.00-2.91 (q, 2H), 2.43 (s, 3H), 1.28-1.13 (t, 3H).

Step 2. 2-Bromo-3'-chloro-4'-methylpropiophenone (10k). To a solution of 1.5 g (0.008 mol) of 9k in 40 mL of CH$_2$Cl$_2$ was added 1.31 g (0.008 mol) of Br$_2$ over 15 min. The solution was allowed to stir for 16 h and diluted with 60 mL of saturated NaHCO$_3$ solution, and the organic layer was separated. The aqueous layer was extracted with 2×50 mL of CH$_2$Cl$_2$. The combined organic layers were dried (Na$_2$SO$_4$) and filtered. The solvent was removed to afford an orange oil. Chromatography (200 g SiO$_2$; petroleum Et$_{20}$, 1:1 pet. Ether-Et$_2$O) afforded 1.4 g (65%) of 10k as a slightly off-white solid. $^1$H NMR (CDCl$_3$) δ 8.06-8.00 (s, 1H), 7.88-7.79 (d, 1H), 7.43-7.30 (d, 1H), 5.29-5.18 (q, 2H), 2.45 (s, 3H), 1.97-1.88 (d, 3H).

Step 3. 2-(N-tert-Butylamino)-3'-chloro-4'-methylpropiophenone (2k) Fumarate. In a 25 mL pressure tube equipped with a stir bar was dissolved 1.25 g (0.0048 mol) of 10k in 7.53 mL (71.7 mmol) of tert-butylamine. The tube was sealed and heated to 80° C. on an oil bath. After 2.5 h, the reaction mixture was cooled and taken up in 20 mL of Et$_2$0 and 20 mL of saturated NaHCO$_3$ solution. The organic layer was separated, and the aqueous layer was extracted with 2×10 mL of Et$_2$O. The combined organic layers were washed with 20 mL of saturated NaHCO$_3$ solution, 20 mL of brine, dried (MgSO$_4$), and filtered. The solvent was removed to afford 1.2 g (99%) of slightly impure 2k as a yellow oil. The fumarate salt was prepared as described for 2b. Recrystallization from MeOH-EtOAc to afford 1.24 g of 2k•fumarate as a white crystalline solid: mp 196-198° C. $^1$H NMR (d$_6$-DMSO) δ 8.13 (s, 1H), 8.06-8.00 (d, 1H), 7.65-7.55 (d, 1H), 6.58 (s, 2H), 4.69-4.58 (q, 2H), 2.51 (s, 2H), 2.42 (s, 3H), 1.20-1.17 (d, 3H), 1.04 (s, 9H). Anal. (C$_{18}$H$_{24}$ClNO$_5$) C, H, N.

Synthesis of 2-(N-tert-Butylamino)-4'-bromo-5'-methylpropiophenone (2l)

Step 1. 2-Bromo-4'-bromo-5'-methylpropiophenone (10l). To a solution of 1.5 g (0.0082 mol) of 4-bromo-5-methylpropiophenone, 9l, in 40 mL of CH$_2$Cl$_2$ was added 0.32 mL (6.27 mmol) of Br$_2$ over 15 min. The solution was allowed to stir for 15 min. The reaction mixture was washed with 3×40 mL of saturated NaHCO$_3$ solution, 40 mL of brine, dried (Na$_2$SO$_4$), and concentrated to afford 1.9 g (99%) of 10l as a pale yellow oil. $^1$H NMR (CDCl$_3$) δ 7.88 (s, 1H), 7.70-7.61 (m, 2H), 5.31-5.20 (q, 2H), 2.47 (s, 3H), 1.97-1.82 (d, 3H).

Step 2. 2-(N-tert-Butylamino)-4'-bromo-5'-methylpropiophenone (2l) Fumarate. In a 25 mL pressure tube equipped with a stir bar was dissolved 1.90 g (0.062 mol) of 10l in 9.79 mL (93.2 mmol) of tert-butylamine. The tube was sealed and heated to 60° C. on an oil bath. After 2.5 h, the cooled reaction mixture was poured into 50 mL of Et$_2$O washed with 3×50 mL of saturated NaHCO$_3$ solution, 50 mL of brine, dried (MgSO$_4$), and filtered. The solvent was removed to afford 1.8 g (97%) of slightly impure 2l as an orange oil. The fumarate salt was prepared as described for 2b, recrystallized twice from MeOH to afford 1.05 g of 2l•fumarate as a white crystalline solid: mp 198-200° C. $^1$H NMR (d$_6$-DMSO) δ 8.09 (s, 1H), 7.88-7.85 (d, 1H), 7.80-7.73 (d, 1H), 6.58 (s, 2H), 4.70-4.53 (q, 2H), 250-2.45 (s, 1H), 2.38-2.36 (s, 3H), 1.25-1.20 (d, 3H), 1.04 (2, 9H). Anal. (C$_{18}$H$_{24}$BrNO$_5$) C, H, N.

Synthesis of 2-(tert-Butylamino)-3',5'-difluoropropiophenone (2m)

Step 1. 2-Bromo-3',5'-difluoropropiophenone (10m). To a solution of 3.00 g (0.018 mol) of 3,5-difluoropropiophenone, 9m, in 70 mL of methylene chloride was added 10 drops of bromine. After stirring at room temperature under nitrogen for several minutes, the characteristic red color of bromine disappeared indicating initiation of the reaction. The remainder of the 0.9 mL (17.63 mmol) of bromine was added dropwise, and the reaction solution was allowed to stir at room temperature under nitrogen overnight. The reaction solution was quenched and brought to a pH of 9 with a saturated sodium bicarbonate solution. The product was extracted with methylene chloride, dried (Na$_2$SO$_4$), and filtered. The solvent was removed, and the resulting residue was dried briefly under high vacuum to give 4.36 g (99%) of 10m as a clear oil. $^1$H NMR (CDCl$_3$) δ 7.57-7.49 (bdd, 2H), 7.09-7.01 (m, 1H), 5.30-5.10 (q, 1H), 1.91 (d, 3H).

Step 2. 2-(tert-Butylamino)-3',5'-difluoropropiophenone (2m) Fumarate. To a sealable reaction tube was transferred 4.36 g (0.018 mol) of 10m with a minimal amount of methylene chloride. Most of the methylene chloride was removed via positive nitrogen flow, 19 mL (175.05 mmol) of tert-butylamine was added in one portion, and the tube was sealed and placed in an oil bath heated to 80° C. After stirring at 80° C. for 2 h, the reaction mixture was allowed to cool to room temperature, quenched, and brought to a pH of 10 with a saturated sodium bicarbonate solution. The product was extracted with methylene chloride, dried (Na$_2$SO$_4$), and filtered. The solvent was removed, and the resulting residue was dried briefly under high vacuum to give 4.09 g of an orange oil. Purification by flash chromatography (silica, 9:1:50 Et$_2$O-Et$_3$N-hexane) gave 3.29 g (78%) of 2m as a yellow oil. $^1$H NMR (CDCl$_3$) δ 7.54-7.50 (dd, 2H), 7.08-7.01 (m, 1H), 4.27-4.22 (q, 1H), 1.27 (d, 3H), 1.05 (s, 9H). To a solution of 3.22 g (0.013 mmol) of 2m in methanol was added 1.54 g (0.013 mol) of fumaric acid. The reaction solution was allowed to stir for 15 min, and the solvent was removed in vacuo leaving a white solid. Recrystallization from methanol-Et$_2$O afforded 4.00 g of 2m•fumarate as a white solid: mp 170-172° C. $^1$H NMR (CD$_3$OD) δ 7.84-7.81 (dd, 2H), 7.46-7.39 (m, 1H), 5.21-5.15 (q, 1H), 1.58 (d, 3H), 1.35 (s, 9H). Anal. (C$_{17}$H$_{21}$F$_2$NO$_5$) C, H, N.

Synthesis of 2-(tert-Butylamino)-3',5'-dichloropropiophenone (2n)

Step 1. 3',5'-Dichloropropiophenone (9n). To a solution of 5.24 g (0.031 mol) of 3,5-dichlorobenzonitrile, 8c, in 100 mL of dry tetrahydrofuran cooled to 0° C. was added dropwise 35 mL (2.0 M in Et$_2$O) of ethylmagnesium chloride. The reaction solution was allowed to warm a to room temperature and stir at room temperature for 74 h under nitrogen. The reaction solution was cooled to 0° C., and 250 mL of a 5% aqueous hydrochloric acid solution was added dropwise. After stirring overnight at room temperature, the reaction mixture was quenched with a saturated aqueous sodium bicarbonate solution and basified to pH 11 with concentrated ammonium hydroxide. The product was extracted with methylene chloride, dried (Na$_2$SO$_4$), and filtered. The solvent was removed, and the resulting residue was dried briefly under high vacuum to give 6.21 g of a brown solid. Purification by flash chromatography (silica, 5:1 hexane-methylene chloride) gave 4.94 g (80%) of 9n as a white non-crystalline solid. $^1$H NMR (CDCl$_3$) δ 7.81 (s, 2H), 7.54 (s, 1H), 3.00-2.92 (q, 2H), 1.23 (t, 3H).

Step 2. 2-Bromo-3',5'-dichloropropiophenone (10n). To a solution of 5.59 g (0.028 mol) of 9n in 90 mL of methylene chloride was added 10 drops of bromine. After stirring at room temperature under nitrogen for several minutes, the characteristic red color of bromine disappeared indicating initiation of the reaction. The remainder of the 1.40 mL (27.53 mmol) of bromine was added dropwise, and the reaction solution was allowed to stir at room temperature under nitrogen for 9.75 h. The reaction solution was quenched and brought to pH 8 with a saturated aqueous solution of sodium bicarbonate. The product was extracted with methylene chloride, dried (Na$_2$SO$_4$), and filtered. The solvent was removed, and the resulting residue was dried briefly under high vacuum to give 8.73 g (>100%) of 10b as a light yellow oil. $^1$H NMR (CDCl$_3$) δ 7.86 (s, 2H), 7.56 (s, 1H), 5.19-5.11 (q, 1H), 1.90 (d, 3H).

Step 3. 2-(tert-Butylamino)-3',5'-dichloropropiophenone (2n) Fumarate. To a sealable reaction tube was transferred 4.00 g (0.014 mol) of 10n with a minimal amount of methylene chloride. Most of the methylene chloride was removed via positive nitrogen flow, 15 mL (141.86 mmol) of tert-butylamine was added in one portion, and the tube was sealed and placed in an oil bath heated to 65° C. After stirring at 65° C. for 2 h, the reaction mixture was allowed to cool to room temperature. The reaction mixture was quenched and brought to pH 10 with a saturated aqueous solution of sodium bicarbonate, and the product was extracted with methylene chloride, dried (Na$_2$SO$_4$), and filtered. The solvent was removed, and the resulting residue was dried briefly under high vacuum to give 4.20 g of 2n as an orange oil. $^1$H NMR (CDCl$_3$) δ 7.86 (s, 2H), 7.58 (s, 1H), 4.27-4.19 (q, 1H), 1.25 (d, 3H), 1.05 (s, 9H). Purification by flash chromatography (silica, 9:1:40 Et$_2$O-Et$_3$N-hexane) gave 2.67 g (69%) of 2n as a yellow oil. To a solution of 2.50 g (0.009 mol) of 2n in methanol was added 1.05 g (0.009 mol) of fumaric acid. The reaction mixture was allowed to stir for 15 min, and a white solid precipitated from the solution which was collected by vacuum filtration to afford 1.69 g of 2n•fumarate as a white solid: mp 178-180° C. $^1$H NMR (CD$_3$OD) δ 8.14 (s, 2H), 7.96 (s, 1H), 4.67-4.59 (q, 1H), 1.21 (d, 3H), 1.05 (s, 9H). Anal (C$_{17}$H$_{21}$Cl$_2$NO$_5$) C, H, N.

Synthesis of 2-(N-Propylamino)-3'-chloropropiophenone (2v)

2-(N-Propylamino)-3'-chloropropiophenone (2v) Fumarate

2-Bromo-1-(3-chlorophenyl)propan-1-one (250 mg, 1.01 mmol) was dissolved in dry ether (1 mL) and the solution was chilled to 0° C. n-Propylamine (0.18 mL, 2.22 mmol) was then added all at once and the reaction mixture was allowed to warm to room temperature and stir overnight. The reaction mixture was diluted with water and ether and stirred for 5 min. The biphasic mixture was partitioned in a separatory funnel. The aqueous layer was extracted twice with ether and the combined organic extracts were washed twice with 1 M aqueous HCl. The combined acidic aqueous layers were then basified to pH 8-9 with saturated aqueous Na$_2$CO$_3$. The basified aqueous layer was extracted twice with ether and the combined organic extracts were washed with brine, dried over Na$_2$SO$_4$, filtered, and concentrated to approximately half the original volume. (Caution: In all the following concentration steps, do not concentrate to dryness or the compound will decompose). In order to remove the unreacted propylamine, MeOH (~20 mL) was added and the solution was concentrated to ~5-10 mL. This process was repeated twice more and then 30 mL of ether was added followed by the dropwise addition of 1 M HCl/ether until the solid stopped precipitating out of solution (typically 0.5 to 1 mL was needed). After stirring for 1 h, the solid was filtered, washed with ether, and dried to afford 67.1 mg (25% yield) of the hydrochloride salt of 2v as a white flaky solid: mp 188-189° C. $^1$H NMR (CD$_3$OD, 300 MHz) δ 8.07 (s, 1H), 8.01 (d, J=9.0 Hz, 1H), 7.76 (d, J=12.0 Hz, 1H), 7.61 (t, J=12.0, 6.0 Hz, 1H), 5.17 (q, J=21.0, 15.0, 6.0 Hz, 1H), 3.13-3.04 (m, 1H), 3.02-2.92 (m, 1H), 1.86-1.73 (m, 2H), 1.58 (d, J=9.0 Hz, 3H), 1.05 (t, J=15.0, 9.0 Hz, 3H); $^{13}$C NMR (CD$_3$OD, 75 MHz) ppm 196.1, 136.0, 135.9, 132.1, 129.7, 128.4, 59.6, 49.0, 20.9, 16.3, 11.2. Anal. (C$_{12}$H$_{17}$Cl$_2$NO.0.25H$_2$O)C, H, N.

The initial preparation of 2v was of the fumaric salt, using fumaric acid in place of HCl/ether, but it was difficult to repeat and the yield was <5%. It was then discovered that the hydrochloride salt resulted in more reliable isolation. The fumarate salt is reported because that is what was used for the biological testing. The fumarate salt was made from the hydrochloride salt by neutralization with aqueous sodium bicarbonate followed by extraction with ether. Fumaric acid was then added as a solution in methanol and the solution concentrated until a solid appeared, which was filtered, washed with ether, and dried to afford 2v•fumarate: mp 190-192° C. (dec). Anal. (C$_{16}$H$_{20}$ClNO$_5$.0.25H$_2$O)C, H, N.

Synthesis of 2-(N-Isopropylamino)-3'-chloropropiophenone (2w) Fumarate. Sodium bicarbonate (4 g, 0.048 mol) was suspended in a solution of 10 g (6.00, 0.024 mol) in acetonitrile (30 mL). The suspension was cooled in an ice-brine bath and a solution of isopropylamine (0.69 g, 0.012 mol) in acetonitrile (10 mL) added dropwise over a period of 10 min. After the addition was complete, the mixture was stirred in the cold for 4 h, poured into a mixture of hydrochloric acid (50 mL of 10%) and ethyl acetate (50 mL). The aqueous layer was separated, washed with ethyl acetate (25 mL) and made alkaline with ammonia hydroxide:water (1:1). The mixture was extracted with Et$_2$O (2×100 mL) and the combined ethereal extracts were dried (K$_2$CO$_3$), filtered, and concentrated to give 1.26 g of yellow oil. The fumarate salt was formed as described for 2b and recrystallized from methanol/Et$_2$O: mp 174-178° C. (dec). $^1$H NMR (CDCl$_3$) δ 7.88 (t, 1H, J=1.6 Hz), 7.78 (dd, 1H, J=2.1 Hz, J=1.2 Hz), 7.48 (d, J=2.1 Hz), 7.37 (t, J=7.8 Hz), 4.30 (q, 1H, J=7.2 Hz), 2.67 (p. 1H, J=6.3 Hz), 1.23 (d, 2H, J=15 Hz), 1.00 (t, 6H, J=6.3 Hz). Anal. (C$_{16}$H$_{20}$ClNO$_5$.0.25 H$_2$O)C, H, N.

Synthesis of 2-(N-Methyl-N-tert-butylamino)-3'-chloropropiophenone (2 cc)

Step 1. 2-Bromo-3'-chloropropiophenone (10 cc). 3'-Chloropropiophenone (10.0 g, 0.059 mol) and methylene chloride (100 mL) were placed in a 500-mL flask equipped with a magnetic stir bar. The solution was stirred under nitrogen, and bromine (3.04 mL, 59 mmol) was syringed into the flask. A small amount of bromine was added initially to catalyze the reaction. After reaction started, the remaining bromine was added over a 10-min period. The hydrogen bromide gas evolved was bubbled through a 0.1 N sodium hydroxide solution. After stirring for 16 h, the solution was transferred to a reparatory funnel. A saturated sodium bicarbonate solution was added to basify the reaction, and the aqueous layer was extracted three times with methylene chloride. The organic layer was dried (Na$_2$SO$_4$) and filtered. The solvent was removed under reduced pressure to give 14.06 g of oil. The dark orange oil was purified by flash chromatography (4:1 hexane-methylene chloride) to afford 13.90 g (95%) of 10 cc as a light orange oil. $^1$H NMR (CDCl$_3$) δ 7.99 (s, 1H), 7.93-7.88 (d, 1H), 7.61-7.56 (d, 1H), 7.49-7.40 (t, 1H), 5.29-5.19 (q, 1H), 1.94-1.89 (d, 3H).

Step 2. 2-(N-Methyl-N-tert-butylamino)-3'-chloropropiophenone (2 cc) Hydrochloride.

Compound 10 cc (5.0 g, 0.02 mol) and methylene chloride (50 mL) were placed in a pressure tube equipped with a magnetic stir bar. N-Methyl-N-tert-butylamine (4.97 mL, 41 mmol) was added to the tube. The tube was sealed, stirred, and refluxed at 75° C. for 6 h. The tube was cooled to room temperature and opened. After stirring 8 days, the solution was transferred to a separatory funnel. A saturated sodium bicarbonate solution was added to basify the reaction, and the aqueous layer was extracted three times with methylene chloride. The organic layer was dried (Na$_2$SO$_4$) and filtered through a fitted funnel packed with alumina. The solvent was removed under reduced pressure to give 3.65 g (71%) of 2 cc as a green oil. $^1$H NMR (CDCl$_3$) δ 8.09 (s, 1H), 7.94-7.89 (d, 1H), 7.50-7.45 (d, 1H), 7.40-7.32 (t, 1H), 4.66-4.56 (q, 1H), 2.16 (s, 3H), 1.30-1.25 (d, 3H), 1.19 (s, 9H). Amine 2 cc was converted to a hydrochloride salt using the procedure described for 2b. Recrystallization from isopropanol and Et$_2$O afforded 2.22 g of 2 cc•HCl as a white crystalline solid: mp 181-182° C. $^1$H NMR (CD$_3$OD) δ 8.19 (s, 1H), 8.19-8.12 (d, 1H), 7.80-7.75 (d, 1H), 7.67-7.60 (t, 1H), 5.59-5.50 (q, 1H), 2.97 (s, 3H), 1.63-1.58 (d, 3H), 1.50 (s, 9H). Anal. (C$_{14}$H$_{21}$Cl$_2$NO)C, H, N.

Synthesis of 2-(N,N-Dimethylamino)-3'-chloropropiophenone (2dd)

Compound 10 cc (2.7 g, 0.011 mol) and methylene chloride (40 mL) were placed in a sealed tube equipped with a magnetic stir bar. The tube was cooled to −78° C. with an acetone-dry-ice bath. Dimethyl amine (approximately 5 mL, b.p. −7°) was condensed into the tube. The tube was sealed, placed in an ice water bath, and stirred. After stirring 12 h, the tube was again cooled to −78° with an acetone/dry-ice bath and opened. The tube was allowed to warm to room temperature. After stirring for 4 h at room temperature, the solution was transferred to a separatory funnel. Water (75 mL) and ammonium hydroxide (10 drops) were added to basify the reaction, and the aqueous layer was extracted three times with methylene chloride. The organic layer was dried (Na$_2$SO$_4$) and filtered. The solvent was removed under reduced pressure to give 3.14 g (99%) of oil. $^1$H NMR (CDCl$_3$) δ 8.05 (s, 1H), 7.99-7.93 (d, 1H), 7.56-7.50 (d, 1H), 7.44-7.36 (t, 1H), 4.05-3.95 (q, 1H), 2.30 (s, 6H), 1.22-1.28 (d, 3H). Amine 2dd was filtered, converted to a fumarate salt using the procedure described for 2b. Recrystallization from methanol and Et$_2$O afforded 1.80 g of 2dd•fumarate as a white solid: mp 144-145° C. $^1$H NMR (CD$_3$OD) δ 8.04 (s, 1H), 8.00-7.95 (d, 1H), 7.76-7.71 (d, 1H), 7.62-7.55 (t, 1H), 6.69 (s, 2H), 2.92 (s, 6H), 1.58 (s, 3H). (Note: The α proton exchanged with the deuterated solvent; therefore, $^1$H NMR spectrum changes slightly.) Anal. (C$_{15}$H$_{18}$ClNO$_5$) C, H, N.

Synthesis of 2-(N,N-Diethylamino)-3'-chloropropiophenone (2ee) Fumarate

Compound 10 cc (4.3 g, 0.017 mol) was placed in a 250-mL flask equipped with a magnetic stir bar. The flask was cooled to 0° C. with an ice-water bath. Diethylamine (3.77 mL, 36 mmol) was added, and the reaction was stirred under nitrogen. After 12 h, the solution was transferred to a separatory funnel. A saturated sodium bicarbonate solution was added to basify the reaction, and the aqueous layer was extracted three times with Et$_2$O. The organic layer was dried (Na$_2$SO$_4$) and filtered through a fitted funnel packed with alumina. The solvent was removed under reduced pressure to give 3.98 g (95%) of 2ee as a light green oil. $^1$H NMR (CDCl$_3$) δ 8.10 (s, 1H), 8.03-7.98 (d, 1H), 7.51-7.46 (d, 1H), 7.40-7.32 (t, 1H), 4.42-4.32 (q, 1H), 2.69-2.42 (m, 4H), 1.24-1.19 (d, 3H), 1.07-0.99 (t, 6H). Amine 2ee was converted to a fumarate salt using the procedure described for 2b. Recrystallization from isopropanol and hexane afforded 2.46 g of 2ee•fumarate as a white crystalline solid: mp 119-120° C. $^1$H NMR (CD$_3$OD) δ 8.11 (s, 1H), 8.06-8.01 (d, 1H), 7.76-7.71 (d, 1H), 7.63-7.56 (t, 1H), 6.68 (s, 2H), 5.30-5.20 (q, 1H), 3.43-3.28 (m, 2H), 3.24-3.09 (m, 2H), 1.50-1.46 (d, 3H), 1.38-1.30 (t, 6H). Anal. (C$_{17}$H$_{22}$ClNO$_5$) C, H, N.

Synthesis of 2-Piperidino-3'-chloropropiophenone (2ff) Fumarate. Compound 10 cc (4.5 g, 0.018 mol) was placed in a 100-mL flask equipped with a magnetic stir bar. The flask was cooled to 0° C. with an ice-water bath. Piperidine (3.78 mL, 38 mmol) was added, and the reaction was stirred under nitrogen. After 12 h, the solution was transferred to a separatory funnel. A saturated sodium bicarbonate solution was added to basify the reaction, and the aqueous layer was extracted three times with Et$_2$O. Subsequently, more piperidine (4 mL) was added. After stirring for 24 h, the solution was transferred to a separatory funnel. A saturated sodium bicarbonate solution was added to basify the reaction, and the aqueous layer was extracted three times with methylene chloride. The organic layer was dried (Na$_2$SO$_4$) and filtered through a fritted funnel packed with alumina. The pack was washed with hexane. The solvent was removed under reduced pressure. To ensure that all of the excess piperidine was removed, methanol and toluene were added and removed under reduced pressure to give 3.32 g (72%) of 2ff as a light orange oil. $^1$H NMR (CDCl$_3$) δ 8.11 (s, 1H), 8.05-8.00 (d, 1H), 7.52-7.47 (d, 1H), 7.42-7.32 (t, 1H), 4.02-3.92 (q, 1H), 2.56-2.42 (m, 4H), 1.58-1.47 (m, 4H), 1.47-1.39 (m, 2H), 1.25-1.20 (d, 3H). Amine 2ff was converted to a fumarate salt using the procedure described for 2b. Recrystallization from isopropanol and hexane afforded 2.84 g of 2ff•fumarate as a white crystalline solid: mp 157-158° C. $^1$H NMR (CD$_3$OD) δ 8.09 (s, 1H), 8.01-7.96 (d, 1H), 7.77-7.71 (d, 1H), 7.63-7.53 (t, 1H), 6.70 (s, 3H), 5.22-5.12 (q, 1H), 3.50-3.20 (m, 4H), 1.99-1.89 (m, 4H), 1.75-1.65 (m, 2H), 1.60-1.55 (d, 3H). (Note: fumarate peak, 6.70, integrates for 3 protons. This is supported by the elemental analysis). Anal. (C$_{20}$H$_{24}$ClNO$_7$) C, H, N.

Synthesis of (1RS,2RS)-2-(N-tert-Butylamino)-1-phenyl-1-propanol (7) Hemifumarate. The title compound was prepared as previously reported (Musso, D. L. et al., Synthesis and Evaluation of the Anticonvulsant Activity of a Series of 2-amino-1-phenyl-1-propanols Derived from the Metabolites of the Antidepressant Bupropion *Bioorg. Med. Chem. Lett.* 1997, 7, 1-6) and characterized as the hemifumarate salt: m.p. 178-180° C. Anal. (C$_{15}$H$_{23}$NO$_3$) C, H, N.

Example 2

Biological Studies a) Monoamine Tranporter Binding and Uptake Studies

The competition binding assays were determined using (h)DAT, (h)SERT, and (h)NET, stably expressed in HEK293 cells, and the non-selective radioligand [$^{125}$I]RTI-55 for the analogues 2a-2ff and 7 (See Table 4, below). The HEK-(h)DAT, -(h)SERT, and -(h)NET cells were also used to evaluate the compounds' ability to block the reuptake of [$^3$H]dopamine ([$^3$H]DA), [$^3$H]serotonin ([$^3$H]5HT), and [$^3$H]norepinephrine ([$^3$H]NE) (Table 4).

Bupropion analogues with better DAT binding (lower K$_i$ values) and [$^3$H]DA uptake (lower IC$_{50}$ values) were obtained by (a) replacing the methyl group α to the ketone group with medium-size alkyl groups; (b) changing the type and number of substituents on the 3-chlorophenyl ring; and (c) replacing the N-tert-butyl group with other N-alkyl groups. Since for the most part the rank order potency of the binding assays mirror those of the uptake values, only the monoamine uptake values will be discussed.

Bupropion has IC$_{50}$ values of 945 and 443 nM for DA and NE uptake inhibition, respectively. Since the K$_i$ value for binding to the SERT was >10 μM, the 5HT uptake IC$_{50}$ was not determined. Thus, bupropion is 3.5-times less potent inhibitor of DA uptake than cocaine. Bupropion and cocaine have almost equal potency for NE uptake, and cocaine with an IC$_{50}$ value of 318 nM for 5HT uptake is much more potent than bupropion. Analogues 2o-2q obtained by replacing the α methyl group in bupropion with an ethyl, propyl, or butyl group had IC$_{50}$ values of 31, 33, and 69 nM, respectively, compared to 945 nM for bupropion and were the most DA efficacious analogues. Analogues 2s-2t with larger hexyl and isobutyl α substituents had IC$_{50}$ values of 135 and 440 nM and, thus, were also better DA uptake inhibitors than bupropion. Replacement of the α methyl group in bupropion with a much larger 2-(cyclohexyl)ethyl α substituent to give 2u resulted in complete loss of DA efficacy (IC$_{50}$ value of >10 μM).

Changing the aromatic substituent pattern of bupropion also led to analogues with better IC$_{50}$ values for DA uptake inhibition. For example, the 3,4-dichlorophenyl analogue 2j and the 3-chloro, 4-methylphenyl analogue 2k with IC$_{50}$ values of 271 and 650 nM, respectively, were 3.5- and 2-times more potent than bupropion. The 3-bromophenyl and 4-bromo, 3-methylphenyl analogues 2d and 2l with IC$_{50}$ values of 950 nM were as potent as bupropion. Replacing the α methyl group of 2j with an ethyl or propyl group gave analogues 2aa and 2bb, which had slightly lower IC$_{50}$ values than 2j. Replacement of the 3-chlorophenyl ring with a thiophene ring led to 3, which had no efficacy for DA uptake inhibition.

Replacement of the N-tert-butyl group with an N-cyclopropyl or N-cyclobutyl group gave 2x and 2y with IC$_{50}$ values of 265 and 258 nM, which are 3.6- and 3.7-times more potent than bupropion. The N-cyclopentyl analogue 2z had an IC$_{50}$ of 980 nM, almost identical to that of bupropion. The N-isopropyl analogue 2w with an IC$_{50}$ value of 2000 nM was 2-times less potent than bupropion. Surprisingly, the N-propyl analogue 2v was inactive. None of the N,N-disubstituted analogues 2cc-2ff had high efficacy for DA uptake inhibition. The best compound was the N-piperidino analogue 2ff, which had an IC$_{50}$ value of 1033 nM.

Similar to bupropion, most bupropion analogues showed little efficacy for 5HT uptake inhibition. The 3-chloro-4-methylphenyl, 3-methyl-4-bromopheyl, and N-cyclopentyl analogues 2k, 2l, and 2y with IC$_{50}$ values of 400, 473, and 185 nM for 5HT uptake inhibition, respectively, were the most potent.

Most analogues also showed NE uptake inhibition no better than five times that of bupropion. However, analogues 2bb, 2y, and 2aa with IC$_{50}$ values of 43, 86, and 135, respectively, were 34, 17, and 10 times better as NE uptake inhibitors than bupropion.

Replacement of the cyclopentyl group in 2z with a cyclobutyl or cyclopropyl group to give 2y and 2x, respectively, resulted in significant changes in monoamine uptake properties. Compound 2z had an IC$_{50}$ value of 980 nM for DA uptake compared to 258 and 265 nM for 2y and 2x, respectively. Surprisingly, the IC$_{50}$ value for NE uptake for 2z of 221 nM improved to 86 nM for the cyclobutyl analogue 2y but increased to 2150 nM for the cyclopropyl analogue 2x. The cyclopentyl analogue 2z was totally inactive as a 5HT uptake inhibitor, whereas the cyclobutyl analogue 2y has an IC$_{50}$ of 185 nM for this transporter, which is better than the other bupropion analogues studied (Table 4). Changing the cyclopentyl in 2z to the cyclopropyl group in 2x also resulted in improved 5HT uptake inhibition but only to an IC$_{50}$ value of 3180 nM. We found that 2v, which can be viewed as the open ring analogue of 2x, was inactive at all three transporters. We found that reduction of the carbonyl of bupropion analogue 2b to give 7 resulted in loss of affinity at the DAT and NET but gave a significant increase in potency for 5HT uptake from >10,000 nM in bupropion to 1240 nM in 7.

TABLE 4

Comparison of Dopamine, Serotonin, and Norepinephrine Transporter
Binding and Uptake Studies in C6hDAT, HEK-hSERT, and HEK-hNET Cells for
Bupropion Analogues Compounds 2a-2ff

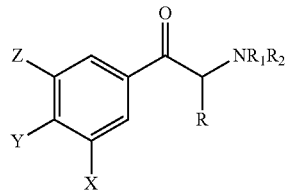

| Cmpd | R | R₁ | R₂ | X | Y | Z | Binding,[a] $K_i$ (nM) DAT | SERT | NET | Uptake,[a] $IC_{50}$ (nM) [³H] DA | [³H]5-HT | [³H] NE |
|---|---|---|---|---|---|---|---|---|---|---|---|---|
| cocaine [b] | | | | | | | 272 ± 60 | 601 ± 130 | 830 ± 147 | 267 ± 47 | 318 ± 57 | 385 ± 40 |
| 2a (bupropion) | CH₃ | H | C(CH₃)₃ | Cl | H | H | 871 ± 126 | >10 μM | 6970 ± 2620 | 945 ± 213 | [c] | 443 ± 245 |
| 2b | CH₃ | H | C(CH₃)₃ | H | H | H | 5730 ± 480 | >10 μM | 5700 ± 150 | 2310 ± 750 | [c] | 8700 ± 1200 |
| 2c | CH₃ | H | C(CH₃)₃ | F | H | H | 4510 ± 460 | >10 μM | >10 μM | 1460 ± 220 | [c] | [c] |
| 2d | CH₃ | H | C(CH₃)₃ | Br | H | H | 4200 ± 1200 | >10 μM | >7140 ± 640 | 950 ± 210 | [c] | 6500 ± 1000 |
| 2e | CH₃ | H | C(CH₃)₃ | CH₃ | H | H | >10 μM | >10 μM | >10 μM | [c] | [c] | [c] |
| 2f | CH₃ | H | C(CH₃)₃ | H | Cl | H | 2195 ± 151 | >10 μM | >10 μM | 2319 ± 429 | [c] | [c] |
| 2g | CH₃ | H | C(CH₃)₃ | H | Br | H | 1918 ± 221 | 4170 ± 730 | >10 μM | 1295 ± 375 | 2520 ± 610 | [c] |
| 2h | CH₃ | H | C(CH₃)₃ | H | CH₃ | H | >10 μM | >10 μM | 6840 ± 1368 | [c] | [c] | 4100 ± 860 |
| 2i | CH₃ | H | C(CH₃)₃ | F | F | H | >10 μM | >10 μM | >10 μM | [c] | [c] | [c] |
| 2j | CH₃ | H | C(CH₃)₃ | Cl | Cl | H | 472 ± 81 | 1480 ± 310 | 5400 ± 1200 | 271 ± 96 | >10 μM | 2100 ± 380 |
| 2k | CH₃ | H | C(CH₃)₃ | Cl | CH₃ | H | 1150 ± 370 | 2100 ± 510 | 5100 ± 860 | 650 ± 150 | 400 ± 190 | 900 ± 130 |
| 2l | CH₃ | H | C(CH₃)₃ | CH₃ | Br | H | 1740 ± 440 | 1215 ± 90 | 4600 ± 601 | 950 ± 310 | 473 ± 74 | 1623 ± 35 |
| 2m | CH₃ | H | C(CH₃)₃ | F | H | F | 5660 ± 490 | >10 μM | >10 μM | 5600 ± 1800 | [c] | [c] |
| 2n | CH₃ | H | C(CH₃)₃ | Cl | H | Cl | >10 μM | >10 μM | >10 μM | [c] | [c] | [c] |
| 2o | C₂H₅ | H | C(CH₃)₃ | Cl | H | H | 459 ± 50 | >10 μM | 3195 ± 145 | 31 ± 9 | [c] | 969 ± 410 |
| 2p | C₃H₇ | H | C(CH₃)₃ | Cl | H | H | 96 ± 20 | >10 μM | 1171 ± 260 | 33 ± 7 | [c] | 472 ± 93 |
| 2q | C₄H₉ | H | C(CH₃)₃ | Cl | H | H | 350 ± 100 | >10 μM | 3190 ± 850 | 69 ± 23 | [c] | 400 ± 190 |
| 2r | C₅H₁₁ | H | C(CH₃)₃ | Cl | H | H | 709 ± 8.0 | >10 μM | 4300 ± 1300 | 1570 ± 570 | [c] | 2000 ± 1000 |
| 2s | C₆H₁₃ | H | C(CH₃)₃ | Cl | H | H | 510 ± 120 | >10 μM | 2580 ± 700 | 135 ± 80 | [c] | 4890 ± 580 |
| 2t | (CH₃)₂CHCH₂ | H | C(CH₃)₃ | Cl | H | H | 140 ± 14 | 6200 ± 1800 | 2300 ± 700 | 440 ± 180 | >10 μM | 360 ± 190 |
| 2u | (C₆H₁₁)CH₂CH₂ | H | C(CH₃)₃ | Cl | H | H | 1700 ± 780 | 6200 ± 1500 | 3800 ± 1700 | >10 μM | >10 μM | >10 μM |
| 2v | CH₃ | H | CH₂CH₂CH₃ | Cl | H | H | >10 μM | >10 μM | >10 μM | [c] | [c] | [c] |
| 2w | CH₃ | H | CH(CH₃)₂ | Cl | H | H | 3980 ± 230 | >10 μM | >10 μM | 2000 ± 516 | [c] | [c] |
| 2x | CH₃ | H | CH(CH₂CH₂) | Cl | H | H | 1150 ± 370 | 3420 ± 260 | 4000 ± 1200 | 265 ± 94 | 3180 ± 170 | 2150 ± 850 |
| 2y | CH₃ | H | CH(CH₂CH₂CH₂) | Cl | H | H | 343 ± 72 | 3450 ± 610 | 1800 ± 110 | 258 ± 46 | 185 ± 49 | 86 ± 32 |
| 2z | CH₃ | H | CH(CH₂CH₂CH₂CH₂) | Cl | H | H | 2200 ± 490 | >10 μM | 5700 ± 400 | 980 ± 340 | [c] | 221 ± 94 |
| 2aa | C₂H₅ | H | C(CH₃)₃ | Cl | Cl | H | 278 ± 43 | 860 ± 230 | 2240 ± 510 | 175 ± 55 | 790 ± 320 | 135 ± 4.9 |
| 2bb | C₃H₇ | H | C(CH₃)₃ | Cl | Cl | H | 43.7 ± 6.5 | 842 ± 50 | 520 ± 100 | 84 ± 28 | 1580 ± 560 | 43 ± 14 |
| 2cc | CH₃ | CH₃ | C(CH₃)₃ | Cl | H | H | 6400 ± 1200 | >10 μM | >10 μM | 2060 ± 340 | [c] | [c] |

TABLE 4-continued

Comparison of Dopamine, Serotonin, and Norepinephrine Transporter Binding and Uptake Studies in C6hDAT, HEK-hSERT, and HEK-hNET Cells for Bupropion Analogues Compounds 2a-2ff

| Cmpd | R | $R_1$ | $R_2$ | X | Y | Z | Binding,[a] $K_i$ (nM) DAT | SERT | NET | Uptake,[a] $IC_{50}$ (nM) [$^3$H] DA | [$^3$H]5-HT | [$^3$H] NE |
|---|---|---|---|---|---|---|---|---|---|---|---|---|
| 2dd | $CH_3$ | $CH_3$ | $CH_3$ | Cl | H | H | 4133 ± 548 | >10 μM | 3090 ± 740 | 1534 ± 222 | [c] | 1260 ± 290 |
| 2ee | $CH_3$ | $CH_2CH_3$ | $CH_2CH_3$ | Cl | H | H | 2214 ± 308 | >10 μM | 4476 ± 107 | 1744 ± 288 | [c] | 4603 ± 986 |
| 2ff | $CH_3$ | $CH_2CH_2CH_2CH_2CH_2$ | | Cl | H | H | 1148 ± 298 | 5479 ± 824 | 4760 ± 1540 | 1033 ± 287 | 970 ± 178 | 4798 ± 947 |

[a] Values for the mean ± standard error of three independent experiments, each conducted with triplicate determination
[b] Data taken from Musso et al., Synthesis and Evaluation of the Anticonvulsant Activity of a Series of 2-amino-1-phenyl-1-propanols Derived from the Metabolites of the Antidepressant Bupropion. *Bioorg. Med. Chem. Lett.* 1997, 7, (1), 1-6
[c] Not determined In addition, 2x is a substrate for the serotonin transporter with an $EC_{50}$ of 283 nM, which could enhance efficacy at the 5HT (See Table 5, below). The improved efficacy at DA and 5HT combined with weaker efficacy at NE suggests that 2x may be a better pharmacotherapy for treating cocaine, methamphetamine, and nicotine addiction than bupropion. Indeed 2x proved to be superior to bupropion in all tested animal assays, which are presented below.

TABLE 5

Comparison of the 5-HT Releasing/Substrate Activity of a series of N-Cyclopropylbupropion analogs using rat brain synaptosomes

| Structure | 5HT Release (EC50, nM) |
|---|---|
| (Compound 2x) 3-Cl phenyl | 283 ± 32 |
| 3-Br phenyl | 383 ± 56 |
| 3-CH₃ phenyl | 890 ± 63 |
| 3-OCH₃ phenyl | 676 ± 197 |
| 4-Cl phenyl | 2704 ± 314 |
| 4-CH₃ phenyl | 707 ± 69 |

TABLE 5-continued

Comparison of the 5-HT Releasing/Substrate Activity of a series of N-Cyclopropylbupropion analogs using rat brain synaptosomes

| Structure | 5HT Release (EC50, nM) |
|---|---|
| 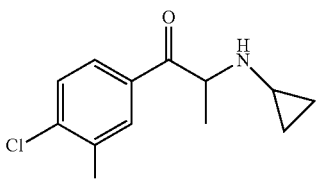 | 148 ± 35 |
| 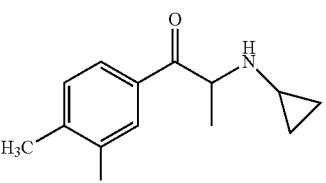 | 139 ± 130 | b) Locomotor Activity Studies

The bupropion analogues were evaluated for locomotor activity using mice in first a 1-h study followed by an 8-h time course study using previously reported methods. The results were compared to the locomotor activity results obtained for cocaine in both studies and to bupropion in the 8-h study. Cocaine had $IC_{50}$ values of 8.5-11 mg/kg as determined in several separate experiments in the 1-h study. The $ED_{50}$ value for bupropion was 6.5 mg/kg. Cocaine's locomotor efficacy was set at 100%, and all analogues were compared to cocaine's maximum efficacy. $ED_{50}$ values in mg/kg, compounds' maximal effect as a percent of cocaine's maximal effect in the first 30 min (1-h study), compounds' maximal effect as a percent of cocaine's maximal effect calculated based on a 30-min time period in which maximum stimulation occurred (8-h study), and time period of maximum effect are listed in Table 6, below.

In the 1-h observation protocol, seven analogues had $IC_{50}$ values similar to cocaine ($IC_{50}$=5.2-12.1 mg/kg). The $IC_{50}$ values for 14 compounds ranged from 13.5 to 54.6 mg/kg, and thirteen analogues did not show locomotor activity. Seven analogues showed stimulation similar to cocaine (>84% peak). The remaining 20 compounds with locomotor activities had peak effects of 41-81% of that of cocaine. In the 8-h locomotor observation protocol, 7 compounds listed as well as bupropion had locomotor efficacy similar to cocaine (>84% peak). The remaining 16 analogues listed had efficacy ranging from 31-78%. The $ED_{50}$ values ranged from 4.4 mg/kg for 2 h to 60.8 mg/kg for 2k. Five analogues, 2b, 2c, 2m, 2x, and 2z, had locomotor activity in both the 1-h and 8-h tests, and seven analogues, 2d, 2h, 2r, 2s, 2t, 2aa, and 2 cc, were weak stimulants in both tests. Four analogues, 2o, 2p, 2w, and 2dd, showed activity similar to cocaine in the 1-h protocol but weakened significantly in the 8-h time-course study. Five analogues, 2b, 2c, 2m, 2x, and 2z, were strong stimulants in both studies. Four compounds, 2k, 2aa, 2bb, and 2ee, showed moderate activity in the 1-h test with increased activity in the time-course study. Compounds 2g, 2u, 2ff, and 6 were inactive in the 1-h test but showed weak stimulant activity in the 8-h protocol. Several compounds, 2g, 2j, 2p, 2s, 2t, 2dd, 2ff, and 6, had periods of maximum stimulatory effects at times of 1 h or greater. Bupropion's period of maximum stimulatory effect was 0-30 min, which was similar to that of cocaine and analogues 2b-d, 2m, 2o, 2q, and 2x-2bb. Compounds 2j, 2t, and 2ff, with a range of 260-350 min time periods of maximum effects, had very slow onset of stimulatory activity. Compounds 2j, 2p, 2t, 2ff, and 6 also had duration of locomotor activity greater than 3 h. Bupropion had a duration of locomotor activity of approximately 2-4.5 h. Analogues 2o-q, which were 31-, 29-, and 14-times more potent than bupropion as DA uptake inhibitors had very long durations of locomotor activity of 360, 210-480, and 40-460 min, respectively. In addition, analogue 2x, which was 3.6-times more potent than bupropion as a DA uptake inhibitor with increased potency as a 5HT uptake inhibitor, possessed a duration of locomotor activity of 350 min, which is longer than bupropion. Analogue 2o also had a much slower onset of locomotor activity. The cyclopentylbupropion analogue 2z had an $ED_{50}$ value of 10.6 with long durations of action.

TABLE 6

Comparison of Locomotor Activity for Bupropion Analogues at the 1- and 8-Hour Observation Protocols

| | Locomotor Activity | | | | | |
|---|---|---|---|---|---|---|
| | 1-Hour | | 8-Hour | | | |
| Cmpd | $ED_{50}$[a] mg/kg | % Peak[b] Cocaine | $ED_{50}$[a] mg/kg | Peak[c] Cocaine | Time,[d] min Period, max | Time, min Period, length |
| cocaine | 8.5-11[e] | 100 | | 100 | 0-30 | 40-100 |
| 2a | | | 6.5 | 87 | 0-30 | 130-270 |
| bupropion | | | | | | |
| 2b | 8.1 | 120 | 10.5 | 98 | 0-30 | |
| 2c | 16.1 | 84 | 16.6 | 90 | 0-30 | 150 |
| 2d | 10.6 | 72 | 12.9 | 57 | 0-30 | 120 |
| 2e | 31 | 76 | | | | |
| 2f | NE[f] | | | | 180-210 | |
| 2g | NE[f] | | 32.0 | 54 | 140-170 | 160 |
| 2h | 8.77 | 65 | 4.4 | 52 | 30-60 | 60-140 |
| 2i | 54.6 | 58 | NE | | | |
| 2j | NE[f] | | 39.1 | 61 | 270-300 | 140-240 |
| 2k | 31.9 | 74 | 60.8 | 87 | 10-40 | 60 |
| 2l | NE[f] | | 12.8 | 46 | 50-80 | 240 |
| 2m | 39.7 | 93 | 33.7 | 95 | 0-30 | 280 |
| 2n | NE[f] | | | | | |
| 2o | 12.1 | 88 | 19.3 | 62 | 0-30 | 360 |
| 2p | 17.2 | 96 | 16.3 | 72 | 90-120 | 210-480 |
| 2q | 13.5 | 81 | 13.1 | 110 | 0-30 | 40-460 |
| 2r | 5.82 | 66 | 13.4 | 78 | 60-90 | 280-460 |
| 2s | 33.3 | 61 | 9.0 | 60 | 110-140 | 130-140 |
| 2t | 47.7 | 62 | 22.1 | 35 | 260-290 | 320 |
| 2u | NE[f] | | 15.3 | 47 | 60-90 | 60-160 |
| 2v | NE[f] | | NE[f] | | | |
| 2w | 22.7 | 84 | 7.4 | 65 | 20-50 | 50-160 |
| 2x | 14.7 | 94 | 14.7 | 94 | 0-30 | 350 |
| 2z | 10.6 | 110 | 10.6 | 110 | 0-30 | 330-340 |
| 2aa | 50.3 | 41 | 42.2 | 84 | 0-30 | 60 |
| 2bb | 18.1 | 49 | 35.0 | 100 | 0-30 | 470 |
| 2cc | 14.9 | 78 | 11.2 | 67 | 80-110 | 200-340 |
| 2dd | 11.0 | 100 | 13.9 | 52 | 90-120 | 180-190 |
| 2ee | 16.6 | 55 | 20.0 | 90 | 20-50 | 130-240 |
| 2ff | NE[f] | | 15.0 | 45 | 320-350 | 470 |

[a]Dose to produce 50% of the compound's maximal effect.
[b]Compound's maximal effects as a percent of cocaine's maximal effects in the first 30 min.
[c]Compound's maximal effect as a percent of cocaine's maximal effect calculated based on 30 min time period in which maximum stimulation occurred.
[d]Time period of maximum effect.
[e]Range of $ED_{50}$ for several experiments.
[f]No locomotor activity or depressant effect.

c) Cocaine Discrimination

The compounds were evaluated for generalization with the cocaine cue by lever choice using standard 2-lever operant chambers in a drug-discrimination task in rats using i.p. administration. Table 7 shows the percent of rats choosing the cocaine lever at various doses of compounds along with $ED_{50}$ values where lever choice reached 75%. Analogues were also evaluated for generalization of cocaine using a time-course study with oral administration (Table 8, below) as previously reported (Carroll, F. I. et al., Effects of Dopamine Transporter Selective 3-Phenyltropane Analogs on Locomotor Activity, Drug Discrimination, and Cocaine Self-administration after Oral Administration. *Eur. J Pharmacol.* 2006, 553, (1-3), 149-156). Compounds were dosed p.o. in a volume of 1 mL/kg at 45, 90, 180, or 360 min before the session. Results for a compound were again tabulated as the percent of subjects choosing the cocaine lever.

Some bupropion analogues showed full generalization of the cocaine cue with $ED_{50}$ values of 4.84 to 36.7 mg/kg in the initial cocaine discrimination study. Bupropion substituted only partially for the discrimination stimulus effects of cocaine. The lowest dose yielding maximum substitution (10 mg/kg) resulted in 67% cocaine-appropriate responding. However, response rate was increased relative to vehicle control following 5-25 mg/kg. The N-cyclopropyl analogue 2x with partial generalization of 67% at 5 and 10 mg/kg also affected response rate at 25-100 mg/kg similar to bupropion. The more potent DA uptake inhibitors 2o-2q, which showed long durations of activity in the locomotor activity test, all showed full generalization at 25 mg/kg.

All analogues tested in the time-course study (see Table 8, below) showed full generalization in at least one time point. $ED_{50}$ values ranged from 5.36 to 52.4 mg/kg. Bupropion showed full generalization at 45 min following a 50 mg/kg dose and partial generalization at 90 min after a 50-mg/kg dose. The $ED_{50}$ for drug-appropriate responding 45 min following bupropion was 23.2 mg/kg.

Analogue 2p showed partial generalization at 45 min following a 50 mg/kg dose, full generalization at 45 and 90 min, and partial generalization at 180 min following a 100 mg/kg dose. Compound 2x showed partial generalization at 45 min following a 10-mg/kg and 25 mg/kg dose and full generalization at 90 and 180 min at a 25 mg/kg dose.

Even though there was a general correlation between the $IC_{50}$ values for DA uptake and $ED_{50}$ values for cocaine generalization, there were several exceptions. For example, the most potent analogue in the cocaine discrimination study was 2dd with an $ED_{50}$ value of 4.84 mg/kg. However, the $IC_{50}$ value for 2dd for DA uptake inhibitions was 1534 nM compared to 943 nM for bupropion. Analogue 2j with an $ED_{50}$ value of 271 nM was 3.5-times more potent as a DA uptake inhibitor than bupropion but did not even show partial generalization.

In the time-course study, bupropion showed full generalization at 45 min following a 50 mg/kg dose and partial generalization at 90 min after a 50-mg/kg dose. The $ED_{50}$ for drug-appropriate responding 45 min following bupropion was 23.2 mg/kg. Compound 2x showed only partial generalization at 45 min (slower on-set) following a 10-mg/kg and 25-mg/kg dose and full generalization at 90 and 180 min at a 25-mg/kg dose (longer lasting).

TABLE 7

Effect of Bupropion Analogues in Rats Trained to Discriminate Cocaine after IP Administration

| Compound | Dose (mg/kg), % cocaine lever responding | | | | | Full Generalization $ED_{50}$ (mg/kg) | Comments[a] |
|---|---|---|---|---|---|---|---|
| | 5 | 10 | 25 | 50 | 100 | | |
| Bupropion | 0 | 67 | 66 | | | | A |
| 2b | 3 | 83 | 83 | | | 5.65 | B |
| 2c | 1 | 0 | 50 | 10 | | 10.76 | B |
| 2d | 1 | 27 | 83 | | | 11.4 | B |
| 2f | 0 | 33 | 17 | 0 | 34 | | B |
| 2g | | 1 | 17 | 17 | 0 | | B |
| 2h | 0 | 0 | 17 | 67 | 10 | 36.7 | C |
| 2i | | 2 | 17 | 47 | | | C |
| 2j | | 0 | 17 | 34 | 2 | | B |
| 2l | | 0 | 0 | 17 | 67 | | C |
| 2m | | 17 | 50 | 83 | | 17.93 | B |
| 2o | 3 | 50 | 10 | | | 8.23 | C |
| 2p | 1 | 33 | 83 | | | 11.9 | D |
| 2q | 1 | 67 | 10 | | | 8.17 | E |
| 2r | 0 | 0 | 34 | 17 | | | F |
| 2s | 0 | 0 | 49 | 50 | 67 | | B |
| 2u | 0 | 0 | 70 | | | | B[b] |
| 2x | 6 | 67 | 34 | 17 | 17 | | F |
| 2z | 2 | 0 | 66 | 83 | | 10.8 | H |
| 2aa | 1 | 10 | 10 | | | 15.03 | B |
| 2bb | 1 | 17 | 10 | | | 6.95 | B |
| 2cc | 0 | 49 | 50 | | | | F |
| 2dd | 0 | 83 | 83 | 10 | | 4.84 | H |
| 2ee | 1 | 66 | 82 | | | 5.88 | I |
| 2ff | | 6 | 17 | 33 | 34 | | B |

[a]Response rate comments:
A = The average response rate was increased relative to vehicle control following 5 to 25 mg/kg, with a maximum effect at 5 mg/kg (127% of vehicle control). The average response rate decreased to 30% of vehicle control following 50 mg/kg bupropion.
B = Response rate failed to show significant change.
C = Response rate was reduced following 100 mg/kg.
D = Response rate increased following 25 mg/kg.
E = Response rate was increased following 5 mg/kg.
F = Response rate was reduced following 25-100 mg/kg.
G = Response rate decreased following 50 and 100 mg/kg.
H = Response rate was decreased following 25 mg/kg.
I = Response rate was decreased following 10 and 25 mg/kg.
[b]Adverse effects were seen at 50 mg/kg.

TABLE 8

Drug Discrimination Effects of Bupropion and Bupropion Analogues in Rats (p.o.) in a Time Course Study

| Compound | Pre-treatment time | Dose (mg/kg), % cocaine lever responding | | | | | | | $ED_{50}$ (mg/kg) | comments[a] |
|---|---|---|---|---|---|---|---|---|---|---|
| | | 2.5 | 5 | 10 | 25 | 50 | 100 | 200 | | |
| bupropion | 45 | 0 | 0 | 0 | 50 | 83 | | | 23.2 | A |
| | 90 | 0 | 0 | 0 | 0 | 50 | | | | |
| | 180 | 0 | 0 | 0 | 22 | 17 | | | | |
| | 360 | 0 | 0 | 0 | 0 | 0 | | | | |
| 2b | 45 | 6 | 0 | 0 | 51 | 83 | | | 25.6 | A |
| | 90 | 1 | 0 | 0 | 33 | 33 | | | | |
| | 180 | 0 | 33 | 3 | 20 | 50 | | | | |
| | 360 | 0 | 0 | 0 | 34 | 4 | | | | |

TABLE 8-continued

Drug Discrimination Effects of Bupropion and Bupropion Analogues in Rats (p.o.) in a Time Course Study

| Compound | Pre-treatment time | Dose (mg/kg), % cocaine lever responding | | | | | | | $ED_{50}$ (mg/kg) | comments[a] |
|---|---|---|---|---|---|---|---|---|---|---|
| | | 2.5 | 5 | 10 | 25 | 50 | 100 | 200 | | |
| 2c | 45 | | 17 | 17 | 49 | 66 | 95 | | 27.1 | B |
| | 90 | | 0 | 0 | 16 | 33 | 75 | | | |
| | 180 | | 0 | 33 | 0 | 17 | 82 | | | |
| | 360 | | 0 | 0 | 0 | 0 | 50 | | | |
| 2d | 45 | 13 | 0 | 0 | 17 | 51 | 67 | 100 | 52.4 | C, D |
| | 90 | 0 | 8 | 0 | 0 | 10 | 56 | 100 | | |
| | 180 | 0 | 0 | 0 | 0 | 0 | 33 | 5 | | |
| | 360 | 33 | 3 | 0 | 0 | 0 | 13 | 33 | | |
| 2m | 45 | 0 | 16 | 0 | 4 | 67 | 18 | | 43.6 | E |
| | 90 | 20 | 7 | 33 | 25 | 58 | 84 | | | |
| | 180 | 0 | 0 | 0 | 0 | 20 | 17 | | | |
| | 360 | 0 | 0 | 2 | 7 | 0 | 0 | | | |
| 2p | 45 | 0 | 17 | 33 | 33[b] | 50[c] | 100[d] | | 22.2 | F |
| | 90 | 0 | 0 | 0 | 33[b] | 17[c] | 100[d] | | | |
| | 180 | 0 | 11 | 17 | 0[b] | 17[c] | 50[d] | | | |
| | 360 | 0 | 0 | 2 | 0[b] | 16[c] | 1 | | | |
| 2q | 45 | | 17 | 0 | 0 | 83 | | | 37.9 | A |
| | 90 | | 0 | 0 | 0 | 17 | | | | |
| | 180 | | 26 | 14 | 0 | 17 | | | | |
| | 360 | | 0 | 0 | 0 | 0 | | | | |
| 2s | 45 | | | 0 | 0 | 83 | | | 37.9 | G |
| | 90 | | | 0 | 0 | 17 | | | | |
| | 180 | | | 0 | 0 | 25 | | | | |
| | 360 | | | 0 | 0 | 0 | | | | |
| 2x | 45 | 17 | 17 | 57 | 67 | | | | 13.3 | H |
| | 90 | 0 | 0 | 33 | 83 | | | | | |
| | 180 | 17 | 0 | 33 | 83 | | | | | |
| | 360 | 0 | 0 | 0 | 0 | | | | | |
| 2z | 45 | 11 | 50 | 51 | 67 | 83 | | | 8.28 | A, I |
| | 90 | 50 | 0 | 17 | 67 | 83 | | | | |
| | 180 | 0 | 0 | 0 | 67 | 34 | | | | |
| | 360 | 0 | 0 | 0 | 34 | 16 | | | | |
| 22aa | 45 | 33 | 17 | 33 | 50 | 83 | | | 15.8 | A |
| | 90 | 17 | 1 | 0 | 33 | 67 | | | | |
| | 180 | 50 | 0 | 0 | 1 | 50 | | | | |
| | 360 | 17 | 0 | 2 | 33 | 17 | | | | |
| 2bb | 45 | 0 | 0 | 17 | 58 | | | | 17.29 | A |
| | 90 | 0 | 13 | 0 | 83 | | | | | |
| | 180 | 0 | 0 | 3 | 17 | | | | | |
| | 360 | 0 | 0 | 0 | 0 | | | | | |
| 2dd | 45 | 18 | 30 | 83 | | | | | 5.36 | A |
| | 90 | 0 | 0 | 100 | | | | | | |
| | 180 | 17 | 0 | 33 | | | | | | |
| | 360 | 0 | 0 | 17 | | | | | | |

[a]Response rate comments:
A = No significant change in response rate.
B = Response rate was reduced at 50 and 100 mg/kg.
C = response rate was decreased at 200 mg/kg.
D = Four of 6 rats failed to complete the first fixed ratio at 180 min following 200 mg/kg.
E = Response rate was decreased 90 min following 50 mg/kg.
F = Response rate was decreased following 2.5 and 5 mg/kg at 45 min.
G = Response rate was increased relative to vehicle control 45 min following 10 mg/kg of 2s.
H = Response rate failed to show significant change as a function of 2x at the 90-min pretreatment interval. Salivation was observed in 2/24 rats following 25 mg/kg of 2x.
I = Decreased food consumption was observed following 25 mg/kg (1/24) rats and 50 mg/kg (1/24) rats.
[b]Dose = 20 mg/kg.
[c]Dose = 40 mg/kg.
[d]Dose = 80 mg/kg.

d) Overview of Biological Studies

In summary, bupropion analogues with better DAT binding (lower $K_i$ values) and [$^3$H]DA uptake (lower $IC_{50}$ values) were obtained by (a) replacing the methyl group a to the ketone group with medium-size alkyl groups; (b) changing the type and number of substituents on the 3-chlorophenyl ring; and (c) replacing the N-tert-butyl group with other N-alkyl groups. A number of bupropion analogues showed monoamine efficacy and an animal behavior profile that suggest they might be better indirect dopamine agonist than bupropion. Analogs 2o-2q and 2x had the best overall profiles with 2x being the most interesting. Compound 2x was more potent than bupropion in the DA uptake inhibition test and was more selective for DA uptake relative to NE uptake than bupropion. Unlike bupropion, 2x also has efficacy as a 5HT uptake inhibitor. Studies from our laboratory as well as others have reported animal behavioral studies that show that reduction of cocaine self-administration can be enhanced by 5HT uptake inhibition. The activity of 2x in an initial drug discrimination study is very similar to that of bupropion. More importantly, 2x was more potent than bupropion in the time-course discrimination study and had a slower on-set and longer duration of action. The in vitro efficacy and animal behavioral properties thought to be necessary for an indirect dopamine agonist pharmacotherapy for treating abuse of cocaine, methamphetamine, and nicotine are both better for 2x than for bupropion.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A compound according to the structure:

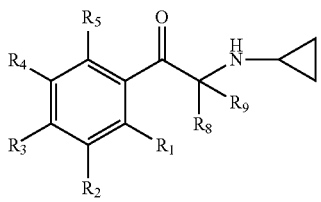

Formula Ib wherein:

$R_1$-$R_5$ are each independently selected from H, OH, substituted or unsubstituted C1-4 alkyl, substituted or unsubstituted C1-3 alkoxy, substituted or unsubstituted C2-4 alkenyl, substituted or unsubstituted C2-4 alkynyl, halo, amino, acylamido, CN, $CF_3$, $NO_2$, $N_3$, $CONH_2$, $CO_2R_{12}$, $CH_2OR_{12}$, $NR_{12}R_{13}$, $NHCOR_{12}$, $NHCO_2R_{12}$, $CONR_{12}R_{13}$; C1-3 alkylthio, $R_{12}SO$, $R_{12}SO_2$, $CF_3S$, and $CF_3SO_2$;

$R_8$ is H or substituted or unsubstituted C1-10 alkyl;

$R_9$ is substituted or unsubstituted C2-C7 alkyl;

$R_{12}$ and $R_{13}$ are each independently H or substituted or unsubstituted C1-10 alkyl;

and wherein $R_1$ and $R_8$ may be joined to form a cyclic ring;

or a pharmaceutically acceptable ester, amide, salt, solvate, or stereoisomer thereof.

2. The compound according to claim 1, wherein one or more of $R_1$, $R_2$, $R_3$, $R_4$, and $R_5$ is a substituent other than H.

3. The compound according to claim 2, wherein the substituent comprises halo.

4. The compound according to claim 3, wherein the halo is chloro.

5. A pharmaceutical composition comprising a compound of claim 1 and a pharmaceutically acceptable carrier.

* * * * *